(12) United States Patent
Wang et al.

(10) Patent No.: US 11,364,280 B2
(45) Date of Patent: Jun. 21, 2022

(54) METHOD FOR BLOCKING STRESS-INDUCED TUMOR PROGRESSION

(71) Applicant: Taipei Veterans General Hospital, Taipei (TW)

(72) Inventors: Mong-Lien Wang, Taipei (TW); Hsiao-Yun Chen, Taipei (TW); Shih-Hwa Chiou, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 402 days.

(21) Appl. No.: 16/387,300

(22) Filed: Apr. 17, 2019

(65) Prior Publication Data

US 2020/0078441 A1 Mar. 12, 2020

Related U.S. Application Data

(60) Provisional application No. 62/658,696, filed on Apr. 17, 2018.

(51) Int. Cl.
*A61K 38/17* (2006.01)
*A61P 35/00* (2006.01)

(52) U.S. Cl.
CPC .......... *A61K 38/1709* (2013.01); *A61P 35/00* (2018.01)

(58) Field of Classification Search
CPC ..... A61K 38/1709; A61K 38/10; A61P 35/00; C07K 7/08
See application file for complete search history.

(56) References Cited

U.S. PATENT DOCUMENTS

2015/0159131 A1* 6/2015 MacNicol .............. C07K 16/18
435/6.12

OTHER PUBLICATIONS

Chen et al. Musashi-1 promotes stress-induced tumor progression through recruitment of AGO2. Theranostics 10(1): 201-217, Jan. 1, 2020.*
Chen et al. Abstract LB-079: The interaction of MSI1 and AGO2 promotes glioblastoma multiforme progression under environmental stress. AACR Annual Meeting 2018; Apr. 14-18, 2018.*

* cited by examiner

*Primary Examiner* — Alana Harris Dent
(74) *Attorney, Agent, or Firm* — Birch, Stewart, Kolasch & Birch, LLP

(57) ABSTRACT

The disclosure of the preset invention relates to a new method for preventing or treating tumor progression or tumor recurrence comprising administering to a subject in need thereof a therapeutically effective amount of an agent disrupting Musashi-1 (MSI1)/Argonaute 2 (AGO2) interaction. A composition or pharmaceutical composition for preventing or treating tumor progression or tumor recurrence is also provided, which comprises an agent disrupting Musashi-1 (MSI1)/Argonaute 2 (AGO2) interaction.

2 Claims, 16 Drawing Sheets
Specification includes a Sequence Listing.

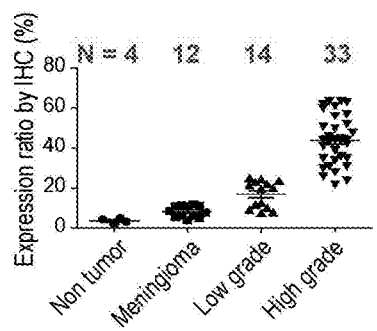
Supplementary Figure 1A
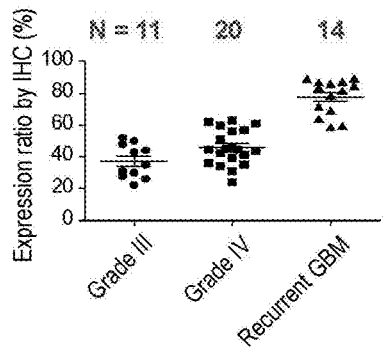
Supplementary Figure 1B
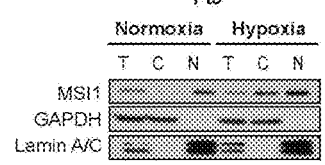
Supplementary Figure 1C
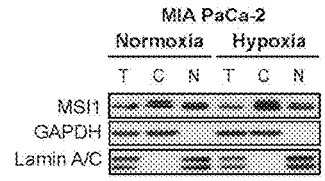
Supplementary Figure 1D
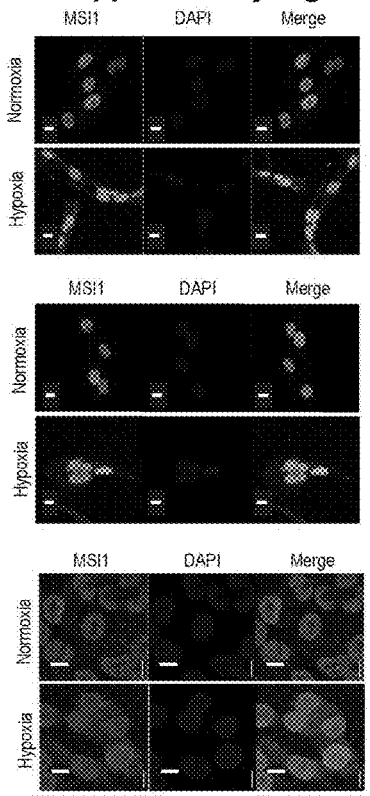
Supplementary Figure 1
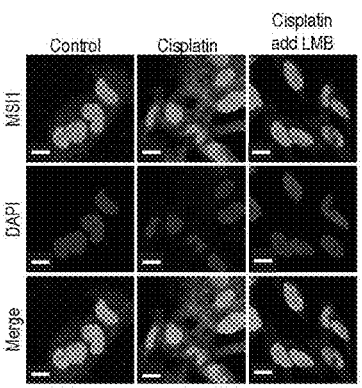
Supplementary Figure 1E
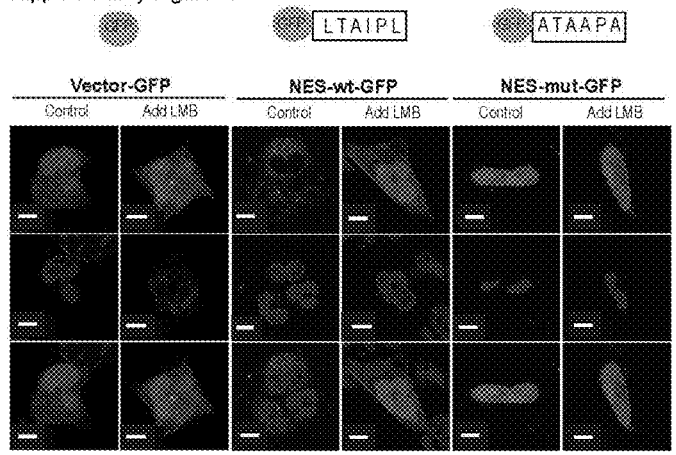
Supplementary Figure 1F
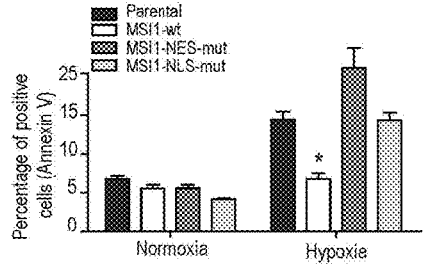
Supplementary Figure 1G
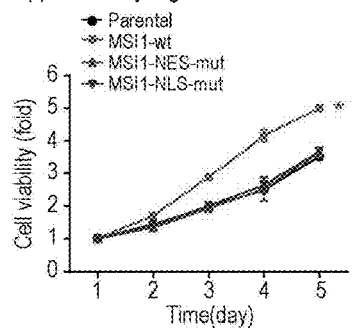
Supplementary Figure 1H
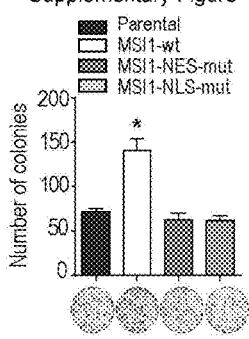
Supplementary Figure 1I

Supplementary Figure 2

Supplementary Figure 2A

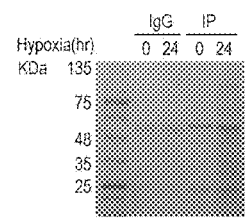

Supplementary Figure 2C

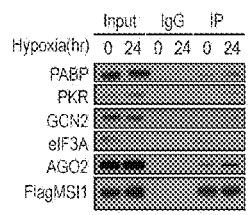

Supplementary Figure 2D

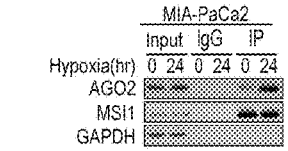

Supplementary Figure 2E

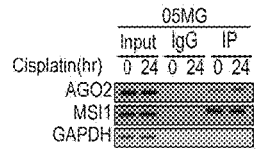

Supplementary Figure 2B

| Protein ID | Protein Name | Gene Symbol |
|---|---|---|
| P11940 | Polyadenylate-binding protein 1 | PABPC1 |
| P19525 | Interferon-induced, double-stranded RNA-activated protein kinase | PKR |
| Q9P2K8 | eIF-2-alpha kinase GCN2 | GCN2 |
| Q14152 | Eukaryotic translation initiation factor 3 subunit A | EIF3A |
| Q9UKV8 | Protein argonaute-2 | AGO2 |

Supplementary Figure 2F

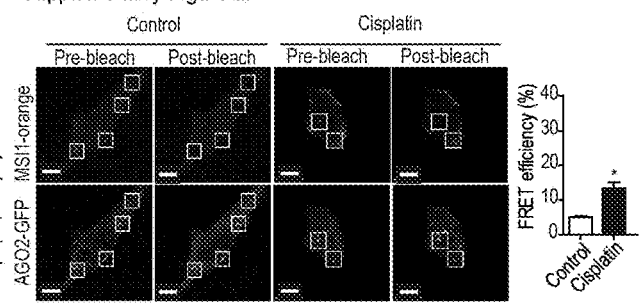

Supplementary Figure 2G

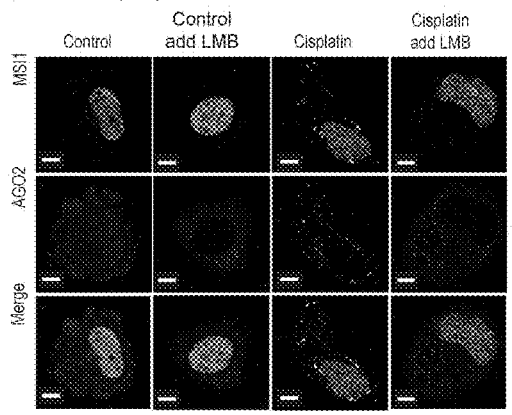

Supplementary Figure 2H

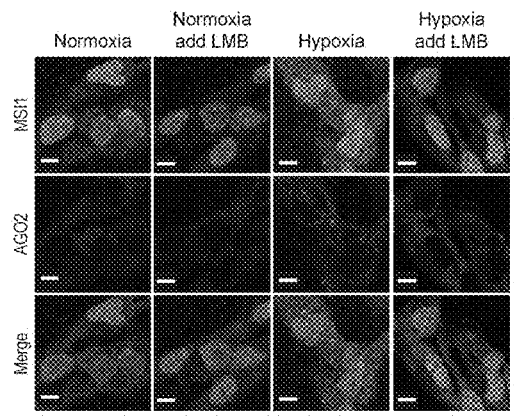

Supplementary Figure 2I

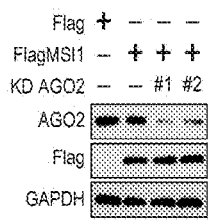

Supplementary Figure 2J

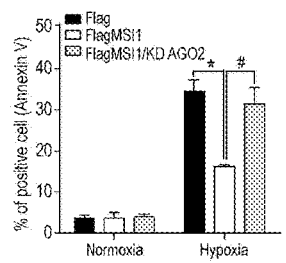

Supplementary Figure 3
Supplementary Figure 3A
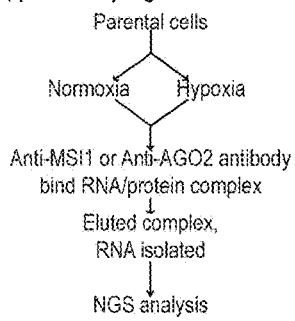
Supplementary Figure 3B
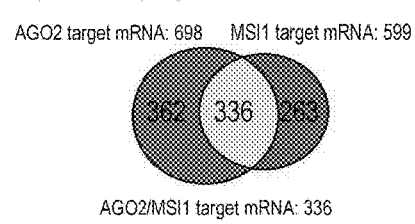
AGO2/MSI1 target mRNA: 336
Supplementary Figure 3C
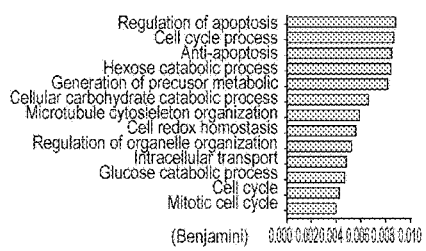
Supplementary Figure 3D
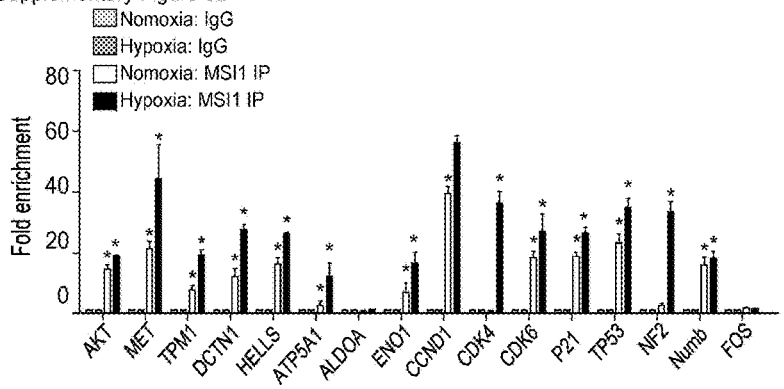
Supplementary Figure 3F
FlagMSI1
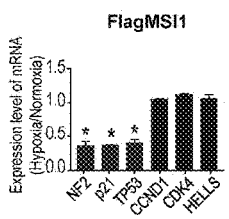
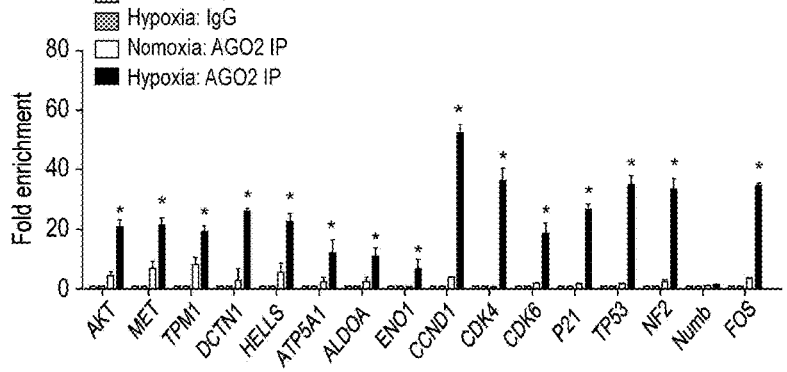
FlagMSI1/KD AGO2
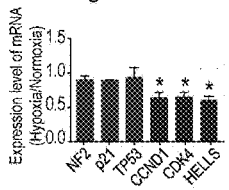
Supplementary Figure 3E
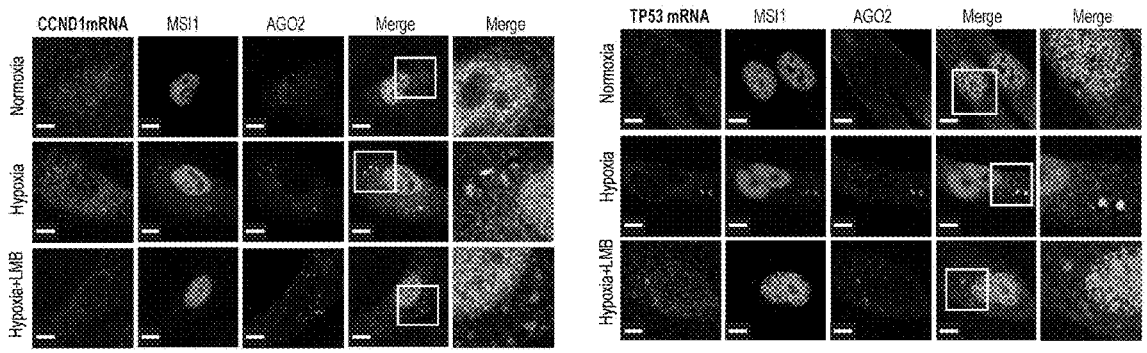

Supplementary Figure 4
Supplementary Figure 4A
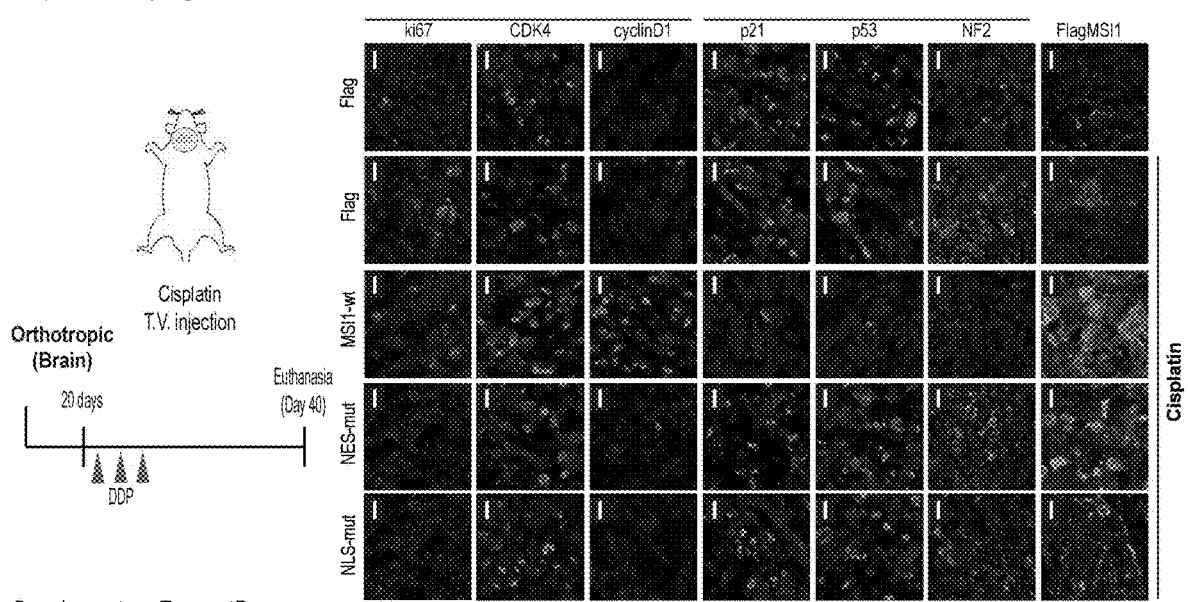
Supplementary Figure 4B
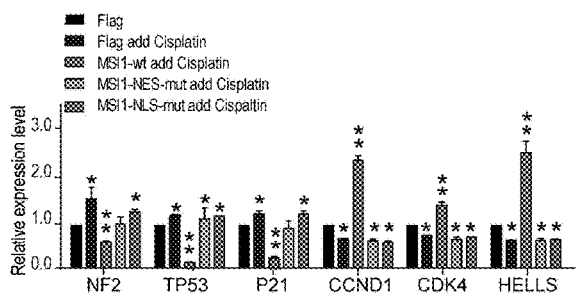
Supplementary Figure 4C
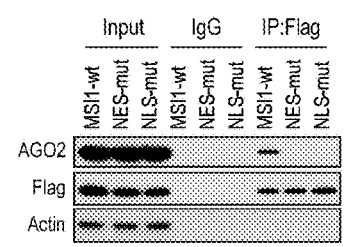

Supplementary Figure 5
Supplementary Figure 5A
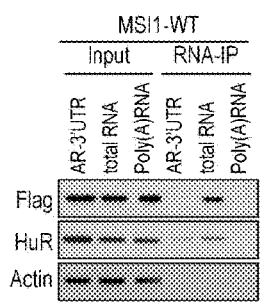
Supplementary Figure 5B
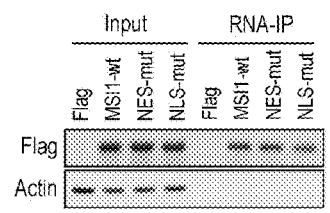

Supplementary Figure 6
Supplementary Figure 6A
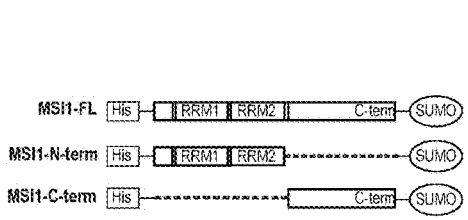
Supplementary Figure 6B
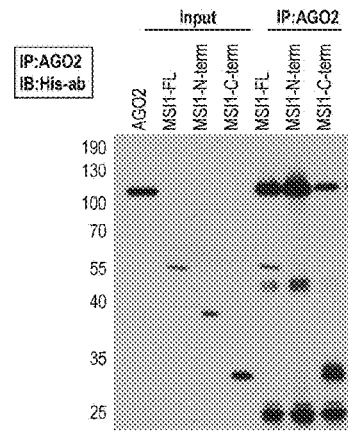
Supplementary Figure 6C
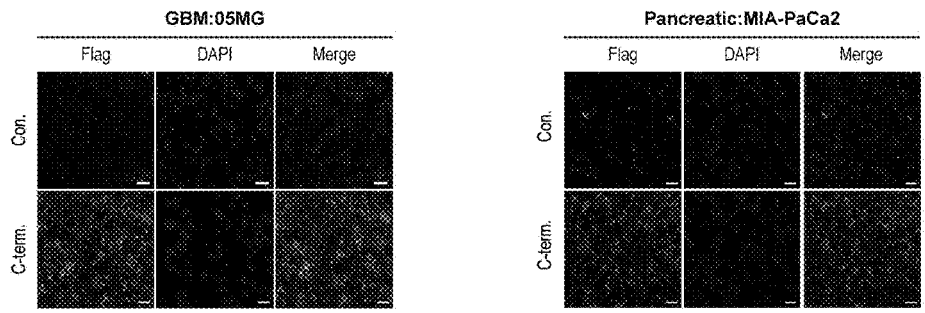
Supplementary Figure 6D
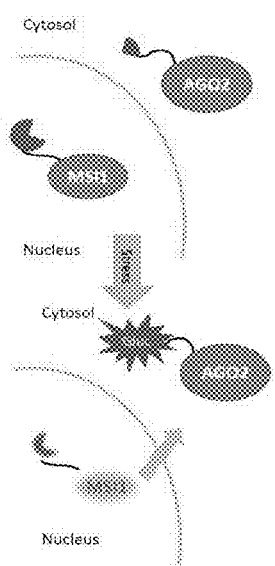
Supplementary Figure 6E
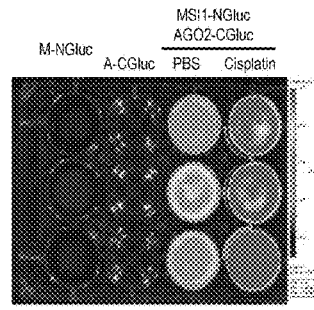
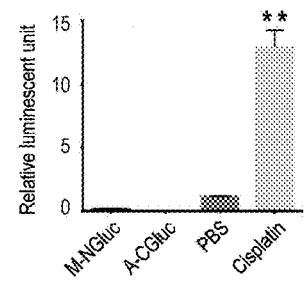
Supplementary Figure 6F
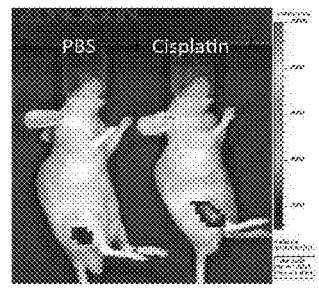
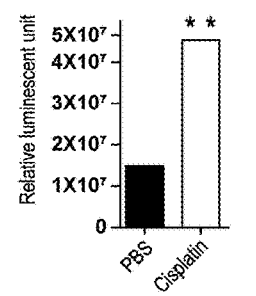

Supplementary Figure 7
Supplementary Figure 7A
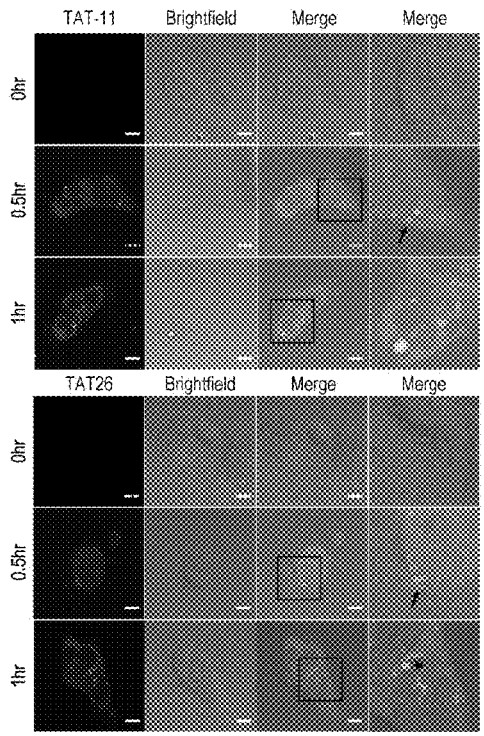
Supplementary Figure 7B
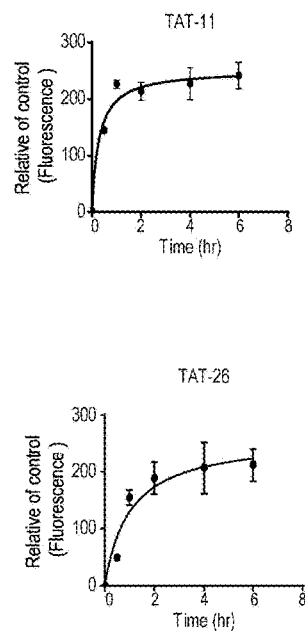
Supplementary Figure 7C
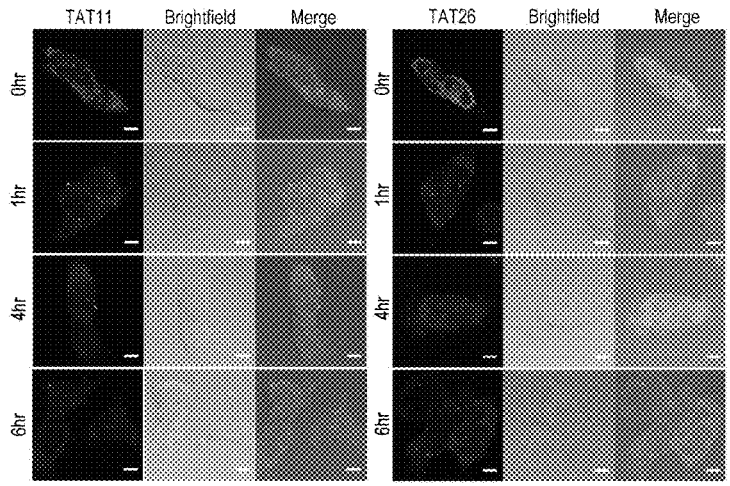
Supplementary Figure 7D
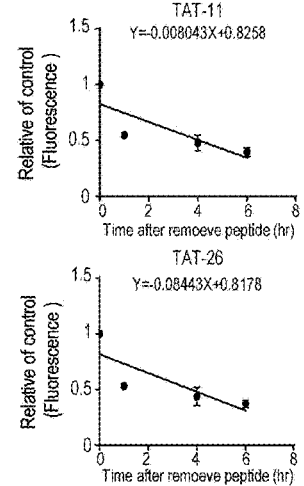

Supplementary Figure 8
Supplementary Figure 8A
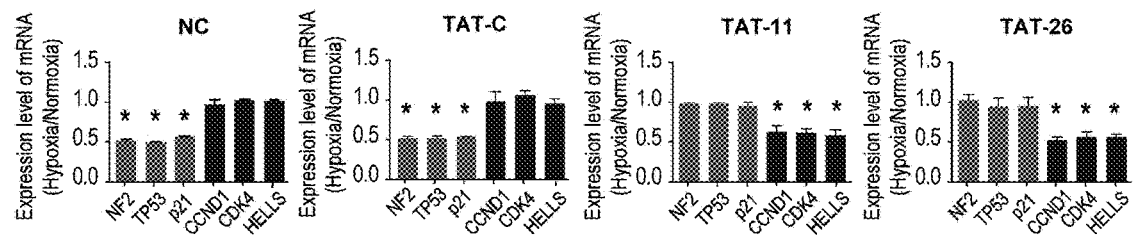
Supplementary Figure 8B
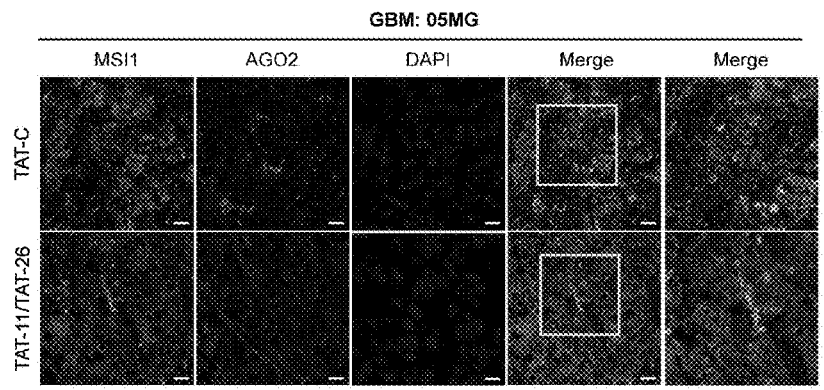
Supplementary Figure 8C
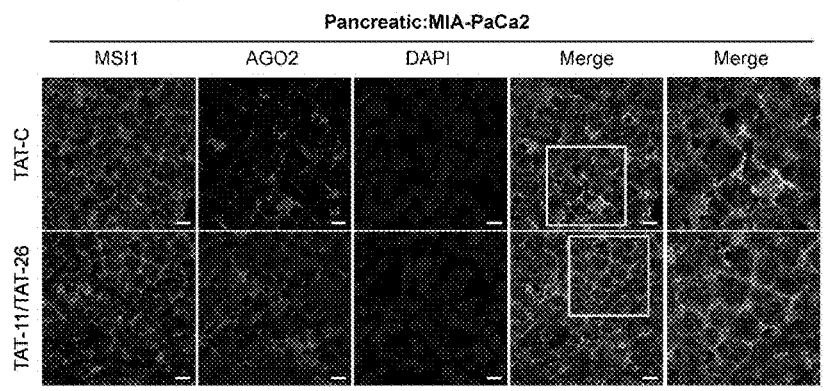

Figure 9
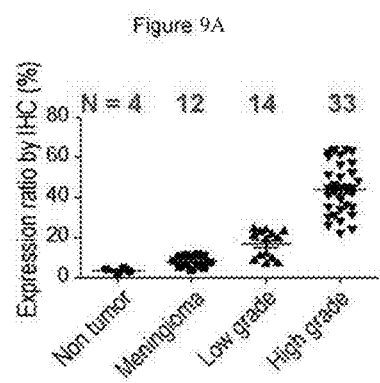
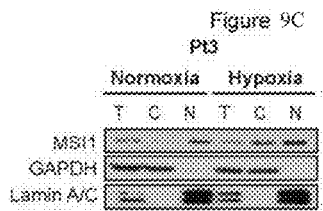
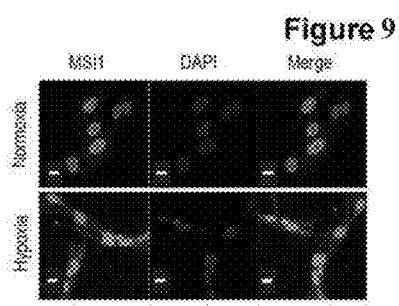
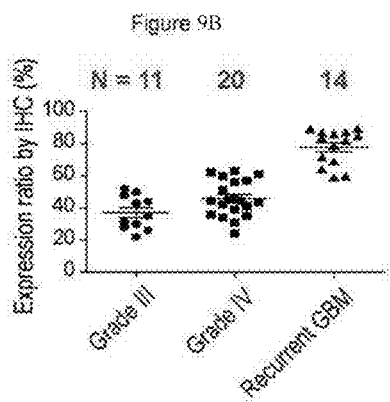
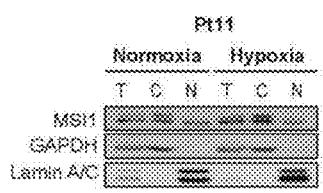
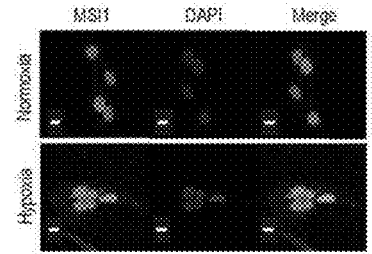
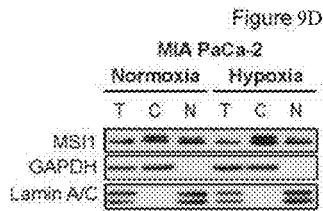
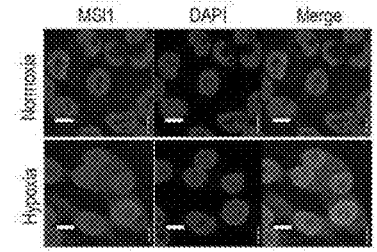
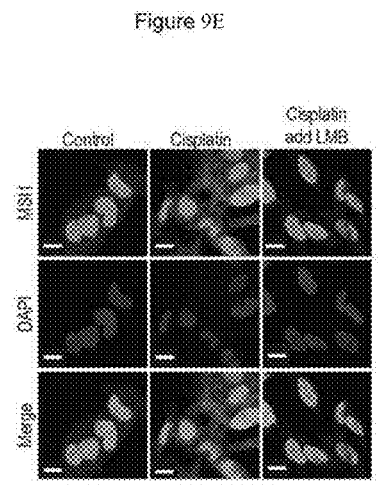
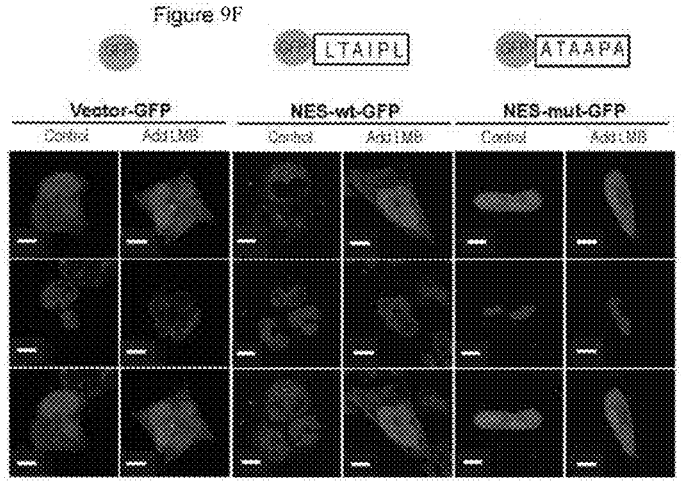
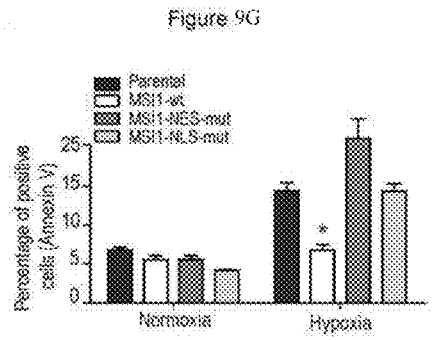
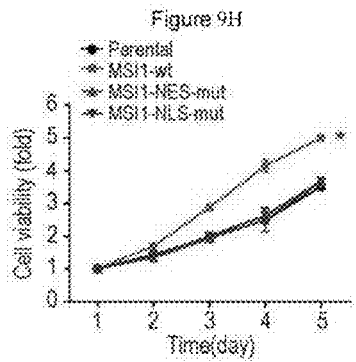
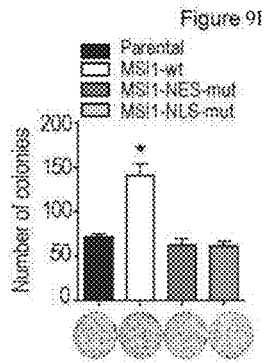

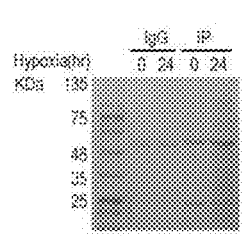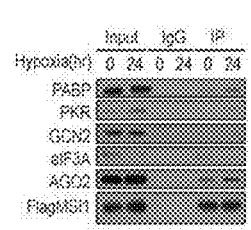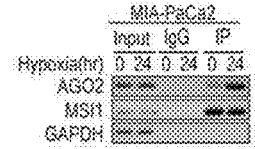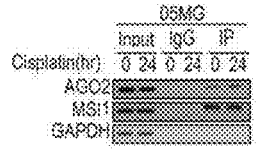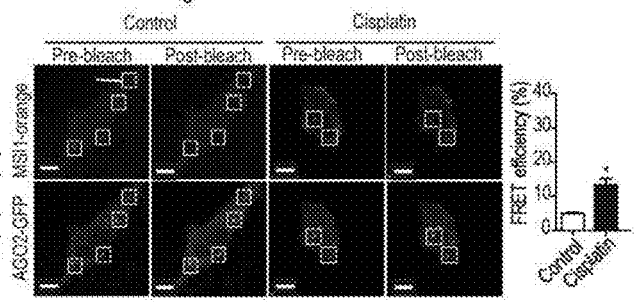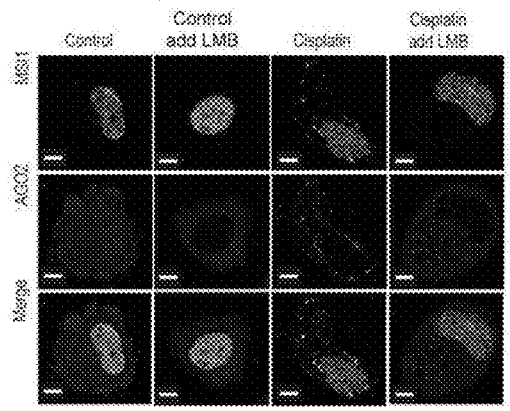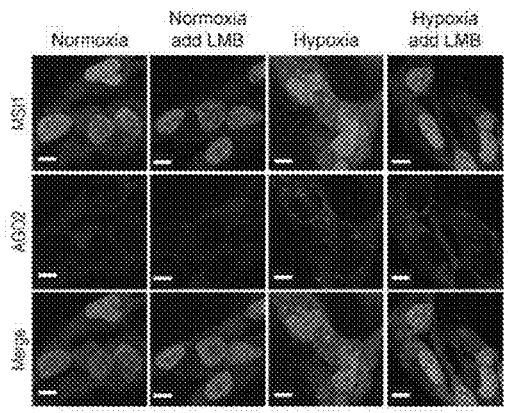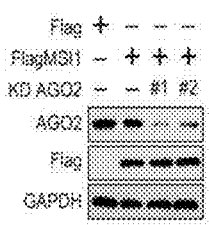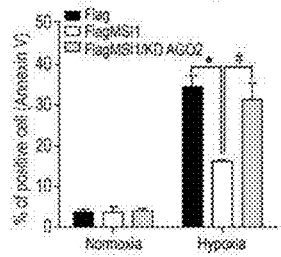
Figure 10

Figure 11
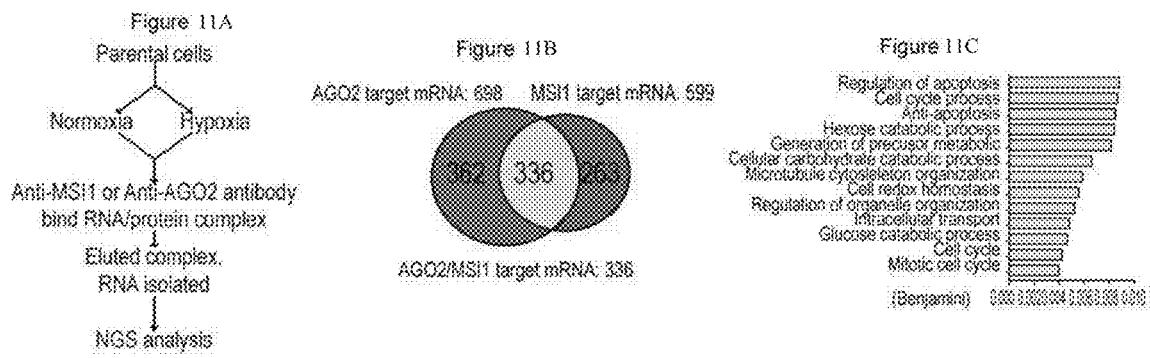
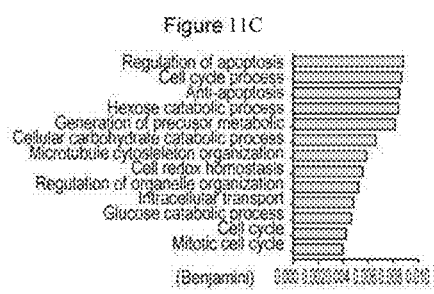
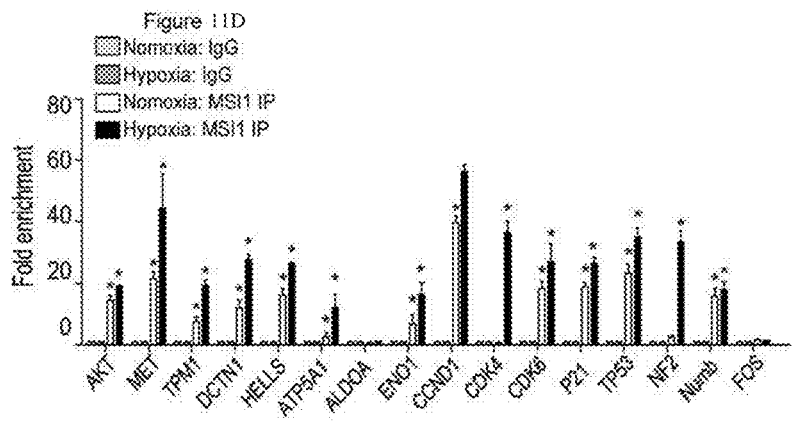
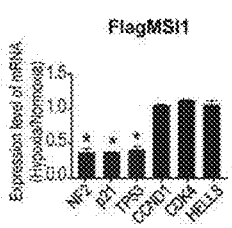
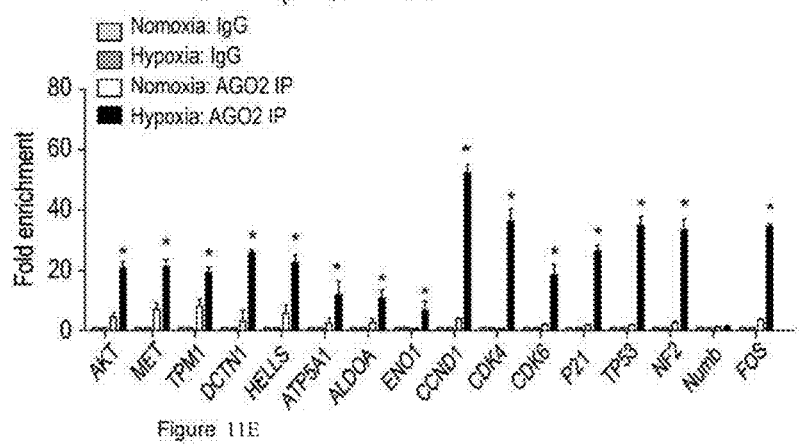
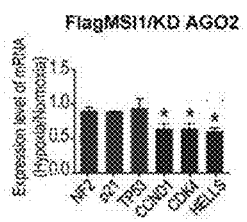
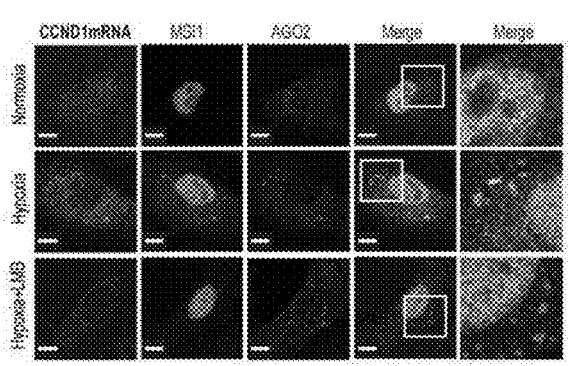
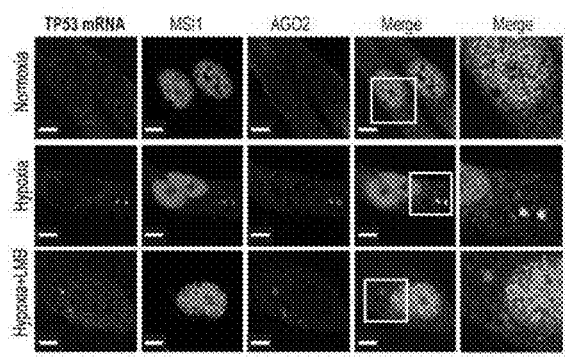

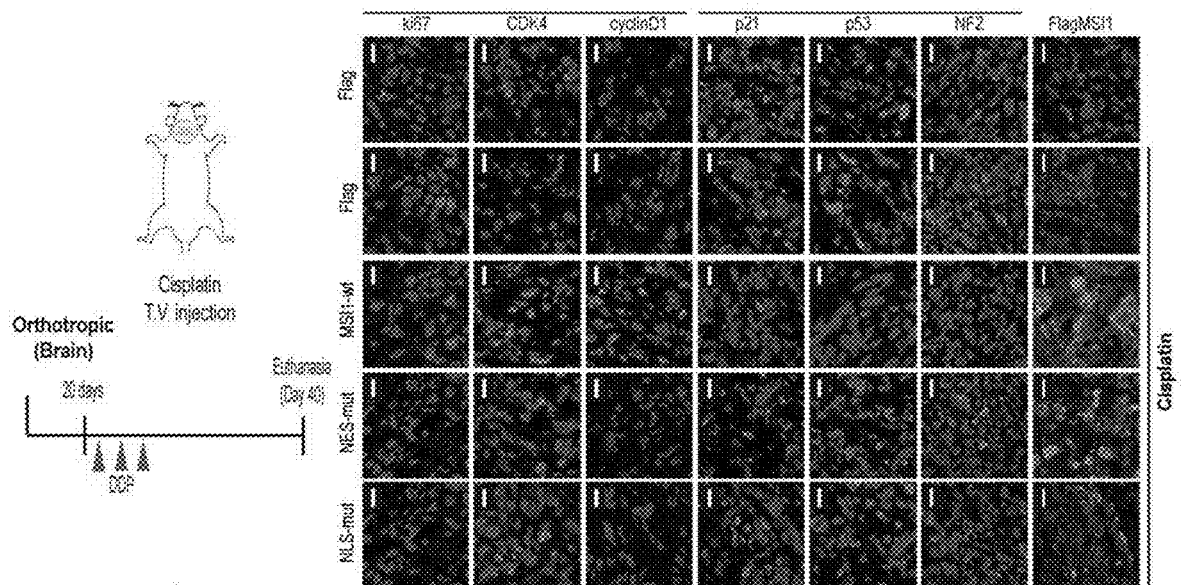
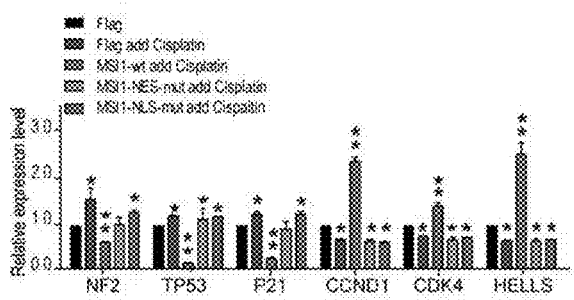
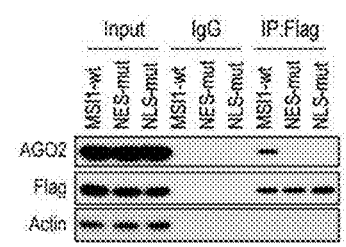
Figure 12

Figure 13
Figure 13A
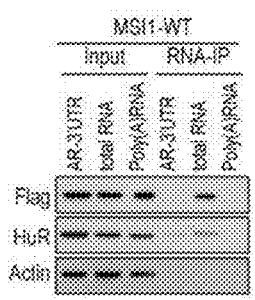
Figure 13B
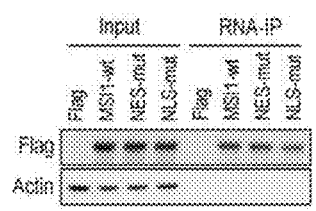

Figure 14
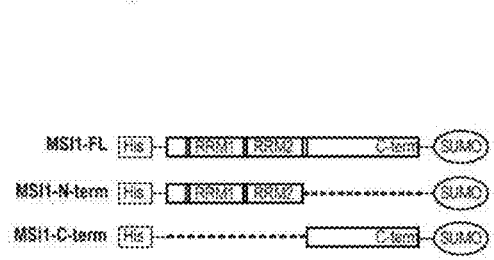
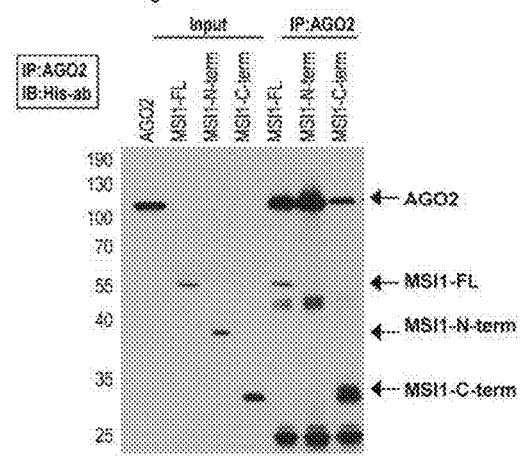
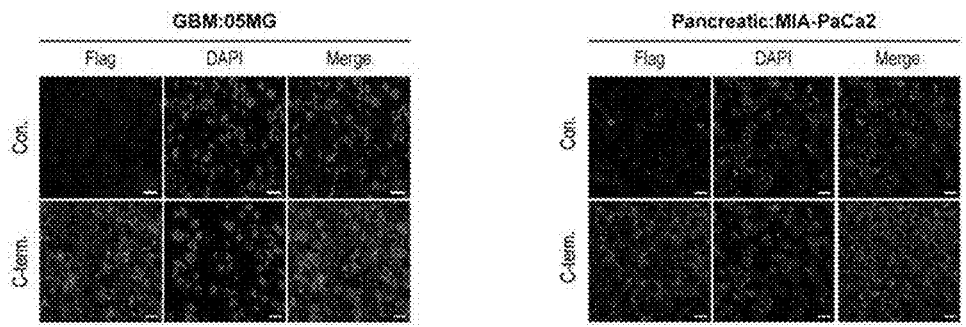
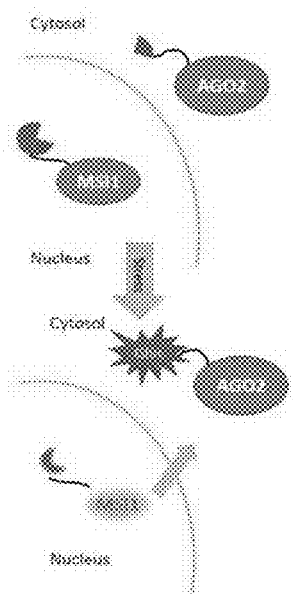
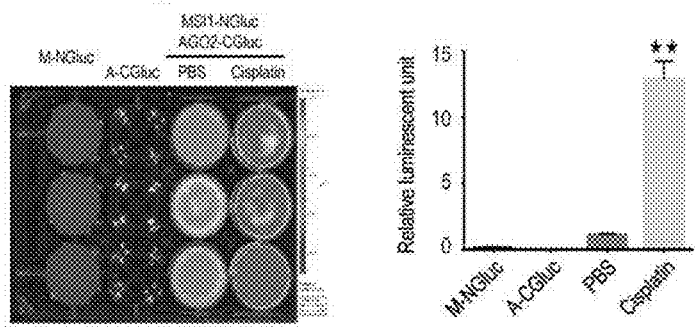
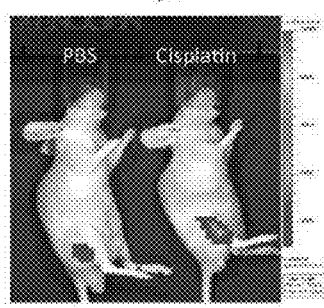
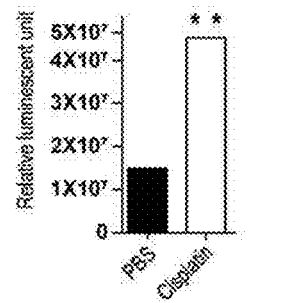

Figure 15
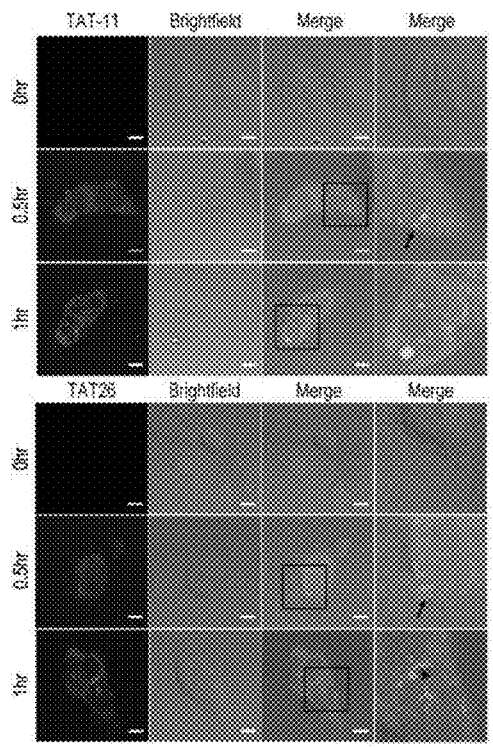
Figure 15A
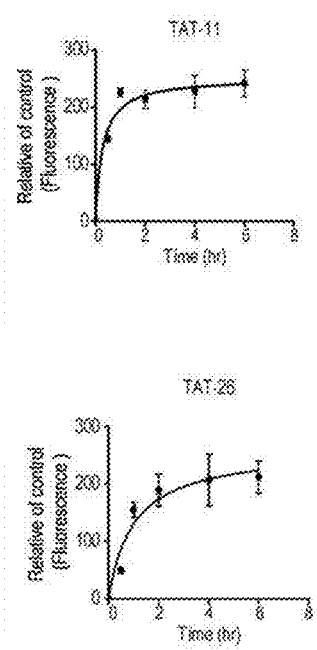
Figure 15B
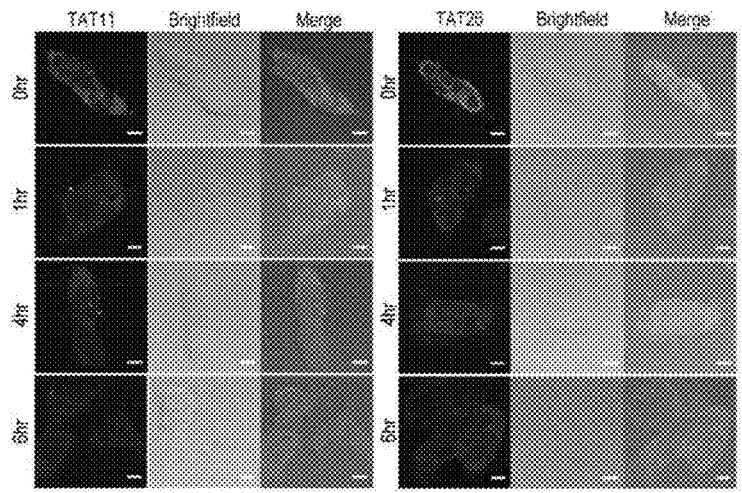
Figure 15C
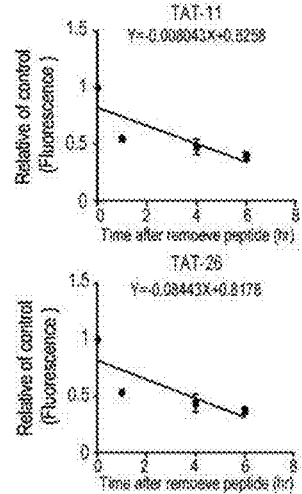
Figure 15D

Figure 16
Figure 16A
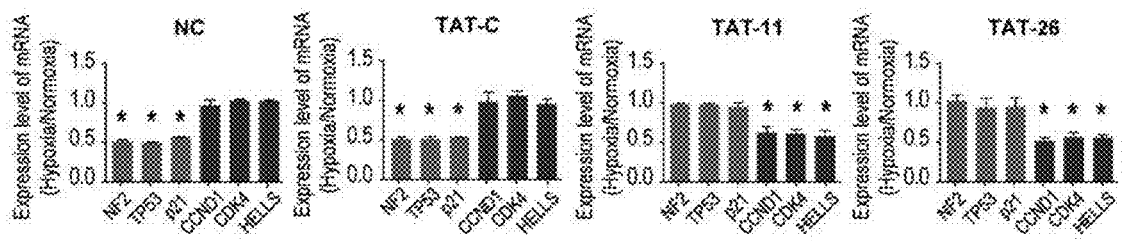
Figure 16B
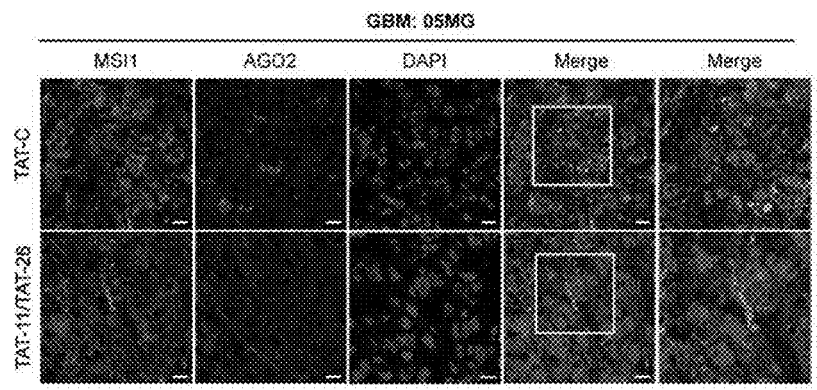
Figure 16C
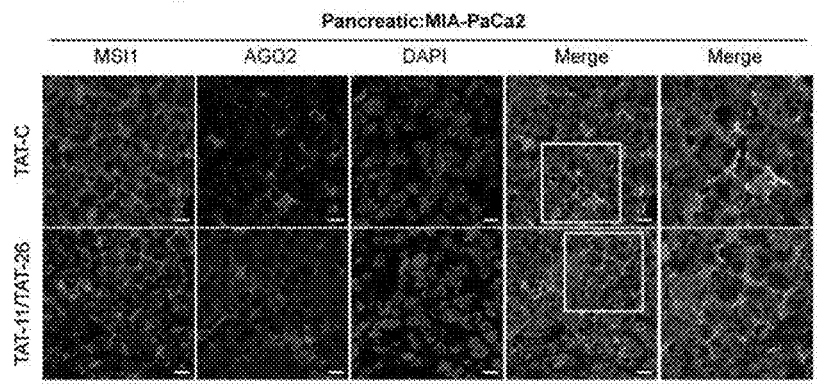

METHOD FOR BLOCKING STRESS-INDUCED TUMOR PROGRESSION

FIELD OF THE INVENTION

The present invention relates to a new method for blocking stress-induced tumor progression.

REFERENCE TO SEQUENCE LISTING SUBMITTED VIA EFS-WEB

This application includes an electronically submitted sequence listing in .txt format. The .txt file contains a sequence listing entitled "2019-11-12_SequenceListing_5992-0266PUS1.txt" created on Nov. 8, 2019 and is 59,450 bytes in size. The sequence listing contained in this .txt file is part of the specification and is hereby incorporated by reference herein in its entirety.

BACKGROUND OF THE INVENTION

RNA binding proteins (RBPs) play crucial roles in various cellular processes by regulating the post-transcriptional control of their mRNA targets, such as microRNA biogenesis, RNA localization, translation and stability[1-6]. The RBP family of Musashi proteins, composed of Musashi-1 (MSI1) and Musashi-2, exerts an essential control over multiple cellular functions[7], such as the maintenance of self-renewal and pluripotency state in stem cells[8]. Dysfunctions in the expression or activity of this family have been shown to lead to tumorigenesis of glioblastoma (GBM) or pancreatic ductal adenocarcinoma (PDAC)[9,10]. MSI1 was recently reported to directly target the 3' untranslated region (3' UTR) of its target mRNAs to suppress their translation[11]. MSI1 also cooperates with LIN28 RBP to inhibit the post-transcriptional biogenesis of miRNAs in embryonic stem cells[12]. Increasing evidence points to the role of MSI1 in tumorigenesis and cancer proliferation[13]. High level of MSI1 expression has been observed in several tumor tissues[9,10,14-17], and is associated with poor survival of grade III/IV gliomas patients[18]. Although these studies suggest the involvement of MSI1 in malignancy, its functional roles and molecular mechanisms underlying carcinomatous recurrence remain largely unknown.

The Argonaute (AGO) proteins, also part of the RBP family, play a central role in RNA silencing processes by mediating the decay and translational inhibition of their targets[19-21]. In many carcinomas, AGO2 is found to be ectopically overexpressed[19], and several studies indicated that AGO2 could directly be involved in cancers progression by interacting with oncogenic factors like EGFR[22]. AGO2 also responds to stress stimulation by remodeling its interactions with target mRNAs and by modulating their post-transcriptional control[23]. By remodeling its occupancy on the 3' UTR and coding sequence (CDS) region of target mRNAs, AGO2 adjusts the translation rate of specific group of genes[23]. However, the mechanisms by which AGO2 coordinates the translation rate of specific targets in response to stresses in malignant progression are still unclear.

SUMMARY OF THE INVENTION

It is unexpectedly found in the present invention that in response to stress, Musashi-1(MSI1) translocates into the cytosol where it recruits Argonaute 2 (AGO2) and post-transcriptionally regulates the expression of specific target mRNAs and the binding of MSI1/AGO2 to the 3' UTR of target mRNAs enhances their degradation whereas binding to CDS prevents their rapid degradation. By coordinating the two mechanisms, MSI1/AGO2 complex enhances tumor proliferation and ensures cancer cell survival under hypoxia or chemodrug treatment. It is confirmed in the examples that the disruption of the MSI1/AGO2 interaction by MSI1 decoy peptides decreased stress-induced tumorigenicity. Accordingly, it is potential to use a small peptide as a therapeutic sensitizer for preventing or treating a tumor progression or a tumor recurrence.

In one aspect, the invention provides a method for preventing or treating a tumor progression or a tumor recurrence, comprising administering to a subject in need thereof a therapeutically effective amount of an agent disrupting Musashi-1 (MSI1)/Argonaute 2 (AGO2) interaction.

In one embodiment of the invention, the agent disrupting MSI1/AGO2 interaction is a MSI1 decoy peptide.

In one example of the invention, the agent disrupting MSI1/AGO2 interaction is an antibody, a binding protein, a peptide or a molecule which is capable of binding to AGO2.

In one particular example of the invention, the agent disrupting MSI1/AGO2 interaction is a peptide having the amino acid sequence of YQFPEFRVERTPLPS or HSLGG-PLIATAFTNG.

BRIEF DESCRIPTION OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. It should be understood, however, that the invention is not limited to this embodiment.

FIG. 1 shows the translocation of MSI1 into the cytosol correlates with tumor progression and cell proliferation under stress conditions. FIG. 1A shows the IHC staining for MSI1 in primary (n=67) and recurrent (n=32) GBM. Magnifying power: 200× (top) and 600× (bottom). Quantitation of cells expressing cytoplasmic or nuclear MSI1 is shown in the bar graph on the right. FIG. 1B 05 MG cells pre-treated with or without nuclear export inhibitor leptomycinB (LMB) (10 ng/mL, 2 h) under normoxia or hypoxia conditions for 24 hr were subjected to anti-MSI1 (green) immunostaining and DAPI (blue) nuclear counterstaining. Images were acquired from Carl Zeiss confocal microscope system. The intensity of green fluorescence in nuclear and cytosol was quantified and shown as relative percentage in the graph at the right. FIG. 1C shows the total protein (T), nuclear (N), and cytoplasmic (C) fractionations of 05 MG cells under normoxia or hypoxia (24 hr) in the presence or absence of LMB (10 ng/mL) were subjected to immunoblotting with MSI1, Lamin A/C (nuclear internal control) and GAPDH (cytosolic control) antibodies. FIG. 1D provides a schematic showing the mutation sites in the NLS (orange) and NES (red) of human MSI1. All constructs were sub-cloned into p-3×Flag-Myc-CMV expression vector. FIG. 1E shows that 05 MG cells stably transfected with the Flag-tagged MSI1-wt, MSI1-NES-mut, or MSI1-NLS-mut were subjected to normoxia or hypoxia for 24 hr. and then immunostained with anti-Flag antibody (green). Images were acquired from Carl Zeiss confocal microscope system, and the quantification of fluorescent intensity in the nuclear and cytosolic compartments was shown as relative percentage in the graph at the left. FIG. 1F shows that the null mice were subcutaneously transplanted with 05 MG/MSI1-wt, 05 MG/MSI1-NES-mut, 05 MG/MSI1-NLS-mut, or 05 MG-parental cells. Tumor size was measure with a caliper at the indicated time points. The 05 MG/MSI1-NES-mut and 05 MG/MSI1-NLS-mut tumors showed similar growth curves as the parental cells, while the 05 MG/MSI1-wt tumor grew much more rapidly (N=6. P<0.05 vs. parental cells). FIG. 1G shows that xenograft tumors were excised (top), and tumor tissues were subjected to immunostaining to evaluate the expression and distribution of Flag-tagged MSI1-wt, MSI1-NES-mut, and MSI1-NLS-mut proteins (bottom). Images were acquired from Carl Zeiss confocal microscope system. FIG. 1H shows that tumor tissue were harvested and homogenized. Whole-tumor lysates were subjected to Western blot analysis. Data represent the mean±S.D. of three independent experiments performed in triplicate. FIG. 1I A schematic depicting the experimental design for subcutaneously transplanted and orthotropic transplanted. FIG. 1J-K Null mice were subcutaneously transplanted with 05 MG/Flag-control, 05 MG/MSI1-wt, 05 MG/MSI1-NES-mut, or 05 MG/MSI1-NLS-mut cells. Two days after the tumor size reached 50 mm$^3$, mice started DDP (20 mg/kg) or PBS administered via tail-vein injection for total 3 times with 2-day interval. The tumor size was measured with a caliper at the indicated time points. Xenograft tumors were excised 40 days after DDP treatment (N=6, P<0.05). FIG. 1L shows that SCID mice were orthotopically transplanted with 05 MG/Flag-control, 05 MG/MSI1-wt, 05 MG/MSI1-NES-mut, or 05 MG/MSI1-NLS-mut GFP cells. Twenty days after transplantation, mice were administered DDP (20 mg/kg) or PBS via tail-vein injection every 2 days for 3 times. Xenograft tumors were excised 200 days after DDP treatment. Representative images of GFP-positive tumors (N=6, **P<0.05).

FIG. 2 shows that MSI1 interacts with AGO2 to mediate the stability of downstream mRNA targets. FIG. 2A provides a schematic illustrating the procedure for identifying hypoxia-induced binding partners of MSI1. FIG. 2B shows that co-immunoprecipitation of endogenous AGO2 with MSI1 antibody in the cytosol or nuclear fraction of 05 MG cells under hypoxia for indicated period of time. FIG. 2C shows the in vitro binding assay of purified baculovirus-expressed His-tagged AGO2 and Flag-tagged MSI1 proteins. FIG. 2D shows that 05 MG cells-expressing FRET pairs of MSI1-orange and AGO2-GFP were bleached at the region of interest (ROI) indicated by yellow boxes. Unbleached controls (pre-bleach) were also shown in parallel. Left, representative images of MSI1 (orange) and AGO2 (green) before and after photobleaching experiments. Right, quantification of FRET photobleaching experiments was performed by calculating FRET efficiencies for the FRET pairs MSI1 (orange)-AGO2 (green). FIG. 2E shows that 05 MG/Flag-control, 05 MG/Flat-MSI1-wt, and 05 MG/MSI1-wt with AGO2-knockdown (Flag-MSI1/shAGO2) were subjected to an MTT viability assay. The relative fold change of the numbers of viable cells in each day was presented in the graph. FIG. 2F shows that 05 MG/Flag-control, 05 MG/MSI1-wt and 05 MG/MSI1-wt/shAGO2 cells were subjected to colony formation assay for 5 days, and the numbers of colony were quantitated by ImageJ software. FIG. 2G shows that immunocompromised mice were subcutaneously transplanted with 05 MG/MSI1-wt and 05 MG/MSI1-wt/shAGO2 cells. Tumor size was then monitored for 22 days (N=6. *P<0.05 vs. 05 MG/MSI1-wt cells). FIG. 2H shows that parental and MSI1- or AGO2-knockdown cells under normoxia and hypoxia conditions were subjected to a gene expression microarray. Bioinformatics analysis of the microarray data with focus on the 336 common targets of MSI1 and AGO2 identified by RIP-Seq showed the hierarchical clustering these common targets in the heat map. The red and green colors respectively indicate the differentially up or downregulated genes. Each group were done in three distinct biological replicates and the means signals were transformed to the log 2 scale. FIG. 2I shows that actinomycin D (Act. D, 5 µg/ml) was added to parental and MSI1- or AGO2-knockdown cells for the indicated times. We compared the half-life distribution of TP53, NF2, CDKN1A, CCND1, CDK4 and HELLS mRNA levels between parental and MSI1- or AGO2-knockdown cells. The RNA expression levels are shown below each the respective box-plots. FIG. 2J and FIG. 2K show that parential and MSI1- or AGO2-knockdown 05 MG cells, as well as MSI1-wt, MSI1-NES-mut, and MSI1-NLS-mut transfected 05 MG cells were treated with normoxia or hypoxia conditions for 24 hours. Purified RNA was subjected to RT-PCR with primers specific to TP53, NF2, CDKN1A, CCND1, CDK4 and HELLS. The mRNA levels under hypoxia were normalized by that under normoxia and shown as relative value in the chart.

FIG. 3 shows the differential regulation of mRNAs by MSI1/AGO2 complex under hypoxia. FIG. 3A shows endogenous MSI1 or AGO2 was immunoprecipitated in MSI1 or AGO2 knockdown cell with anti-MSI1 or anti-AGO2 antibody. Western blot of the immunoprecipitation (IP) confirmed the MSI1/AGO2 interaction in hypoxia-treated parental cells but not in MSI1 or AGO2 knockdown cells (top). Total RNAs isolated from IP were subjected to NF2, TP53, CCND1, and HELLS mRNA quantitation by using qPCR with specific primer. Quantification of mRNA expression levels experiments by normalization with IgG control. Data represent the mean±S.D. of three independent experiments performed in triplicate (*P<0.05 vs IgG signal). FIG. 3B shows that nuclear and cytosolic fractions of 05 MG/MSI1-wt, 05 MG/MSI1-NES-mut, and 05 MG/MSI1-NLS-mut cells were subjected to the immunoprecipitation with Flag antibodies to pull down the complexes interacting with Flag-tagged MSI1. Left, immunoprecipitates were subjected to Western blot to assess the binding between AGO2 and full-length or mutated MSI1. Right, total RNAs isolated from the immunoprecipitated complexes were analyzed by qRT-PCR for NF2, TP53, CCND1, and HELLS mRNA levels. Fold change in mRNA levels was normalized to IgG-precipitated controls. FIG. 3C provides the results of the RNA-ChIP analysis of the binding regions of MSI1 and AOG2 on the target mRNAs. RIP were performed with anti-MSI1 or anti-AGO2 followed by RNA fragmentation and qPCR of NF2, TP53, CCND1, and HELLS coding sequence (CDS) and 3' UTR. MSI1 or AGO2 palindromic-binding sequence exists within the peak. Quantification of fold changes of the signals were normalized to IgG-precipitated controls. This experiments were done in three distinct biological replicates. FIG. 3D provides a schematic illustrating the fate of mRNA determined by the MSI1-AGO2 complex. MSI1-AGO2 regulates RNA stability of specific RNAs to sustain tumor growth under stress in two ways: 1) MSI1-AGO2 facilitates tumor suppressor gene mRNA decay to prevent stress-induced cell death (likely through the conventional UTR binding followed by post-transcriptional repression) and 2) MSI1-AGO2 stabilizes and protects mRNA of cell cycle genes to promote prompt translation upon stress removal (likely through the CDS binding and subsequent aggregation in stress granules).

FIG. 4 shows that the C-terminal of MSI1 is critical for AGO2 binding and cell viability. FIG. 4A provides a schematic illustrating the full-length and C-terminal (C-term)

fragment of human MSI1. The construct of MSI1 C-term was sub-cloned into p-3×Flag-Myc-CMV expression vector. FIG. 4B shows that the cells transient transfected with Flag-control or Flag-tagged MSI1 C-term (Flag-C-term) were subjected to co-immunoprecipitation assay for endogenous AGO2 and MSI1 protein-protein interaction. Transfection of the Flag-C-term blocked hypoxia-induced MSI1/AGO2 binding. FIG. 4C shows that Cells transfected with Flag-control or Flag-C-term were analyzed under confocal microscopy for the subcellular co-localization of MSI1 (Red) and AGO2 (Green). FIG. 4D shows that flag-control and Flag-C-term transfected cells were subjected to an RNA-ChIP assay using anti-MSI1 or anti-AGO2 antibodies, followed by RNA fragmentation and qRT-PCR analysis to determine the fold change enrichment of the coding sequence (CDS) and 3' UTR of the NF2, TP53, CCND1 and HELLS mRNAs. Quantification of the fold changes of binding signals was performed by normalizing IP signals to IgG-precipitated controls. The peaks indicated MSI1 or AGO2 palindromic-binding sequence. Flag-C-term blocked the binding of AGO2 but not MSI1 to target sequence in mRNAs. FIG. 4E shows that flag-control and Flag-C-term transfected cells were subjected to normoxia or hypoxia for 24 hr. Purified total RNA was subjected to RT-PCR using primers specific for NF2, TP53, CDKN1A, CCND1, CDK4, and HELLS. The mRNA levels under hypoxia were normalized with that under normoxia and presented as relative fold changes in the chart. FIG. 4F shows that 05 MG cells transiently transfected with Flag control or Flag-tagged MSI1 C-term were subjected to an MTT viability assay. The relative fold change of the number of viable cells in each day was presented in the graph. FIG. 4G shows that flag-control and Flag-C-term transfected cells were subjected to colony formation assay for 5 days and quantitated by ImageJ software. FIG. 4H shows that the percentage of apoptotic cells of Flag-control and Flag-C-term transfected cells was determined by external Annexin-V under normoxiac and hypoxic conditions. FIG. 4I provides a schematic presentation showing the design of animal experiment with in vivo delivery of Flag-C-term (10 µg using in vivo-jetPEI in vivo nucleic acid delivery reagent). Xenograft tumor size was monitored from day 2 after injection of Flag-control or Flag-C-term. FIG. 4J shows that immunocompromised mice were subcutaneously transplanted with 05 MG/Flag-MSI1 stable cells. Two days after tumor size reached 50 mm$^3$, mice were intratumorally injected with 10 µg of Flag-control or Flag-C-term for 3 rounds with 2-day intervals. Tumor size was then monitored for 22 days. The expression of MIS1-C-term in the xenograft tumor tissue was assessed by Western blot. FIG. 4K shows that immunocompromised mice were subcutaneously transplanted with MIA-PaCa2 cells. Two days after tumor size reached 50 mm$^3$, mice were intratumorally injected with Flag-control or Flag-C-term for 3 rounds with 2 days interval. Tumor size was then monitored for 22 days. The expression of MIS1-C-term in the xenograft tumor tissue was assessed by Western blot.

FIG. 5 shows decoy peptides mimicking the MSI1/AGO2 interaction regions from MSI1-C-term bounds to AGO2. FIG. 5A shows that recombinant AGO2 proteins were incubated with nitrocellulose membrane peptide array dotted with 27 peptide fragments designed from the C-terminus of MSI1. The array revealed two potential interacting peptides with recombinant AGO2. FIG. 5B shows that cells respectively treated with 10 µM of the two decoy peptides (TAT-11 and TAT-26) or peptide control (TAT-C) were subjected to co-IP immunoblot to demonstrate the efficacy of the two peptides on blocking the MSI1/AGO2 interaction under hypoxic condition. FIG. 5C shows in vitro *Gaussia* luciferase assay to detect of MSI1 and AGO2 protein-protein interaction in the presence of 10 µM TAT-11 and TAT-26. FIG. 5D and FIG. 5E shows the structures of the AGO2-peptide (TAT-11 or TAT-26) complex predicted by a molecular docking website (http://galaxy.seoklab.org/index.html). AGO2 was showed in four colors illustrating different functional domains, and peptides were showed in orange (TAT-11) and red (TAT-26). The relative orientation of peptide-binding site and AGO2 pocket was depicted. Close-up views of the AGO2-peptide interaction were showed in the right panels. FIG. 5F shows that cells treated with 10 µM TAT-11-FITC, TAT-26-FITC or peptides control (TAT-C-FITC) were analyzed under confocal microscopy for the subcellular co-localization of TAT-peptide (Green) and AGO2 (Red). FIG. 5G shows that the binding affinity of TAT-11 and TAT-26 was examined by surface plasmon resonance (SPR). The recombinant AGO2 protein was immobilized on CM5 chip and incubated with a serial dilution (from 625 to 10000 nM) of the two peptides, respectively. The association and dissociation between TAT-11, TAT-26 and immobilized AGO2 were tested by SPR (top). The association rate constant ($K_a$), dissociation rate constant ($K_d$), and equilibrium dissociation constant ($K_D$) were calculated and presented in the chart (bottom).

FIG. 6 shows decoy peptides interrupt MSI1/AGO2 interaction and suppress tumor growth in tumor xenograft model. FIG. 6A and FIG. 6B show that cellular update curves for TAT-11 and TAT-26 peptides. The biological activity of peptides was tested in 05 MG cell line. The cells were treated with different concentration of fluorescein labeled peptides and was measured using ELISA reader. The half-uptake concentration (EC50) values of both peptides were 9.096 and 9.021 µM/ml, respectively. FIG. 6C shows that 05 MG/MSI1-wt and 05 MG/MSI1-wt/shAGO2 cells were subcutaneously transplanted in immunocompromised mice. Once the tumor mass reached 50 mm$^3$, TAT-C or a mixture of TAT-11/TAT-26 (150 µg) was injected at the tumor site 6 times with 3-day intervals. Tumor size was monitored every 2 days (N=6. *P<0.05 vs. TAT-C treated control). FIG. 6D and FIG. 6E show that immunocompromised mice were subcutaneously transplanted with Pt3 or Pt11 primary GBM cells or MIA-PaCa2 PDAC cells. Once the tumor mass reached 50 mm$^3$, TAT-C or a mixture of TAT-11/TAT-26 (150 µg) was injected at the tumor site 6 times with 3-day intervals. Tumor size was monitored every 2 days (N=6. *P<0.05 vs. 05 MG/MSI1-wt cells). FIG. 6F provides a schematic illustrating the animal experiment design to evaluate the tumor suppressive effect of orthotopically delivered TAT-11/TAT-26 (150 µg). FIG. 6G shows that GFP-labeled GBM tumors in serial brain sections of the same mice were observed under fluorescent and optical microscope. Six mice were used in each condition, and the figure showed a representative mouse of each. FIG. 6H shows the results of the survival analysis of mice with orthotopic xenotransplantation of MSI1-overexpressing 05 MG cells (top) and primary cultured tumor cells from recurrent GBM patients (bottom). Mice received two rounds treatment with one-week interval of TAT-C or TAT-11/TAT-26 (150 µg) with cisplatin by i.v. injection. N=6. FIG. 6I provides a schematic illustrating the animal experiment design to evaluate the effects orthotropic delivered TAT-11/TAT-26 (150 µg) on PDAC tumor growth. FIG. 6J shows that immunocompromised mice were transplanted with GFP-tagged MIA-PaCa2 PDAC cells through intraperitoneal injection. Fourteen days after transplantation, mice were intraperitoneally injected with TAT-C or TAT-11/TAT-26 (150 µg) for 6 rounds with 2-day intervals. Mice were sacrificed at day 30 to confirm the GFP tumor signal. FIG. 6K shows that the GFP-tagged xenograft tumors were excised and subjected to IP assay with anti-MSI1 antibody. FIG. 6L shows that the GFP-tagged xenograft tumors were analyzed by qPCR to quantify the expression level of target mRNAs. The bar chart shows relative mRNA level in TAT-11/TAT-26-injected mice versus TAT-C-injected mice.

FIG. 7 shows that cytosolic MSI1 expression associates with GBM relapse and PDAC recurrence in patients. FIG. 7A shows that MSI1 expression was examined by IHC in 18 paired primary and recurrent GBM tissues. Three representative cases (Pt 1 to 3) were presented. Boxes highlighting MSI1 expression pattern. FIG. 7B shows the results of the qPCR analysis of NF2, TP53, p21, CCND1, CDK4, and HELLS mRNA expression levels in microdissected tumor (T) and stroma (S) samples from the 18 paired primary and recurrent GBM specimens. All mRNA expression levels in T parts were first normalized by that in respective S counterparts, and then the total 36 expression levels (primary and recurrent) of each mRNA were rated as percentile from 0% (green) to 100% (red). A heat map shows the relative mRNA expression levels between paired primary and recurrent GBM tissue. FIG. 7C shows qPCR analysis of NF2, TP53, p21, CCND1, CDK4, and HELLS mRNA levels in a group of primary (N=67) and recurrent (N=32) GBM tissues (*P<0.01). P values were estimated by a log-rank test. FIG. 7D shows that 61 recurrent PDAC patient samples were collected and stained for MSI1 by IHC. Three representative cases showed positive stain of cytosolic MSI1. FIG. 7E shows the results of the survival analysis of the cytosolic MSI1-positive (cytosol-positive; N=37) and cytosolic MSI1-negative (cytosol-negative; N=24) recurrent PDAC patients indicates that cytosolic MSI1-positive patients have poorer survival outcome than cytosolic MSI1-negative patients. FIG. 7F shows that in the 37 cytosol-positive PDAC cases, the expression level of cytosolic MSI1 were evaluated by IHC score. In the 20 cases with cytosolic MSI1 (IHC score<0.5), 13 cases survived over 10 months after recurrence; while in the 17 cases with cytosolic MSI1 IHC score>0.5, only 2 cases survived over 10 months after recurrence (P=0.001; Chi-square=10.80). FIG. 7G shows the results of the post-recurrent survival analysis of the two groups (IHC score>0.5 and IHC score<0.5) of cytosol-positive PDAC patients.

FIG. 8 shows the interaction of MSI1 and AGO2 promoted tumor progression under stress environmental stress. Schematic summary of the identified MSI1/AGO2 pathway in regulating stress-induced tumor progression, and the potential therapeutic approach against tumor recurrence. Under normal condition, MSI1 mainly localizes in nucleus, separated from AGO2 which is predominantly in cytoplasm (left). Upon stress condition like cisplatin treatment or hypoxia, MSI1 translocates from nucleus to cytoplasm with its target mRNAs, recruits AGO2 to form a protein complex either on the mRNA CDS of cell cycle promoting genes or mRNA 3'UTR of apoptotic genes, respectively leads to mRNA protection or degradation, and eventually promotes tumor malignancy (middle). By disrupting the MSI1/AGO2 interaction with decoy peptides that mimic specific C-terminal regions of MSI1, the cytosolic MSI1/mRNA complex could not recruit AGO2, as a result, leaving mRNAs of cell cycle promoting genes non-protected and mRNAs of apoptotic genes intact. The decoy peptides may ultimately suppress the pro-oncogenic effects of MSI1/AGO2 complex in therapeutic-resistant cancer cells (right).

FIG. 9 shows that the trafficking MSI1 is essential in MSI1-mediated oncogenic events. FIGS. 9A and 9B show that non-tumorous and different grade of brain tumor tissues from clinical patients were analyzed by IHC to assess the MSI1 expression levels. The ratio of MSI1 expression in each group was presented in the graph. Data are presented as the mean±SD of triplicated experiments (*p<0.001 (Student's t-test)). FIGS. 9C and 9D Left: Immunoblots of the protein expression of MSI1, Laminin A/C and GAPDH in nuclear and cytosolic compartments of two patient-derived primary GBM cells (Pt 3 and Pt 11) as well as MIA-PaCa2 PDAC cells treated with 24-hour hypoxia (T: total protein, C: cytoplasmic, N: nuclear). Right: Pt 3. Pt 11, and MIA-PaCa2 under normoxia or hypoxia for 24 hours were subjected to anti-MSI1 (green) immunofluorescent staining and DAPI (blue) nuclear counter stain. Images were acquired from Carl Zeiss confocal microscope system. Both cells showed increased cytosolic MSI1 under hypoxia condition. FIG. 9E shows that the translocation of MSI1 in 05 MG cells is induced by cisplatin. Top: 05 MG cells pre-treated with or without nuclear export inhibitor leptomycin B (LMB) (10 ng/mL, 2 hours) were further treated by cisplatin (30 µM) for 24 hours. The localization of MSI1 and the nucleus were stained by anti-MSI1 (green) and DAPI (blue), respectively. FIG. 9F shows the functional validation of the identified nuclear exporting signal (NES) using GFP-tagged expressing vectors. Cells transfected with the GFP, NES fused GFP (NES-wt-GFP), or GFP fused with mutated NES (NES-mut-GFP) were treated with or without LMB (10 ng/ml for 2 hours). Top: The scheme for the construction of wildtype NES and mutated NES fused with GFP protein; Bottom: the confocal microscopy imaging for the GFP distribution. FIGS. 9G-I show that 05 MG cells transfected with wildtype or mutated MSI1 were subjected to functional analyses to assess apoptosis, cell proliferation, and clonogenic growth. Hypoxia-induced apoptosis was withdrawn by the overexpression of wild-type MSI1 but not in mutant MSI1 groups determined by annexin V staining, MTT assay, and colony forming assay.

FIG. 10 shows that MSI1 interacted with AGO2 in the cytosol under hypoxia and cisplatin treatment. FIG. 10A shows the Coomassie blue stained SDS-PAGE of the normoxia and hypoxia samples for LC-MS/MS. FIG. 10B provides the list of MSI1-bound and stress-related proteins identified by LC-MS/MS analysis in 05 MG cells. FIG. 10C shows that the Immunoblotting confirmed the candidates identified by proteomic analysis. FIG. 10D provides the results of co-immunoprecipitation of endogenous AGO2 with MSI1 in MIA-PaCa2 PDAC cell line treated with or without hypoxia for 24 hours. FIG. 10E shows that endogenous AGO2 was immunoprecipitated in 05 MG cell lysates with anti-MSI1 antibody under cisplatin (30 µM) stimulation for 24 hrs. MSI1 was pulled down by MSI1 antibody and then subjected to immunoblotting using anti-MSI1 and anti-AGO2 antibody. FIG. 10F shows that 05 MG cells expressing FRET pairs of MSI1-orange and AGO2-GFP were bleached (bottom) at the region of interest (ROI) indicated by the rectangular. Unbleached controls were also performed (top). Fluorescent emission intensities of MSI1 (red) and AGO2 (green) during acceptor photobleaching experiments were shown in the left panel and quantified in the right panel. Quantification of FRET photobleaching experiments was performed by calculating FRET efficiencies for the FRET pairs MSI1 (red)-AGO2 (green). Data represent the mean±S.D. of three independent experiments performed in triplicate (*P<0.05 and **P<0.01 vs control). FIGS. 10G and 10H show that 05 MG cells were under hypoxia or cisplatin (30 µM) for 24 hrs with or without LMB (10 ng/mL). Co-localization of MSI1 (green) and AGO2 (red) was observed by confocal microscopy. Images were acquired from Carl Zeiss confocal microscope system. FIG. 10I shows that Western blot analysis confirmed the knockdown efficiency of AGO2 (clone #1 and #2) in MSI1-overexpressed cells. FIG. 10J shows that 05 MG/Flag-control, 05 MG/MSI1-wt and 05 MG/MSI1-wt/shAGO2 cells were subjected to an apoptosis assay determined by annexin V staining. Hypoxia-induced apoptosis was withdrawn by the over-expression of MSI1 but not with additional knockdown of AGO2.

FIG. 11 shows that identification of mRNA binding targets of MSI1/AGO2. FIG. 11A provides the flow-chart of preparing RNA-binding protein immunoprecipitation (RIP) samples for NGS analysis (RIP-seq). FIG. 11B shows the intersection of mRNA targeted by MSI1 and AGO2. FIG. 11C shows that the gene ontology (GO) enrichment analysis was conducted by DAVID software according to the category of biological processes. Benjamini≤0.05 is selected as interesting GO. The GO accession, name, and the corresponding p-value were shown in the graph. FIG. 11D shows that total RNAs isolated from immunoprecipitation (IP) in cell under normoxia or hypoxia were subjected to mRNA quantitation by using qPCR with specific primer. FIG. 11E shows that 05 MG cells pre-treated with or without LBM (10 ng/mL, 2 hours) and cultured in hypoxia condition for 24 hours were stained for TP53 and CCND1 mRNAs (TAS-cy5, cherry-red), MSI1 (green), and AGO2 (red). Merged images of co-localization of MSI1/AGO2/mRNA (white) by confocal microscopy are shown. FIG. 11F shows that 05 MG/MSI1-wt and 05 MG/MSI1-wt/shAGO2 cells were treated with normoxia or hypoxia conditions for 24 hours. Purified RNA was subjected to quantitative RT-PCR with primers specific to TP53, NF2, CDKN1A, CCND1. CDK4 and HELLS. The mRNA levels under hypoxia were normalized by that under normoxia and shown as relative value in the chart (*P<0.05).

FIG. 12 shows that identification of mRNA binding targets of MSI1/AGO2. Supplementary FIG. 12A Left: schematic illustration presenting the experimental design of xenograft tumor model. Right: Xenograft tumor tissue were sectioned and subjected to ICH to evaluate Flag-MSI1, NF2, p53, p21, cyclinD1, CDK4 and ki67 expression levels. FIG. 12B shows that tumors tissues (five of each group) were harvested and homogenized. Whole-tumor lysates were analyzed by qPCR. FIG. 12C shows the co-immunoprecipitation of endogenous AGO2 with Flag-tagged MSI1 using Flag antibody in 05 MG/MSI1-WT, 05 MG/MSI1-NES-mut, and 05 MG/MSI1-NLS-mut xenograft tumors tissues.

FIG. 13 shows that MSI1 mutants retained its RNA binding capability FIG. 13A provides RNA-protein pull-down assay showing the RNA binding capability of wild-type MSI1. T4 RNA ligase labeled total RNA, AR-3'UTR (positive control), and Poly(A) RNA (negative control) were precipitated and analyzed on SDS-PAGE. AR-3'UTR served as a positive control and was targeted by HuR, whereas Poly (A) RNA served as a negative control. The blot with anti-Flag antibody showed the RNA binding capability of Flag-tagged MSI1. FIG. 13B shows that the NES- and NLS-mutation on MSI1 did not hamper its RNA binding capability. T4 ligase labeled RNA was used to pull-down Flag-control. MSI1-wt, MSI1-NES-mut and MSI1-NLS-mut proteins from respective cell lysates. The RNA-protein pull-down specificity was assessed by Western blot using anti-Fag antibody.

FIG. 14 shows disrupting MSI1/AGO2 interaction in vitro and in vivo by MSI1-C-Term or decoy peptides. FIG. 14A provides schematic presentation of the constructs of full-length, C-terminus, and N-terminus of MSI1 as well as wild-type AGO2 for purifying recombinant proteins. FIG. 14B provides pull-down assay with recombinant MSI1 and AGO2 proteins showing that the C-terminus of MSI1 is essential for the direct MSI1/AGO2 interaction. FIG. 14C shows tumor tissues from MSI1-C-term injected xenografts were immunostained with anti-Flag antibodies to observer the expression of MSI1-C-term in the tumors. FIG. 14D provides the schematic illustration of the split luciferase reconstitution imaging system to real-time monitor the interaction between MSI1 and AGO2. FIG. 14E shows that the split luciferase reconstitution imaging system allows MSI1/AGO2 interaction to be non-invasively monitored and quantified in vivo in a real-time fashion. FIG. 14F shows that the MSI1-AGO2 interaction was able to be real-time monitored by the split luciferase reporter system which indicated the increase of interaction in response to cisplatin treatment. The normalized results were displayed as a bar chart.

FIG. 15 shows the subcellular localization, cellular intake and stability of the decoy peptides in 05 MG cells. FIG. 15A that the cells treated with the two FITC-labeled decoy peptides, TAT-11-FITC and TAT-26-FITC, were analyzed at 0, 0.5 and 1 hours under confocal microscopy. The FITC-labeled peptides can be observed in the cytosol of 05 MG cells. FIG. 15B shows that the cells were respectively treated with two decoy FITC-labeled peptides. After 0.5, 1, 2, 4 and 6 hours, cell lysates were collected and the fluorescent intensity was detected by ELISA reader. N=3 at each time point. The maximum peptide intake can be observed as fast as 1 hour in 05 MG parental cells after treatment. FIG. 15C shows that the cells were respectively treated with two FITC-labeled decoy peptides for 4 hours. Cells were washed and observed under microscopy at the indicated time points. FIG. 15D shows that the cell lysates from FIG. 15C were collected and the fluorescent intensity was measured by ELISA reader. To facilitate comparison of intake and degradation dynamics, mean fluorescence values were normalized to stating fluorescence. All data represent three independent experiments. The FITC-labeled decoy peptides were able to maintain at least 50% of initial dose in cells 4 hours after treatment.

FIG. 16 shows that the decoy peptides reversed the downstream effect of MSI1/AGO2 pathway without affecting the subcellular location of endogenous MSI1. FIG. 16A shows that the cells transfected with peptide control (TAT-C), TAT-11, or TAT-CP26 were under normoxia or hypoxia condition and subjected to qRT-PCR to determine the relative expression level of six downstream targets of MSI1-AGO2. The mRNA levels under hypoxia versus mRNA levels under normoxia were shown in the bar chart (P<0.05 in comparison to normoxia). FIGS. 16B and 16C show that tumor tissues from peptide treated MSI1-overexpressed 05 MG and MIA-PaCa2 xenografts were stained with anti-MSI1 and anti AGO2 antibodies to observe the subcellular localization of MSI1 and AOG2 under peptide treatments.

DETAILED DESCRIPTION OF THE INVENTION

Materials and Methods
1. Cell Culture and Clinical Tissue
The human GBM cell line 05 MG (Denver Brain Tumor Research Group 05), human pancreatic ductal adenocarcinoma cell line (MIA-PaCa2), and its derivative stable cell lines, MSI1-WT, MSI1-NES-mut and MSI1-NLS-mut stable cell lines were cultured in Dulbecco's Modified Eagle's Media (DMEM, Life Technologies Inc., Carlsbad, Calif., USA) supplemented with 10% fetal bovine serum (HyClone Laboratories Inc., South Logan. Utah, USA), 150 g/mL G418 (SIGMA. Cat #A1720), 100 units/mL penicillin, and 100 μg/mL streptomycin (Life Technologies Inc., Carlsbad, Calif., USA) under standard culture condition (37° C., 95% humidified air and 5% CO2). Sub-cultures were performed with 0.25% trypsin-EDTA (Sigma-Aldrich Co. LLC., St. Louis, Mich., USA). All cells lines were tested for microplasma contamination. The clinical tissue samples and tumor cell cultures were acquired from the Neurological Institute of Veterans General Hospitals and Department of Neurological Surgery of Tri-Service General Hospital. All procedures of tissues acquirements have followed the tenets of the Declaration of Helsinki and are reviewed by Institutional Review Committee at Taipei Veterans General Hospital and Tri-Service General Hospital.

2. Animal Care, Tumor Cell Transplantation, and Non-Invasive Imaging

All procedures involving animals were performed in accordance with the institutional animal welfare guidelines of Taipei Veterans General Hospital. For subcutaneous transplantation, cells were harvested, washed, suspended in PBS. The total injected volume of 100 μL were injected subcutaneously into the dorsolateral side of the flank region of 8-week-old male BALB/C nude mice (National Laboratory Animal Center, Taipei, Taiwan) bred and maintained following to the Guidelines for Laboratory Animals in the Taipei Veterans General Hospital. Fourteen days after subcutaneous injection, 2 mg/kg of cisplatin was injected mice twice a week for two weeks through tail vein injection to mimic clinical chemotherapy. Tumor size was measured with calipers[38]. Six mice was used for each condition in each experiment.

For orthotopic transplantation, cells were harvested, washed, suspended in PBS. The total volume of 10 μl were injected orthotopic into the brain of 8-week-old male SCID mice (National Laboratory Animal Center, Taipei, Taiwan) bred and maintained according to the Guidelines for Laboratory Animals in the Taipei Veterans General Hospital. After 14 days of subcutaneous injection, 2 mg/kg of cisplatin was injected mice twice a week for two weeks through tail vein to mimic clinical chemotherapy. For bioluminescent imaging, mice with xenograft tumors were anesthetized with inhalation of 1% isofluorane and imaged by the IVIS 50 imaging system (Caliper Co., Hopkinton, Mass.) every week. D-luciferin (150 mg/kg) was i.p. injection 15 minutes prior to the examination. For each condition, 6 mice was used.

3. Plasmid Constructions and Transfection

MSI1 gene were amplified and sub-cloned from human genomic DNA. The p3xFlag-MSI1 and pmOrange-MSI1 plasmids were generated by inserting a 1038-bp fragment of full-length human MSI1 cDNA into the HindIII/BamHI site of p3xFlag-myc-CMV-26 vector (Sigma, No. E 6401) and pmOrange vector (Clontech, No. 632592). PCR amplified DNA fragment with proper restriction cutting sites were introduced by PCR. The primers used for amplification were listed in Supplementary Table 4. MSI1-NES-mutant and MSI1-NLS-mutant[38]. The clones were created by site-directed mutagenesis according to the manufacturer's instruction (QuikChange II site-directed mutagenesis kit, #200523/200524). The used primers were listed as Supplementary Table 4.

SUPPLEMENTARY TABLE 4

List of the primers used for plasmid construction

| Name | Sequence (5'-3') |
|---|---|
| MSI-F | ATGGAGACTGACGCGCCCCAGCCCG (SEQ ID NO: 1) |
| MSI1-R | TCAGTGGTACCCATTGGTGAAGGCT (SEQ ID NO: 2) |
| MSI1-F-HindIII | AGAAGCTTATGGAGACTGACGCGCCCCAGC (SEQ ID NO: 3) |
| MSI1-R-BamHI | AGGATCCTCAGTGGTACCCATTGGTGAAGG (SEQ ID NO: 4) |
| MSI1-NLS-MutA-F | CGGGACCCCCTGACCGCAGCATCCGCAGGT TTCGGCTTCGTC (SEQ ID NO: 5) |
| MSI1-NLS-MutA-R | GACGAAGCCGAAACCTGCGGATGCTGCGGT CAGGGGGTCCCG (SEQ ID NO: 6) |
| MSI1-NLS-MutB-F | CCCAAGATGGTGACTGCAACGGCAGCAATC TTTGTGGGGGGCTGTCG (SEQ ID NO: 7) |
| MSI1-NLS-MutB-R | CGACAGCCCCCCACAAAGATTGCTGCCGT TGCAGTCACCATCTTGGG (SEQ ID NO: 8) |
| MSI1-NES-Mut-F | CCAGTCCTCCCCGAGGCAACAGCCGCACCT GCAACTGCCTACGGACCA (SEQ ID NO: 9) |
| MSI1-NES-Mut-R | TGGTCCGTAGGCAGTTGCAGGTGCGGCTGT TGCCTCGGGGAGGACTGG (SEQ ID NO: 10) |
| MSI1-C-term-F | ATCGAAGCTTTGCCCTACGGAATGGACGCC (SEQ ID NO: 11) |
| MSI1-C-term-R | TAAGGGATCCTCAGTGGTACCCATTGGT (SEQ ID NO: 12) |
| MSI1-F-Hind III | AATTAAGCTTATGGAGACTGACGCGCCCCAG (SEQ ID NO: 13) |
| MSI1-R-BamHI-T1 | TTAAGGATCCAACTGCTGACCCCCGAGTCC (SEQ ID NO: 14) |
| MSI1-R-BamHI-T2 | TTAAGGATCCATGGCTGTAAGCTCGGGG (SEQ ID NO: 15) |
| MSI1-R-BamHI-T3 | TTAAGGATCCAACTCCGGCTGGCGTAGG (SEQ ID NO: 16) |
| MSI1-R-BamHI-T4 | TTAGGATCCCCGTTGGCGACATCACCT (SEQ ID NO: 17) |

MSI1 C-terminal deletion clone was created by PCR amplification using p3xFlag-MSI1 as the template. The DNA fragments were introduced by an additional restriction enzyme cutting sites by PCR. The 3xFlag-MSI1-C-term plasmid or pEGFP-MSI1-C-term were generated by inserting a 539-bp fragment into the p3xFlag-myc-CMV-26 vector or pEGFP-C1-Vector (Clontech, No. 632592). The used primers were listed in Supplementary Table 5. MSI1 C-terminal truncation clones were created by PCR amplification using p3xFlag-MSI1 plasmid as the template. The 3xFlag-MSI1-deletion plasmids were generated by inserting 870, 804, 770 and 732-bp fragment into the HindIII/BamHI sites of the p3xFlag-myc-CMV-26 vector. The used primers were listed in supplementary Table 6.

SUPPLEMENTARY TABLE 5

Sequences of the primer used for real-time PCR analysis

| Gene Name | Forward sequence | Reverse sequence |
| --- | --- | --- |
| MSI1 | TTGACAAAACCACCAACCGG (SEQ ID NO: 18) | CCTCCTTTGGCTGAGCTTTCTT (SEQ ID NO: 19) |
| p21 | AGTACCCTCTCAGCTCCAGG (SEQ ID NO: 20) | TGTCTGACTCCTTGTTCCGC (SEQ ID NO: 21) |
| TP53 | GGCAGGAAGGCTCCAGATG (SEQ ID NO: 22) | CCTCACTGTTCATATGCCCATTC (SEQ ID NO: 23) |
| CCND1 | GAAGTTGCAAAGTCCTGGAGC (SEQ ID NO: 24) | TGGTTTCCACTTCGCAGCA (SEQ ID NO: 25) |
| CDK4 | TCGTCGAAAGCCTCTCTTCTG (SEQ ID NO: 26) | AGGCAGAGATTCGCTTGTGT (SEQ ID NO: 27) |
| BIRC5 | GAATTCCGGGACCCGTTGG (SEQ ID NO: 28) | CCAAGTCTGGCTCGTTCTCA (SEQ ID NO: 29) |
| AkT1 | GCAGCACGTGTACGAGAAGA (SEQ ID NO: 30) | CCTCCAAGCTATCGTCCAGC (SEQ ID NO: 31) |
| MBP | CCAGGATTTGGCTACGGAGG (SEQ ID NO: 32) | TAGGTAACAGGGGCAAGTGG (SEQ ID NO: 33) |
| TMBIM6 | AGGCGGGTTAGGAAGAGTGG (SEQ ID NO: 34) | GACCATATGGACATAGGCCCC (SEQ ID NO: 35) |
| cdc20 | TGGGTTCCTCTGCAGACATTC (SEQ ID NO: 36) | GCTCCTTGTAATGGGGAGACC (SEQ ID NO: 37) |
| cdc6 | CAGTTCAATTCTGTGCCCGC (SEQ ID NO: 38) | GCTCCTTCTTGGCTCAAGGT (SEQ ID NO: 39) |
| Hells | TTCCCGGGTGAGTGTCCAG (SEQ ID NO: 40) | TATCCCAAGACATGCGAGCC (SEQ ID NO: 41) |
| DLGAP5 | TTCTTGCTGGTGGAGTAGCAG (SEQ ID NO: 42) | TAGACCTGGTGAATCAAGAAGG (SEQ ID NO: 43) |
| DCTN1 | ACTGAAGCCTAAGAAGGCACC (SEQ ID NO: 44) | CTCCAGGAGAGGTGAGGACC (SEQ ID NO: 45) |
| β-actin | GCGTGACATTAAGGAGAAG (SEQ ID NO: 46) | GAAGGAAGGCTGGAAGAG (SEQ ID NO: 47) |
| GAPDH | AGAAGGCTGGGGCTCATTTG (SEQ ID NO: 48) | AGGGGCCATCCACAGTCTTC (SEQ ID NO: 49) |
| 18S rRNA | CAGCCACCCGAGATTGAGCA (SEQ ID NO: 50) | TAGTAGCGACGGGCGGTGTG (SEQ ID NO: 51) |
| Septin 11 | CTAATAAAGCGGGAGGGGCG (SEQ ID NO: 52) | GTCCTATTTCAGTAGTACAGACGC (SEQ ID NO: 53) |
| Septin 2 | GTGGTGGGCTAGACGAGTTTC (SEQ ID NO: 54) | CTTGCGGTGGGTAACTGGAG (SEQ ID NO: 55) |
| ACTN4 | GGCACAGACCAGAGCTGATT (SEQ ID NO: 56) | TCCAGCATCTTGGGGATGTC (SEQ ID NO: 57) |
| ALDH1A3 | TCGACCTGGAGGGCTGTATTA (SEQ ID NO: 58) | CAGGACCATGGTGTTCCCAC (SEQ ID NO: 59) |
| ANXA5 | ACCTGCCTACCTTGCAGAGA (SEQ ID NO: 60) | CTTCCCCGTGACACGTTAGT (SEQ ID NO: 61) |
| ARHGEF12 | AAAGGAGGACCTCTCGCCAA (SEQ ID NO: 62) | GCTGAACAAGACCTGTGGGG (SEQ ID NO: 63) |
| BCAT1 | TGATGCAATCCGCTAGGTCG (SEQ ID NO: 64) | GCATCCGTTACTGCAATCCTTC (SEQ ID NO: 65) |
| BCL2L1 | GAAACGACCTGGCCGATGAA (SEQ ID NO: 66) | GCTCCCGGTTACTCTGAGAC (SEQ ID NO: 67) |

SUPPLEMENTARY TABLE 5-continued

Sequences of the primer used for real-time PCR analysis

| Gene Name | Forward sequence | Reverse sequence |
|---|---|---|
| CALM1 | CAGTGGTGCTGGGAGTGTC (SEQ ID NO: 68) | GATCAGCCATGGTGCGAGC (SEQ ID NO: 69) |
| CALM2 | AGGGAGGTGTTTATGAGGCG (SEQ ID NO: 70) | ACAAAGCTAACCATGCTGCAA (SEQ ID NO: 71) |
| CALM3 | GATGCAGATGGGAACGGGA (SEQ ID NO: 72) | AAAGACACGGAACGCCTCTC (SEQ ID NO: 73) |
| CFL1 | CTCATTGTGCGGCTCCTACTAA (SEQ ID NO: 74) | AGAAGAGCACCGCCTTCTTG (SEQ ID NO: 75) |
| CUL4B | GCAGAATCAGAATGTTCCGGG (SEQ ID NO: 76) | CCTGGAGTTCCTTTTTACCCTCT (SEQ ID NO: 77) |
| DAPK3 | AATCTGAGGAGCTGGGTTGC (SEQ ID NO: 78) | TGATGAACTTGGCTGCGTACT (SEQ ID NO: 79) |
| DCTN2 | TCGATGCGTTTGCACAAGA (SEQ ID NO: 80) | CTGGGGTGTCTCCTTCACTC (SEQ ID NO: 81) |
| DNAJC5 | CCTATCGGAAGCTTGCCTTGA (SEQ ID NO: 82) | CAGCTGGACAGCACGAAGTA (SEQ ID NO: 83) |
| EID1 | CTGGATGGCGGGTTTCAGAT (SEQ ID NO: 84) | AGTTGGGTCCCTCCTCAAGT (SEQ ID NO: 85) |
| EIF4G2 | CCATTCGGGGAGACTCTGGT (SEQ ID NO: 86) | ACCTCCATAGAGCTCCGACT (SEQ ID NO: 87) |
| EIF5A | GCTCGGGTCCTAATCACCCC (SEQ ID NO: 88) | TGCATCTCCTGTCTCGAAGTC (SEQ ID NO: 89) |
| GPX1 | TTTGGGCATCAGGAGAACGC (SEQ ID NO: 90) | CAACATCGTTGCGACACACC (SEQ ID NO: 91) |
| GSTP1 | AGACCAGATCTCCTTCGCTGA (SEQ ID NO: 92) | TCACTGTTTCCCGTTGCCAT (SEQ ID NO: 93) |
| IRAK1 | GAGTGGCTTTGAGAAGCACC (SEQ ID NO: 94) | TCTAGCCTCTCGTACACCTGG (SEQ ID NO: 95) |
| LGALS1 | CTGGAAGTGTTGCAGAGGTGT (SEQ ID NO: 96) | CCGTCAGCTGCCATGTAGTT (SEQ ID NO: 97) |
| MACF1 | GATCTTACAGGAGCGAGCGG (SEQ ID NO: 98) | TGTGCTTGCGGACCTTCATT (SEQ ID NO: 99) |
| MAPRE1 | TTCTGCCGAGAGCCGAAGA (SEQ ID NO: 100) | TTCAAGGCAATGGAGCCAGG (SEQ ID NO: 101) |
| MCL1 | TTCCAGTAAGGAGTCGGGGT (SEQ ID NO: 102) | CCTCCTTCTCCGTAGCCAAA (SEQ ID NO: 103) |
| MDM2 | CAGCAGGAATCATCGGACTCA (SEQ ID NO: 104) | TGTGGCGTTTTCTTTGTCGT (SEQ ID NO: 105) |
| MFN2 | GAAGGTGAAGCGCAATGTCCC (SEQ ID NO: 106) | GTTCTTCTGTGGTAACGGGGT (SEQ ID NO: 107) |
| NACC1 | CTTCTTTGACCGGAACACGC (SEQ ID NO: 108) | AGTACTTGACAGCGTGGAGC (SEQ ID NO: 109) |
| NME1-NME2 | AAGGAACCATGGCCAACTGT (SEQ ID NO: 110) | AGATCTTCGGAAGCTTGCAT (SEQ ID NO: 111) |
| NPM1 | ACTCCAGCCAAAAATGCACA (SEQ ID NO: 112) | CATGTAGTGCCCAGGACTGT (SEQ ID NO: 113) |
| NPM1 | CGGTTGTGAACTAAAGGCCG (SEQ ID NO: 114) | TTTGCACCAGCCCCTAAACT (SEQ ID NO: 115) |
| PAFAH1B1 | ACGAGATGAACTAAATCGAGTAT (SEQ ID NO: 116) | TGACCAAGAGGTCCACCTGA (SEQ ID NO: 117) |

SUPPLEMENTARY TABLE 5-continued

Sequences of the primer used for real-time PCR analysis

| Gene Name | Forward sequence | Reverse sequence |
| --- | --- | --- |
| PPP1CB | AGCTCATCAGGTGGTGGAAGA (SEQ ID NO: 118) | CGGAGGATTAGCTGTTCGAGG (SEQ ID NO: 119) |
| PRC1 | ACCTATTCTGAGTTTGCGAAGGA (SEQ ID NO: 120) | TGATCAGGGCTTCTCAGGACT (SEQ ID NO: 121) |
| PRDX1 | CCCCACGGAGATCATTGCTT (SEQ ID NO: 122) | AAAGGCCCCTGAACGAGATG (SEQ ID NO: 123) |
| PSMB7 | TTCCCAGAGTTGTGACAGCC (SEQ ID NO: 124) | GCCAGAACCCATGGTGACAT (SEQ ID NO: 125) |
| PSMD2 | CGCGAGTTGGTCTGGGAAAA (SEQ ID NO: 126) | CCTCTTCAGACAGCTCCTGTTC (SEQ ID NO: 127) |
| RCC2 | AAGTGTATCTGGTGAGTGGGC (SEQ ID NO: 128) | GGAGTGATGAGAAACCGGAGA (SEQ ID NO: 129) |
| RHOA | CGTTAGTCCACGGTCTGGTC (SEQ ID NO: 130) | ACCAGTTTCTTCCGGATGGC (SEQ ID NO: 131) |
| RNA | TTCTGGAAGGAACGCCGC (SEQ ID NO: 132) | TGGTGTGGAACACTAGGGGA (SEQ ID NO: 133) |
| RPL11 | GAAGGGTCTAAAGGTGCGGG (SEQ ID NO: 134) | ATGCTGAAACCTGGCCTACC (SEQ ID NO: 135) |
| RPS3 | GCGAGTTACACCAACCAGGA (SEQ ID NO: 136) | CCCTCTGGAAAGCCAAACCT (SEQ ID NO: 137) |
| RPS6 | AAGCACCCAAGATTCAGCGT (SEQ ID NO: 138) | TAGCCTCCTTCATTCTCTTGGC (SEQ ID NO: 139) |
| RRM2B | GTAGCTTCGGCGGAGTCTG (SEQ ID NO: 140) | AGTCGACCTCTTCTGCTGTC (SEQ ID NO: 141) |
| S100A6 | CGACCGCTATAAGGCCAGTC (SEQ ID NO: 142) | GCAGCTTCGAGCCAATGGT (SEQ ID NO: 143) |
| SOD1 | ACAAAGATGGTGTGGCCGAT (SEQ ID NO: 144) | AACGACTTCCAGCGTTTCCT (SEQ ID NO: 145) |
| SPIN1 | GGGTGGAAAGAGGGGAATGG (SEQ ID NO: 146) | TGTGCATCGCTGATTCGAGA (SEQ ID NO: 147) |
| SQSTM1 | CCGTGAAGGCCTACCTTCTG (SEQ ID NO: 148) | TCCTCGTCACTGGAAAAGGC (SEQ ID NO: 149) |
| STMN1 | CCATTGTCTGAAGGGACGGG (SEQ ID NO: 150) | GACAAGCGACAGGCAGTGTA (SEQ ID NO: 151) |
| TGM2 | AGTCCCTGGAAATGCCAGCC (SEQ ID NO: 152) | TGTCTACACTGGCCTCGTAGT (SEQ ID NO: 153) |
| TPT1 | AGGGGCTGCAGAACAAATCA (SEQ ID NO: 154) | AGACAGAAAGCGCAGGGATT (SEQ ID NO: 155) |
| TUBB | GCGCTTATCGAAGTGTGGTC (SEQ ID NO: 156) | TTCCCCTAGACACTCGCTCC (SEQ ID NO: 157) |
| UBC | AGTAGTCCCTTCTCGGCGAT (SEQ ID NO: 158) | GACGATCACAGCGATCCACA (SEQ ID NO: 159) |
| UHMK1 | ATTTCCGGCTTCTGGGACTC (SEQ ID NO: 160) | CCATCGGTGTGGGTTAAGGG (SEQ ID NO: 161) |
| USP22 | CCCATCTTTGTCCGGCCTC (SEQ ID NO: 162) | CCAGTTGTCCACCTTGAAGC (SEQ ID NO: 163) |
| YWHAE | GGGTGACGGTGAAGAGCAGAA (SEQ ID NO: 164) | TCAGTGACAATGGGGAGTTTCC (SEQ ID NO: 165) |
| ZWINT | CTCCAGCTTCTGTATACCCTGC (SEQ ID NO: 166) | AGTCAGAGGCCTTTTCTAGGAT (SEQ ID NO: 167) |

SUPPLEMENTARY TABLE 6

Sequences of the primer used for modified-RIP assay.

|  | Forward sequence | Reverse sequence |
| --- | --- | --- |
| TP53-3'UTR-1 | CTGAACAAGTTGGCCTGCAC (SEQ ID NO: 168) | GGGACAGCTTCCCTGGTTAG (SEQ ID NO: 169) |
| TP53-3'UTR-2 | GGCCCACTTCACCGTACTAA (SEQ ID NO: 170) | AGGGAACAAGCACCCTCAAG (SEQ ID NO: 171) |
| TP53-3'UTR-3 | GGTCGGTGGGTTGGTAGTTT (SEQ ID NO: 172) | AGTCTTGGTGGATCCAGATCAT (SEQ ID NO: 173) |
| TP53-3'UTR-4 | ACCCTGTCTGACAACCTCTTGG (SEQ ID NO: 174) | AGGCAGAGATTCGCTTGTGT (SEQ ID NO: 175) |
| TP53-3'UTR-5 | ACCCTGTCTGACAACCTCTTGG (SEQ ID NO: 176) | ATGAACCTGTGGTCCCAGCT (SEQ ID NO: 177) |
| TP53-3'UTR-6 | GCCACCATGGCCAGCCAACT (SEQ ID NO: 178) | CACCCCTCAGACACACAGGT (SEQ ID NO: 179) |
| TP53-CDS-1 | TGAAGCTCCCAGAATGCCAG (SEQ ID NO: 180) | GCTGCCCTGGTAGGTTTTCT (SEQ ID NO: 181) |
| TP53-CDS-2 | TGTGACTTGCACGTACTCCC (SEQ ID NO: 182) | ACCATCGCTATCTGAGCAGC (SEQ ID NO: 183) |
| TP53-CDS-3 | GACATAGTGTGGTGGTGCCC (SEQ ID NO: 184) | ACAAACACGCACCTCAAAGC (SEQ ID NO: 185) |
| TP53-UTR-4 | TTTGAGGTGCGTGTTTGTGC (SEQ ID NO: 186) | CCCACGGATCTGAAGGGTGAA (SEQ ID NO: 187) |
| TP53-UTR-5 | TTCACCCTTCAGATCCGTGG (SEQ ID NO: 188) | CAGTGGGGAACAAGAAGTGGA (SEQ ID NO: 189) |
| NF2-3'UTR-1 | AGAGCTCTAGCAGGTGACCC (SEQ ID NO: 190) | CAGGTCAGAGAACTAGAACGCC (SEQ ID NO: 191) |
| NF2-3'UTR-2 | ATGGCGTTCTAGTTCTCTGACC (SEQ ID NO: 192) | ATGATGGCACTGGCTTCTCA (SEQ ID NO: 193) |
| NF2-3'UTR-3 | GAACATTCATTCCCCCACCG (SEQ ID NO: 194) | CGAGTGCCCTGTACCATCAG (SEQ ID NO: 195) |
| NF2-3'UTR-4 | TGGCTGGGGAGAGACTTTAG (SEQ ID NO: 196) | CACACAGGAAGGAGCGTCTAT (SEQ ID NO: 197) |
| NF2-3'UTR-5 | CGCCCATAGACGCTCCTTC (SEQ ID NO: 198) | CAAAGTGAGGCCTGGGTACAA (SEQ ID NO: 199) |
| NF2-3'UTR-6 | TTGTACCCAGGCCTCACTTTG (SEQ ID NO: 200) | GCCCCAGACCAAGGAGTGAG (SEQ ID NO: 201) |
| NF2-3'UTR-7 | TTTTCTCCATGGCTGATGCTG (SEQ ID NO: 202) | AGCAGCCCAACCCCATTAG (SEQ ID NO: 203) |
| NF2-3'UTR-8 | CTGACCTAATGGGGTTGGGCT (SEQ ID NO: 204) | AGAGCCAGACCTCACTTTACAA (SEQ ID NO: 205) |
| NF2-3'UTR-9 | TCAGTCTTGAAGCCCATCCCT (SEQ ID NO: 206) | CTTGGCACTTCCCAGACTTCA (SEQ ID NO: 207) |
| NF2-3'UTR-10 | CTGAAGTCTGGGAAGTGCCAA (SEQ ID NO: 208) | TCCTGCTACTGGGGCTTGAG (SEQ ID NO: 209) |
| NF2-3'UTR-11 | TAGGGCCTGGGAGTTTGTCA (SEQ ID NO: 210) | GATGAACGAAGCCATCTGTGC (SEQ ID NO: 211) |
| NF2-3'UTR-12 | CCCCCAACCTGTGTTGTCC (SEQ ID NO: 212) | GCAGCTGGTTGTCAGTCTCTG (SEQ ID NO: 213) |
| NF2-CDS-1 | GACGCCGAGATGGAGTTCAA (SEQ ID NO: 214) | TGAAGGTGACTGGTTCTTCCT (SEQ ID NO: 215) |
| NF2-CDS-2 | CAGTGTTCACAAGCGGGGAT (SEQ ID NO: 216) | CACACCGTACATCTCCAGGTC (SEQ ID NO: 217) |

SUPPLEMENTARY TABLE 6-continued

Sequences of the primer used for modified-RIP assay.

| | Forward sequence | Reverse sequence |
|---|---|---|
| NF2-CDS-3 | TCCCGTGGAATGAAATCCGA (SEQ ID NO: 218) | GCTGAACTTCCAAAGAATCGGC (SEQ ID NO: 219) |
| NF2-UTR-4 | TTGGCTGAAAAGGCCCAGAT (SEQ ID NO: 220) | TGCTTCAGCTGATCTGCCTC (SEQ ID NO: 221) |
| NF2-UTR-5 | TGACATGAAGCGGCTTTCCA (SEQ ID NO: 222) | ACCCCTGTCGGAGTTCTCAT (SEQ ID NO: 223) |
| CCND1-3'UTR-1 | GCGTCTCGGGAGAGGATTAG (SEQ ID NO: 224) | GCCTAGAACCCCACTACAGC (SEQ ID NO: 225) |
| CCND1-3'UTR-2 | CCCACAGCTACTTGGTTTGTG (SEQ ID NO: 226) | TTTCTTCTTGACTGGCACGC (SEQ ID NO: 227) |
| CCND1-3'UTR-3 | CTGCGTGCCAGTCAAGAAGA (SEQ ID NO: 228) | ACCTTCCGGTGTGAAACATC (SEQ ID NO: 229) |
| CCND1-3'UTR-4 | GCAGAGGATGTTCATAAGGCCA (SEQ ID NO: 230) | GATGACTCTGGGAAACGCCA (SEQ ID NO: 231) |
| CCND1-CDS-1 | CTGCGAAGTGGAAACCATCC (SEQ ID NO: 232) | AAGACCTCCTCCTCGCACTT (SEQ ID NO: 233) |
| CCND1-CDS-2 | GCCATGAACTACCTGGACCG (SEQ ID NO: 234) | CAATGAAATCGTGCGGGGTC (SEQ ID NO: 235) |
| CCND1-CDS-3 | ACACTTCCTCTCCAAAATGCCA (SEQ ID NO: 236) | TGTGAGGCGGTAGTAGGACAG (SEQ ID NO: 237) |
| CCND1-CDS-4 | GTGATCAAGTGTGACCCGGA (SEQ ID NO: 238) | GCCCTCAGATGTCCACGTCC (SEQ ID NO: 239) |
| HELLS-3'UTR-1 | AAGTGGAGCTCAAGAATAGCTT (SEQ ID NO: 240) | TCTTTGTTCTTGGTAAGGCTCAGA (SEQ ID NO: 241) |
| HELLS-3'UTR-2 | ACTGATTGTCCACTTCACCTTTTT (SEQ ID NO: 242) | AGTACACATCAGCCTGTATCCAA (SEQ ID NO: 243) |
| HELLS-3'UTR-3 | TCTTGGATACAGGCTGATGTGT (SEQ ID NO: 244) | TCTCTCCCCATGAAAAGCCT (SEQ ID NO: 245) |
| HELLS-3'UTR-4 | AGTGATTTCCCTGTATTGGGTTT (SEQ ID NO: 246) | TCTTTGTTCTTGGTAAGGCTCA (SEQ ID NO: 247) |
| HELLS-3'UTR-5 | ACAGGCTGATGTGTACTTAACCA (SEQ ID NO: 248) | GCATAATCCCAATCTCTCCCCA (SEQ ID NO: 249) |
| HELLS-CDS-1 | CAGCGGCGGCTCGGA (SEQ ID NO: 250) | CAGGTCAGAGAACTAGAACGCC (SEQ ID NO: 251) |
| HELLS-CDS-2 | TCGGTACCGTAGACTTCAACA (SEQ ID NO: 252) | TGTTGCTGTTCCATTTTCGTCA (SEQ ID NO: 253) |
| HELLS-CDS-3 | TCAGAGGTCATGTCAAAAGAGGA (SEQ ID NO: 254) | TCCTCTTTTGACATGACCTCTGA (SEQ ID NO: 255) |
| HELLS-CDS-4 | GACCCAGTCCGGAAGTGTAA (SEQ ID NO: 256) | TACACTTCCGGACTGGGTCA (SEQ ID NO: 257) |
| HELLS-CDS-5 | TTGTCTGTGGCCCTTTGTCT (SEQ ID NO: 258) | TGTAGACAAAGGGCCACAGAC (SEQ ID NO: 259) |
| HELLS-CDS-6 | CTTTTGACTGGTACTCCCTTGC (SEQ ID NO: 260) | TCTGCAAAGTCCCTTTCCGT (SEQ ID NO: 261) |
| HELLS-CDS-7 | TCCACTTTCAAAGAAGCAGGAGA (SEQ ID NO: 262) | GGAACTTCAAGAGCAACATCAGA (SEQ ID NO: 263) |
| HELLS-CDS-8 | CCGAGAAAGAGCTGTTGTGGA (SEQ ID NO: 264) | ACAGCTCTTTCTCGGTCCAC (SEQ ID NO: 265) |
| HELLS-CDS-9 | AGGCTTGATGGGTCCATGTCT (SEQ ID NO: 266) | AAAAAGCAGCACCTTGTGACC (SEQ ID NO: 267) |

SUPPLEMENTARY TABLE 6-continued

Sequences of the primer used for modified-RIP assay.

| | Forward sequence | Reverse sequence |
|---|---|---|
| HELLS-CDS-10 | ACCCCCAGTCGGATCTTCAG (SEQ ID NO: 268) | ATCCGACTGGGGGTTCCAA (SEQ ID NO: 269) |
| HELLS-CDS-11 | TTCAAAGGTGGTCAGTCTGGATT (SEQ ID NO: 270) | TCCCCATCTTCTCTTTAATTGGT (SEQ ID NO: 271) |
| HELLS-CDS-12 | GGACCAATTAAAGAGAAGATGGGG (SEQ ID NO: 272) | TGTTCTTGGTAAGGCTCAGAAA (SEQ ID NO: 273) |

In vitro plasmid transfection was carried out using jetPEI DNA transfection reagent (Polyplus Transfection, Huntingdon, UK) according to the manufacturer's instruction. In vivo plasmid transfection in mice were performed with in vivo-jetPEI in vivo nucleic acid delivery reagent (Polyplus-transfection, Illkirch, France). For each intratumoral transfection, 10 μg of FLAG-C-term expression plasmid were mixed with 2 μl of in vivo-jetPEI in a total volume of 50 μl.

4. Gene Expression Analysis.

The RNA samples from 05 MG cells were isolated using TRIzol and confirmed by NanoDrop ND-1000. The RNA integrity was assessed by agarose gel electrophoresis. The gene Expression array (Agilent Technologies) is a customized design with 336 genes identified from the NGS data. The quantitative results were initially aligned by bowtie-1.1.2 and the express-1.5.1 was used for the calculation of quantitative performance following the previous reports[40, 41]. The highest measure of transcripts in average are considered the gene expression, and subsequently standardized by (expression−mean value)/standard deviation.

5. Gene Silencing Using Small Interference RNA (siRNA)

Targeted gene silencing for MSI1, AGO2, and scrambled control were purchased from GE Dharmacon On-TARGETplus siRNA smart pools. Transient transfection was carried out using INTERFERin siRNA transfection reagent (Polyplus Transfection, Huntingdon, UK) according to the manufacturer's instruction (siRNA for MSI1: SASI_Hs01_00145278, siRNA for AGO2: SASI_Hs01_00161740, siRNA for NC cont: SG00217942, Sigma Aldrich Co., St. Louis, Mo., USA). Cell-based experiments were performed after 2-day incubation.

6. Cell Viability Assay

MSI1-WT, MSI1-NES-mut, MSI1-NLS-mut and MSI1-C-term in MSI1-overexpressed cells were seeded in 24-well plates (3000 cells per well) with complete growth medium. The medium was replaced by either solvent or chemicals with indicated concentrations in complete medium. Cell viability assay was then performed. In brief, cells were stained with 0.1 mg/ml 3-(4,5-cimethylthiazol-2-yl)-2,5-diphenyl tetrazolium bromide (MTT, SIGMA, Cat #M2003) for 2 hours and the formazon crystals were then dissolved in DMSO. The relative absorbance was then measured by TECAN Sunrise ELISA plate reader (Thermo Scientific Inc., Waltham, Mass., USA) at 570 nm light absorbance.

7. Colony Formation Assay

MSI1-WT. MSI1-NES-mut and MSI1-NLS-mut were seeded in 6-well plates (1,000 cells per well) and were incubated for 24 hours. The cells were then subjected to hypoxic condition for additional 24 hours. Further 10-day incubation was performed, and the cells were fixed by 10% formalin, and stained by 4% trypan blue (w/v) for 20 min. The stained colonies were washed by PBS and counted.

8. Determination of Apoptosis

Apoptotic events were determined by Annexin V (BD Pharmingen™, #556547). For flow cytometry, cells were harvested and stained with both Annexin V and PI for 10 min. The cells were washed by PBS and resuspended in HEPES for subsequent flow cytometry analysis.

9. Preparation of Nuclear and Cytosolic Extracts

Nuclear and cytosolic extracts were isolated with a Nuclear and Cytoplasmic Extraction kit (Pierce Chemical, Rockford, Ill.). After the incubation period, cells were collected by centrifugation at 1000 rpm for 5 mins at 4° C. The pellets were washed twice with ice-cold PBS, followed by the addition of 0.2 ml of cytoplasmic extraction buffer A and vigorous mixing for 15 sec. Ice-cold cytoplasmic extraction buffer B (11 μl) was added to the solution. After vortex mixing, nuclei and cytosolic fractions were separated by centrifugation at 13000 rpm for 5 mins. The cytoplasmic extracts (supernatants) were stored at −80° C. Nuclear extraction buffer was added to the nuclear fractions (pellets), which were then mixed by vortex mixing on the highest setting for 15 sec. The mixture was chilled, and a 15 sec vortex was performed every 10 mins for a total of 40 mins. Nuclear fraction was centrifuged at 13,000 rpm for 10 mins. The nuclear extracts (supernatants) were stored at −80° C. until use.

10. Western Blotting

Protein samples were prepared with RIPA buffer (Thermo Scientific Inc., Waltham, Mass., USA) containing 1% protease inhibitor. Equal weight of total protein was separated by electrophoresis on SDS/PAGE. After the proteins had been transferred onto a polyainylidene difluoride membrane (Millipore, Bedford, Mass., USA), the blots were incubated with blocking buffer (1×PBST and 5% skim milk) for 1 hour at room temperature and then hybridized with primary antibodies overnight at 4° C., followed by incubation with horseradish peroxidase-conjugated secondary antibody for 1 hour at room temperature. The blots were obtained by X-ray film exposure, and the intensities were quantified by densitometry analysis (Digital Protein DNA Imagineware, Huntington Station, N.Y.). All antibodies were listed in Supplementary Table 9.

SUPPLEMENTARY TABLE 9

Antibody list

| ANTIBODIES | SOURCE | IDENTIFIER |
|---|---|---|
| Rabbit monoclonal anti-Argonaute 2 | Cell Signaling Technology | Cat#2897; |
| Mouse monoclonal anti-Argonaute 2 | abcam | Cat#ab57113 |
| Rabbit polyclonal anti-Argonaute 2 | abcam | Cat#ab32381 |

SUPPLEMENTARY TABLE 9-continued

Antibody list

| ANTIBODIES | SOURCE | IDENTIFIER |
|---|---|---|
| Mouse monoclonal anti-β-Actin | SIGMA | Cat#a5316 |
| Mouse monoclonal anti-Cyclin D1 | abcam | Cat#ab6125 |
| Rabbit monoclonal anti-CDK4 | Cell Signaling Technology | Cat#12790 |
| Rabbit polyclonal anti-HELLS | Cell Signaling Technology | Cat#7998 |
| Rabbit polyclonal anti-HIF-1α | Cell Signaling Technology | Cat#3716 |
| Rabbit polyclonal anti-Lamin A/C | Cell Signaling Technology | Cat#2032 |
| Rabbit monoclonal anti-Musashi-1 | Cell Signaling Technology | Cat#5663 |
| Rabbit monoclonal anti-Musashi-1 | abcam | Cat#ab52865 |
| Rabbit monoclonal anti-Merlin | Cell Signaling Technology | Cat#12888 |
| Rabbit monoclonal anti-p53 | Cell Signaling Technology | Cat#2527 |
| Rabbit monoclonal anti- p21 Waf1/Cip1 | Cell Signaling Technology | Cat#2947 |
| Mouse monoclonal anti-Flag M2 | SIGMA | Cat#F1804 |
| Rabbit polyclonal anti-DDDDK tag | abcam | Cat#ab1162 |
| Mouse polyclonal IgG | Millipore | Cat#12-371 |
| Rabbit polyclonal IgG | Millipore | Cat#12-370 |
| EasyBlot anti-mouse IgG | GeneTex | Cat#GTX225857-01 |
| EasyBlot anti-rabbit IgG | GeneTex | Cat#GTX225856-01 |
| Anti-mouse IgG, HRP-linked Antibody | Cell Signaling Technology | Cat#7076 |
| Anti-rabbit IgG, HRP-linked Antibody | Cell Signaling Technology | Cat#7074 |
| Goat anti-Mouse IgG (H + L) Secondary Antibody, Alexa Fluor 488 conjugate | Invitrogen | Cat#A-11001 |
| Goat anti-Mouse IgG (H + L) Secondary Antibody, Alexa Fluor 555 conjugate | Invitrogen | Cat#A-21424 |
| Goat anti-Rabbit IgG (H + L) Secondary Antibody. Alexa Fluor 488 conjugate | Invitrogen | Cat#A-11008 |
| Goat anti-Rabbit IgG (H + L) Secondary Antibody, Alexa Fluor 568 conjugate | Invitrogen | Cat#A-11036 |
| Human TP53 with Quasar 670 Dye (RNA Fish) | Biosearch Technologies | Cat#VSMF-2423-5 |
| Human CCND1 with Quasar 670 Dye (RNA Fish) | Biosearch Technologies | Cat#VSMF-2047-5 |
| Annexin V | BD Pharmingen ™ | Cat#556547 |
| DAPI | SIGMA | Cat#D9542 |

11. RNA Extraction

Cells were lysed by TRIzol reagent (Life Technologies Inc., Carlsbad, Calif., USA) followed by phenol: chloroform purification and ethanol precipitation. Single strand cDNA was reversely transcribed by SuperScript III reverse transcriptase (Life Technologies Inc., Carlsbad, Calif., USA). Oligonucleotides used for PCR analysis were designed using Primer Express 2.0 (Applied Biosystems, Foster City. Calif., USA).

12. Quantitative Real-Time PCR (qRT-PCR)

Oligonucleotide specificity was computer tested (BLAST, National Center for Biotechnology Information. Bethesda. Md., USA) by homology search with the human genome and later confirmed by melting curve analysis. The qRT-PCR was performed with power SYBR Green PCR Master Mix (Applied Biosystems. Foster City, Calif., USA) according to manufacturer's instruction. Signals were detected using 7900HT Fast Real-time PCR system (Applied Biosystems, Foster City, Calif., USA). The expression level of each gene was normalized to endogenous 18S and experimental control through ΔCt methods. All the antibodies and PCR primers used were listed in the Supplementary Tables. The heatmap of qPCR array data was visualized in R statistical language with ggplot2 package.

13. Co-Immunoprecipitation (Co-IP)

The cells were washed three times with ice-cold PBS and collected by trypsinizing. After centrifugation, cell pellets were resuspended in Buffer-G (50 mM Tris pH 7.5, 170 mM NaCl, 13 mM MgCl2, 0.5% NP40, 0.3% Triton X-100, protease inhibitor cocktail) containing 100,000 U of RNasin Plus RNase inhibitor (Promega Inc., Waltham, Mass., USA, N2615). Firstly, the Dynabeads Protein-G (Invitrogen Inc., Carlsbad, Calif., USA, 10003D) was incubated with 2.5 µl antibody 30 minutes at room temperature. Next, 1 mg protein lysate was incubated with protein-G conjugated-antibody beads for 6 hours or overnight at 4° C. Dynabeads Protein-G was separated by magnetic beads separation stand (Invitrogen Inc., Carlsbad, Calif., USA) and wash 3 times in buffer G. Protein was analyzed by SDS-PAGE. All the used antibodies were listed in Supplementary Table 7.

SUPPLEMENTARY TABLE 7

PepSpot high-throughput peptide array lists

| Index | sequence |
|---|---|
| 1 | FHEINNKMVECKKAQ (SEQ ID NO: 274) |
| 2 | MVECKKAQPKEVMSP (SEQ ID NO: 275) |
| 3 | QPKEVMSPTGSARGR (SEQ ID NO: 276) |
| 4 | PTGSARGRSRVMPYG (SEQ ID NO: 277) |
| 5 | RSRVMPYGMDAFMLG (SEQ ID NO: 278) |
| 6 | GMDAFMLGIGMLGYP (SEQ ID NO: 279) |
| 7 | GIGMLGYPGFQATTY (SEQ ID NO: 280) |
| 8 | PGFQATTYASRSYTG (SEQ ID NO: 281) |

SUPPLEMENTARY TABLE 7-continued

PepSpot high-throughput peptide array lists

| Index | sequence |
|---|---|
| 9 | YASRSYTGLAPGYTY (SEQ ID NO: 282) |
| 10 | GLAPGYTYQFPEFRV (SEQ ID NO: 283) |
| 11 | YQFPEFRVERTPLPS (SEQ ID NO: 284) |
| 12 | VERTPLPSAPVLPEL (SEQ ID NO: 285) |
| 13 | SAPVLPELTAIPLTA (SEQ ID NO: 286) |
| 14 | LTAIPLTAYGPMAAA (SEQ ID NO: 287) |
| 15 | AYGPMAAAAAAAVV (SEQ ID NO: 288) |
| 16 | AAAAAVVRGTGSHP (SEQ ID NO: 289) |
| 17 | VRGTGSHPWTMAPPP (SEQ ID NO: 290) |
| 18 | PWTMAPPPGSTPSRT (SEQ ID NO: 291) |
| 19 | PGSTPSRTGGFLGTT (SEQ ID NO: 292) |
| 20 | TGGFLGTTSPGPMAE (SEQ ID NO: 293) |
| 21 | TSPGPMAELYGAANQ (SEQ ID NO: 294) |
| 22 | ELYGAANQDSGVSSY (SEQ ID NO: 295) |
| 23 | QDSGVSSYISAASPA (SEQ ID NO: 296) |
| 24 | YISAASPAPSTGFGH (SEQ ID NO: 297) |
| 25 | APSTGFGHSLGGPLI (SEQ ID NO: 298) |
| 26 | HSLGGPLIATAFTNG (SEQ ID NO: 299) |
| 27 | LGGPLIATAFTNGYH (SEQ ID NO: 300) |

14. Recombinant Proteins and Pull-Down Assay

The cDNA of human AGO2 and MSI1 were obtained from Addgene, PCR-amplified, and subcloned into pFAST-BAC vector in-frame to an N-terminal 6xHis or FLAG tag, respectively. The baculoviruses for His-AGO2 and FLAG-MSI1 were prepared according to the manual of Bac-To-Bac Baculovirus Expression System (Thermo Fisher Scientific). Briefly, recombinant Bacmid DNA were isolated from pFastbac-HisAGO2 or pFastbac-FlagMSI1 transformed DH10Bac cell, transfected into Sf9 insect cells to produce baculovirus. For isolating recombinant proteins, High Five insect cells were infected with gene-containing baculovirus for 48 hr. The infected cells were harvested and washed in ice-cold PBS, lysed in Lysis buffer (20 mM Tris-HCl pH 7.9, 0.5 mM EDTA, 300 mM KCl, 10% Glycerol, 0.2% TritonX100, 10 µM MG132) at 4° C. for 30 min. Crude lysate were centrifuged at 13K rpm (20000×g) and recombinant proteins were isolated by Nickel (Quiagen) or anti-FLAG M2 (Sigma) resins and eluted in Lysis buffer (with 100 mM KCl) containing 100 mM imidazole or 150 ug/mL 3×FLAG peptide, respectively. For pull-down assay, 2 ug HisAGO2 and 2 ug FLAG-MSI1 were incubated as indicated in lysis buffer (with 100 mM KCl) at 4° C. for 2 h before pull-down by Protein A-immobilized anti-AGO2 antibody. After extensive wash with lysis buffer (100 mM KCl), the precipitated proteins were separated by gel electrophoresis and analyzed by immunoblotting with indicated antibodies.

15. RNA-Binding Protein Immunoprecipitation (RIP)

Magna RIP kits (Millipore, Merck Co., Berlin, Germany, Catalog No. 17-700)[42] was used for RNA-binding protein immunoprecipitation and RNA extraction. The cells were washed twice with ice-cold PBS and cells were collected with 10 ml PBS by cell scraper. Collected cells were pelleted with 10-min centrifugation by 1500 rpm at 4° C. The pellets were then resuspended in an equal volume of RIP lysis buffer (RIP lysis buffer (CS203176), protease inhibitor Cocktail (CS203220) and RNase Inhibitor (CS203219). The magnetic beads were prepared with 2.5 µl antibody for 30 minutes at room temperature, and the protein lysates were mixed with beads-antibody complex in 900 µl of RIP immunoprecipitation buffer (35 µl of 0.5M EDTA (CS203175), 5 µl RNase inhibitor and 860 µl RIP wash buffer (CS203177)) overnight with rotating at 4° C. The beads were washed thrice by ice-cold RIP wash buffer prior to the RNA isolation, followed by the RNA purification by performing proteinase K digestion at 55° C. for 30 mins with vigorous shaking. The supernatant was placed into a new tube and add 250 µl RIP wash buffer. Equal volume of phenol:chloroform:isoamyl alcohol (25:24:1) was added for RNA isolation. Vortex for 15 seconds and centrifuge at 14000 rpm for 10 mins to separate the phases. Move 350 µl of the aqueous phase into new tube and add 400 µl of chloroform. Vortex for 15 seconds and centrifuge at 14000 rpm for 10 mins. Remove 300 µl the aqueous phase into new tube and add 50 µl Salt Solution I (CS203173), 15 µl Salt Solution II (CS203185), 5 µl of Precipitate Enhancer (CS203208) and 850 µl absolute ethanol and freeze the samples at −80° C. overnight. At the very next day, each sample was centrifuged at 14000 rpm for 30 mins, removed supernatant, and washed pellets with 80% ethanol and centrifuge at 14000 rpm for 15 mins. Removed supernatant and air dry the pellets. The isolated RNAs were then resuspended in 20 µl of RNase-free waster (CS203217). All the antibodies and PCR primers used in this section were listed in Supplementary Tables[43].

16. Modified RNA-Binding Protein Immunoprecipitation (Modified-RIP)

We used RNA ChIP-IT kit (Catalog No. 53024)[44] for a modified-RIP assay to study the interaction regions of RNA-binding proteins on their target RNAs. Add 175 µl of 37% formaldehyde per 6.5 ml medium of sample in culture dish (final concentration has to be approximately 1%) for 5 mins to fix the samples. Then add 825 µl Glycine to the sample (final concentration has to be 0.125M) for 5 mins at room temperature to stop fixation. Remove the supernatant and discard. Washed the cell pellet and collected by centrifugation at 1000 rpm for 5 mins at 4° C. Resuspend cells in ice-cold Complete Lysis Buffer, incubate on ice for 30 mins and transfer the cell by centrifugation at 5000 rpm for 10 mins at 4° C. Remove the supernatant and resuspend the pellet in complete shearing buffer. Submit the samples to sonication to shear the chromatin using the Bioruptor® for 1 to 4 run of 5 cycles: [30 seconds "ON", 30 seconds "OFF"] each (20 cycles). Spin the control and sonicated samples at 12,000 rpm for 10 minutes. The supernatant, except the upper lipid layer, is collected. Treat the chromatin with 10 μl DNase 1 for 20 mins at 37° C. and stop the reaction by adding 10 10 μl 0.5M EDTA before performing the IP.

First, the Dynabeads Protein-G was incubated with 2.5 μl 1 antibody 30 minutes at 4° C. Next, the protein lysis 1 mg incubated with protein-G-conjugated-antibody beads overnight at 4° C. for parental cells. Dynabeads Protein-G was separated by Complete RNA-ChIP Elution Buffer by rotate for 15 mins in the end-to-end rotor at room temperature. Transfer the supernatants and add 2 μl 5M NaCl and 2 μl proteinase K to each sample for 1 h at 42° C. to digest the proteins. Then, incubate for 1.5 hrs at 65° C. to reverse the cross-links. RNA was extracted with phenol/chloroform/isoamyl alcohol, dissolved in 20 μl of KAPA distilled water, and used as a source of RNA for End point RT-PCR analysis (KAPA SYBR FAST Universal One-step qRT-PCR kit, KR0393). Each experiment was done in three distinct biological replicates. Quantification of fold changes of the signals was done by normalizing to IgG-precipitated controls. All the antibody and PCR primer were listed in the Supplementary Tables.

17. RNA-Protein Pull-Down Assay

We used Pierce Magnetic RNA-Protein Pull-Down kit (Thermo Cat.20164) for studying RNA binding efficiency of different mutation clones of MSI1. The RNA was purified and labeled by T4 RNA ligase overnight at 4° C. The labeled RNA was captured with streptavidin magnetic beats for 30 mins at room temperature. Removed the supernatant and wash the beads three times by protein-RNA binding buffer. Added the protein of Master Mix to the RNA-bound beads then mix by gentle vortex. Incubated 60 mins at 4° C. with rotation. Washed the beads and eluted by SDS-PAGE loading buffer. Protein was analyzed by SDS-PAGE. All the used antibodies were listed in Supplementary Table 9.

18. RNA-Fluorescence In Situ Hybridization (RNA-FISH)

The cells were sub-cultured on 18 mm around coverglass in a 12-well cell culture plate 24 h. After overnight cultured, cells were stimulated hypoxia. The cells were fixed with 3.7% formaldehyde for 5 mins. Permeabilized with 0.1% Triton X-100 for 5 mins at room temperature. The immune-stained with the indicated primary antibodies in hybridization buffer (Biosearch Technologies Cat #SMF-HB1-10) overnight at 4° C., respectively, followed by FITC-labeled or PE-labeled secondary antibodies in wash buffer A (Biosearch Technologies Cat #SMF-WA1-60). Finally, DAPI nuclear stain (wash Buffer A of 5 ng/mL DAPI) to counterstain the nuclei that allowed imaging. The antibody used in this study was listed in Supplementary KEY RESOURCES TABLE and the RNA FISH probes as below: Human TP53 with Quasar 670 Dye (Cat.VSMF-2423-5) and Human CCND1 with Quasar 670 Dye (Cat.VSMF-2047-5)[45].

19. Immunofluorescence (IF) Staining

Cells were sub-cultured on glass coverslips or chamber slides 24 hrs prior to the experiment. Cell were then subjected to undergo hypoxia with designated time in complete culture medium. The cells were fixed with 4% paraformaldehyde for 10 mins. Permeabilized with 0.1% Triton X-100 for 10 mins and incubated with blocking buffer (5% BSA) for 1 hour at room temperature. The immune-stained with the indicated primary antibodies overnight at 4° C., respectively, followed by FITC-labeled or PE-labeled secondary antibodies for imaging. The secondary antibodies used in this study were listed in Supplementary Table 9.

20. Fluorescence Resonance Energy Transfer (FRET) Assay

The plasmids who generate fluorescent fusion protein, MSI1-pmOrange and AGO2-EGFP[46], were co-transfected into GBM cells. Twenty-four hours after transfection, cells were stimulated with hypoxia. The cells were washed twice with ice-cold PBS and fixed using 4% paraformaldehyde for 10 mins. Photo-bleaching was performed by 514-nm wavelength laser exposure at the maximal intensity. An excitation wavelength of 488 nm and an emission wavelength of 520±20 nm were used for GFP, and an excitation wavelength of 555 nm and an emission wavelength of 580±20 nm were used for mOrange spectrum. The FRET energy transfer efficiency ($E_f$) was calculated as $FRET_{eff}=(I_{post}-I_{pre})/I_{post}$ where $I_{pre}$ and $I_{post}$ are the total fluorescence of the ROI before and after bleaching[47].

21. Liquid Chromatography-Mass Spectrometry (LC-MS/MS) Analysis

LC-MS/MS analysis was performed through the application of LTQ Orbitrap (Thermo Fisher Scientific Inc., Waltham, Mass., USA) as previously described. In brief, each sample of digested peptides was reconstituted to 20 μl of 0.1% formic acid (FA). Peptides were firstly injected in and separated by the nanoflow HPLC (Agilent 1100, Agilent Technologies, Santa Clara, Calif. USA) with a C18 column (75 μm ID×360 μm OD×15 cm; Agilent Technologies, Santa Clara, Calif., USA), and became ionized particles once passed through the succeeding nanospray tip (New Objective, Woburn, Mass.). In operating HPLC, the flow rate was at 0.4 μl/min after a splitter. LC gradient for the LC-MS/MS system ramped from 2% ACN to 40% ACN in 120 min, and the system was performed under the setting of automated data-dependent acquisition, with mode of 200-2000 m/z full scan for the maximum 3 most intense peaks from each Orbitrap MS scan. Peptides with +2 or +3 charge state were further subjected to CID. Spectra were obtained in raw data files with Xcalibur (version 2.0 SR2). Protein identification was accomplished via TurboSEQUEST (Thermo Finnigan, San Jose, Calif., USA) using the UniProt database. A protein was confirmed once 3 peptides with Xcorr>2.5 were matched in sequencing[48].

22. PepSpot High-Throughput Peptide Tiling Array

To rapidly screen the putative binding hotspots along the C-terminus of MSI1, we mimicked the epitope screening method by dotting the synthetic short peptides on nitrocellulose membrane and incubated with purified AGO2 protein[39]. The C-terminus of MSI1 (201-262) was divided into 27 individual synthetic peptides with N-terminal amine attached on the nitrocellulose. Each peptide is 15 amino acids in length and has 8 amino acids overlapping with the previous neighboring peptide (Suppl. Table IV). The purchased PepSpot membrane (JPT peptide technologies, Berlin, Germany) was firstly rinsed by methanol for 5 minutes, followed by Tris buffer saline supplemented with 0.1% Tween-20 (TBS-T) washing thrice. The membrane was then blocked by Superblock T20 blocking buffer (Thermo Fisher Scientific Inc., Waltham, Mass., USA) for 2 hours and 2 μg His-tagged AGO2 recombinant protein was added for an overnight incubation. The membrane was washed thrice with TBS-T and incubated with horseradish peroxidase (HRP)-conjugated 6×His tag primary antibody (Genetex Inc., Hsinchu, Taiwan) for 4 hours under 4° C. Enhanced chemiluminescent reagent was used for further blotting.

23. Biotinylated Peptide Synthesis and Cell-Penetrating Peptide-Tagged Assay

In vitro binding assay was carried out with N-terminal biotinylated synthetic peptides (Supplementary Table 8)

based on our peptide array screening. The synthesized peptides (Thermo Fisher Scientific Inc., Waltham, Mass., USA) were dissolved in 10% DMSO by 1 mg/ml and subjected to incubate with equal amount of AGO2 recombinant protein (2 µg each) in T20 blocking solution (Thermo Fisher Scientific Inc., Waltham, Mass., USA). After 16-hour incubation, the peptides were pull-down with immobilized streptavidin (Pierce 21115. Thermo Fisher Scientific Inc., Waltham. Mass., USA). The precipitated peptide/protein complex was subjected to immunoblotting with 6×His primary antibody (GeneTex Inc., Hsinchu, Taiwan) hybridization and detection. Peptide transfection was carried out with Proteojuice (Millipore 71281, Merck Co., Darmstadt. Germany) following the manufacturer's instruction. For the in vivo compatible cell-penetrating peptide (CPP)-modified peptides, we tested two different CPPs at the C-terminal ends, including TAT (48-60) from HIV and arginine tandem repeats (R7-R9)[50-52].

SUPPLEMENTARY TABLE 8

N-terminal biotinylated synthetic peptides lists

| | Sequence (N'-C') |
|---|---|
| CP_NC | Biotin-GSHPWTMAPPPGSTP (SEQ ID NO: 301) |
| CP245 | Biotin-YQFPEFRVERTPLPS (SEQ ID NO: 302) |
| CP260 | Biotin-HSLGGPLIATAFTNG (SEQ ID NO: 303) |
| TAT-CP_NC | GSHPWTMAPPPGSTPGRKKRRQRRRPPQ (SEQ ID NO: 304) |
| TAT-CP245 | YQFPEFRVERTPLPSGRKKRRQRRRPPQ (SEQ ID NO: 305) |
| TAT-CP260 | HSLGGPLIATAFTNGGRKKRRQRRRPPQ (SEQ ID NO: 306) |
| CP_NC (R9) | GSHPWTMAPPPGSTPRRRRRRRRR (SEQ ID NO: 307) |
| CP245 (R9) | YQFPEFRVERTPLPSRRRRRRRRR (SEQ ID NO: 308) |
| CP260 (R9) | HSLGGPLIATAFTNGRRRRRRRRR (SEQ ID NO: 309) |
| FITC-TAT-CP_NC | 5FAM-GSHPWTMAPPPGSTPGRKKRRQRRRPPQ (SEQ ID NO: 310) |
| FITC-TAT-CP245 | 5FAM-YQFPEFRVERTPLPSGRKKRRQRRRPPQ (SEQ ID NO: 311) |
| FITC-TAT-CP260 | 5FAMHSLGGPLIATAFTNGGRKKRRQRRRPPQ (SEQ ID NO: 312) |

24. Split Luciferase Reconstitution Reporter Assay

To use *Gaussia* luciferase (Gluc) for detecting protein-protein interaction, we split *Gaussia* luciferase into NGluc (N-terminal Gluc, 106 a.a.) and CGluc (C-terminal Glue. 79 a.a.)[53,54]. The two fragments were amplified by polymerase chain reaction (PCR) and subjected to construct fusion protein with MSI1 and AGO2 by the pcDNA 3.1 and pCMV backbone, respectively. Each fusion protein contains a flexible linker $(GGGGS)_2$ between the protein and polypeptides of split luciferase[55,56]. Stable cell lines were obtained by stable transfection of both fusion protein expressive plasmids in 05 MG GBM cell line with Hygromycin B (Sigma Aldrich Co., St. Louis, Mich., USA) and G418 sulfate (Merck Co., Berlin, Germany). To establish a normalizing standard, we transduced multiple reporter genes into the aforementioned stable cell line for stably expressing green fluorescent protein (GFP), firefly luciferase (FLuc) and herpes simplex virus type I thymidine kinase (HSV1-tk) using lentivirus as previously described[57]. For in vitro study, the cells were lysed in mild reporter lysis buffer (Promega Co., Madison, Wis., USA) with a frozen-thaw cycle. The supernatant was collected after brief centrifugation and dispensed in 96-well black flat bottom plate. Coelenterazine (Nanolight Technologies, Ltd., Pinetop, Ariz., USA), the substrate of GLuc, was firstly dissolved in methanol and diluted in reporter assay buffer (15 mM potassium phosphate, 25 mM glycylglycine, 15 mM MgSO4, 4 mM EDTA). D-luciferin sodium salt (Promega Co., Madison, Wis., USA) was dissolved in sterilized water and diluted in reporter assay buffer supplemented with 2 mM ATP. The bioluminescent signals were acquired by Wallac 1420 Victor$^2$ Microplate Reader (Perkin Elmer, Waltham. Mass., USA) equipped with auto-dispenser to avoid rapid decay of GLuc. For in vivo study, the xenografted mice were anesthetized by isoflurane inhalation (1% in $O_2$ supplement) prior to the In Vivo Imaging System (IVIS 50, PerkinElmer, Waltham, Mass., USA) acquisition. The coelenterazine was injected through tail vein for a total of 15 µg per mouse, and the image was acquired within 5 minutes. The mice would be recovered from luminescent status for 30-minute rest; after that, the mice would undergo an intraperitoneal injection of D-luciferin (150 mg/kg) for tumor size normalization. The region of interests (ROI) was automatically chosen by the Living Image 4.2 software and quantified as photon flux in a certain area per second (photons/s/cm$^2$).

25. Immunohistochemistry Staining and Immunoblotting (IHC)

Tumor specimens from mice were fixed with 4% paraformaldehyde (Sigma Aldrich Co., St. Louis, Mo., USA). Section were deparaffinized and rehydrated before staining. Tissue antigen were retrieved by boiling in 10 mmol/L (pH 6) citrate buffer (Sigma Aldrich Co., St. Louis, Mo., USA) for 10 mins. Sections were cooling down in PBS for 10 mins before treating with 3% $H_2O_2$. Sample were blocked in 5 mg/ml BSA (Sigma Aldrich Co., St. Louis, Mo., USA) in PBS for 30 mins before hybridizing with 100 dilute primary antibodies Signals were amplified by the TSA Biotin System (PerkinElmer, Waltham, Mass., USA) as instructed by the manufacturer and then counterstained with hematoxylin (Sigma Aldrich Co., St. Louis. Mo., USA, #201708) for 30 mins[58]. The antibodies used in this study were listed in Supplementary Table 9.

26. Laser Capture Microdissection (LCM)

Serial sections (n=3-20, 8 µm) were cut from each formalin-fixed paraffin-embedded (FFPE) sample and stored at 4° C. until use. A 4-µm thick section was cut for H&E staining. Immediately before LCM, the sections were deparaffinized, stained with hematoxylin for 1 minute, dehydrated through alcohol gradients for 30 seconds each, and finally immersed in xylene for another 3 minutes and air-dried. The microdissection was performed using ArcturusXT Laser Capture Microdissector (Applied Biosystems-Life Technologies, Carlsbad. Calif., USA) following the manufacturer's instrument. AutoScan™ analysis software module was implemented when using the ArcturusXT LCM instrument, which allowed the user to visually inspect the regions of interest. Approximately 5000 cells were captured per specimen and subsequently used for the following studies. Two 5-µm-thick sections were cut from each block and placed in sterile 1.5-mL centrifuge tubes for extraction. Tubes containing cut FFPE sections for RNA purification were stored at −80° C. until use. Total RNA including small RNAs was extracted using FFPE RNA Isolation Kit (Life Technologies Corporation. Carlsbad, Calif., USA) following the instruction. RNA yield was determined from the A 260/A 280 absorbance ratios using a NanoDrop ND-1000 spectrophotometer (Thermo Fisher Scientific, Waltham, Mass., USA).

27. Affinity Measurement by Surface Plasmon Resonance (SPR)

A Biacore T200 (GE Healthcare) was used to study the binding affinity of the TAT-11 and TAT-26 peptides with recombinant His-tagged AGO2 protein. The recombinant His-AGO2 and TAT peptides were diluted in HBS-P buffer (10 mHEPES, 150 mM NaCl and 0.005% P20, pH 7.4). To evaluate the binding affinity, recombinant His-AGO2 was immobilized on a CM5 sensor chip (GE Healthcare, BR100012) via amine coupling (~7000 RU) for 3600 sec at rate of 5 μl/mins, followed by dissociation for 600 s. After injection of each peptide, the surface was regenerated with an injection of 10 mM NaOH. All sensorgrams were double referenced by subtracting the surface effect from the control flow peptide and the buffer effect form the blank buffer. The kinetic values Ka, Kd and $K_D$ were obtained using Biacore T2000 Evaluation Software (GE healthcare) assuming the Langmuir 1:1 binding model.

28. Statistical Analysis

Data are expressed as the mean±SD from at least three independent experiments. The statistical analysis was performed using student's T-test. Difference were considered significant when p≤0.05 or p≤0.01.

29. Data Availability

Authors can confirm that all relevant data are included in the article and/or its supplementary information files.

Results

Example 1. Cytosolic Translocation of MSI1 is Essential for its Pro-Oncogenic Effects Under Stress Overexpression of MSI1 has been reported in several tumor tissues[9,10,13-17]. We first examined the correlation between MSI1 and tumor progression by immunohistochemical (IHC) staining on a small cohort of glioma patient samples. We found that high levels of MSI1 expression positively correlated with severe cancer malignancy and recurrence (FIG. 9A and FIG. 9B) and also observed a significant proportion of MSI1 proteins in the cytosol in recurrent glioma samples compared with the non-recurrent samples (FIG. 1A). We asked whether MSI1 could be dynamically regulated in response to hypoxic or chemotherapeutic agents. To address this possibility, we first exposed 05 MG cells, human glial cells derived from a patient with glioblastoma (GBM), to hypoxic treatment. Cell exposure to hypoxia did not affect the total level of MSI1, but increased MSI1 levels in the cytosolic compartment (FIG. 1B and FIG. 1C). Similar results were obtained with primary GBM cells (FIG. 9C) and pancreatic ductal adenocarcinoma (PDAC) cell lines (FIG. 9D). Addition of Leptomycin B (LMB), an inhibitor of the nuclear export receptor CRM1, strongly reduced MSI1 translocation into the cytosol upon hypoxic and cisplatin treatment (FIG. 1B, FIG. 1C and FIG. 9E), suggesting an active and CRM1-dependent MSI1 translocation in response to environmental stress. Subcellular localization is generally relied on a nuclear localization signal (NLS) and a nuclear export signal (NES). Two NLS sites have been reported in the N-terminal domain of MSI1[24] (FIG. 1D). We identified a potential NES motif (263-LTAIPL-268) within the C-terminus of MSI1 and confirmed the functionality of this motif (FIG. 1D and FIG. 9F). Mutations in the NLS and NES motifs of MSI1 were generated; Flag-tagged wild-type MSI1 (MSI1-wt), NES-mutant MSI1 (MSI1-NES-mut) and NLS-mutant MSI1 (MSI1-NLS-mut) were stably expressed in GBM cells (FIG. 1E). Under hypoxic conditions, MSI1-NES-mut and MSI1-NLS-mut remained respectively located in the nucleus and cytosol while MSI1-wt translocated into the cytosol (FIG. 1E), suggesting that the NES motif plays an active role in the subcellular translocation of MSI1 upon stress treatment.

We next investigated the biological consequences of MSI1 translocation. In vitro functional assays showed that cells overexpressing MSI1-wt exhibited decreased apoptosis, and increased proliferation and viability under hypoxia compared with parental, MSI1-NES-mut and MSI1-NLS-mut overexpressing cells (FIGS. 9G, 9H and 9I). Consistently, in vivo studies revealed that xenografts of GBM cells overexpressing MSI1-wt grew significantly bigger tumors than that of parental or mutant GBM cells (FIG. 1F and FIG. 1G). Subcellular localization of MSI1 and its mutants in xenografts (FIG. 1G and FIG. 1H) was consistent with that observed in FIG. 1E. We further explored the consequences of MSI1 shuttling in GBM under oxidative stress by treating subcutaneous or orthotopic xenografts with cisplatin (FIG. 1I). Compared with our previous experiments (FIG. 1F and FIG. 1G), cisplatin treatment enhanced tumor growth of xenografts overexpressing MSI1-wt (774.365 mm³ vs 477.437 mm³ tumor volume at day 22) (FIG. 1J and FIG. 1K). Mice intracranially implanted with xenografts overexpressing MSI1-wt and sequentially treated with cisplatin showed an outrageous tumor invasion compared with other groups (FIG. 1L), suggesting that the nuclear-cytoplasmic shuttling of MSI1 strictly governs its biological function in tumorigenicity. Together, our findings showed that stress-induced translocation of MSI1 is required for its pro-oncogenic functions.

Example 2. Cytosolic MSI1 Directly Binds AGO2 to Modulate the Expression of its Target mRNAs To address the underlying molecular mechanisms by which MSI1 shuttling promotes stress-induced tumor progression, we characterized MSI1 interacting proteins by mass spectrometry analysis. The Flag-tagged MSI1 protein complex in the cytosolic fraction of 05 MG cells under normoxia or hypoxia was purified and characterized[25] (FIG. 2A and FIG. 10A). Among the interacting proteins that are related to stress response (FIG. 10B), we found that hypoxic stress significantly enhanced the recruitment of AGO2 to cytosolic MSI1 in GBM and PDAC cancer cells (FIG. 2B and FIGS. 11C and 11D). In vitro binding assay confirmed the direct interaction between recombinant MSI1 and AGO2 (FIG. 2C). Fluorescence Resonance Energy Transfer (FRET) microscopy (FIG. 2D and FIG. 10F), and confocal microscopy in cisplatin-treated (FIG. 10G) and hypoxia-treated (FIG. 10H) cells confirmed the stress-induced interaction between MSI1 and AGO2. We next investigated whether AGO2 is essential for the oncogenic functions of MSI1. In vitro functional assays showed that AGO2 knockdown (FIG. 10I) in MSI1-overexpressed cells suppressed the viability (FIG. 2E) and proliferation (FIG. 2F) through enhanced apoptosis (FIG. 10J). Concomitantly, in vivo studies showed that AGO2 knockdown abolished the MSI1-enhanced tumor growth (FIG. 2G). These data showed that AGO2 as an important downstream effector of MSI1 involved in cancer development. To characterize the functional roles of stress-induced AGO2-MSI1 interaction, we performed RNA immunoprecipitation sequencing (RIP-Seq) by pull-down MSI1 and AGO2 respectively, and identified 336 common mRNA targets bound by MSI1/AGO2 complex (FIG. 11A and 11B). Gene Ontology (GO) analysis of the mRNAs associated with both MSI1 and AGO2 showed enrichment in cell cycle progression and apoptosis pathways (FIG. 11C), consistent with the cellular phenotype we observed. We further confirmed the binding of MSI1/AGO2 complex to some of the mRNA targets upon hypoxia (FIGS. 11D and 11E), and investigated the impact of MSI1/AGO2 binding on the expression level of the 336 common target mRNAs. Steady mRNA levels were profiled by microarrays in control, MSI1- and AGO2-knockdown cells cultured under normoxia or hypoxia. Intriguingly, we observed two distinct groups of mRNA targets, with the first group (group 1) enriched in apoptotic genes exhibiting increased mRNA level after knockdown of MSI1 and AGO2 under hypoxia, and the second group (group 2) of genes mainly involved in cell cycle regulation showing opposite regulatory trend (FIG. 2H). We selected three mRNA targets from each group—NF2, TP53, and p21 from group 1, and CCND1, CDK4, HELLS from group 2—and evaluated their degradation rate under normoxia and hypoxia by treating cells with actinomycin D (FIG. 2H). In control cells, hypoxic stress decreased the half-life of group 1 mRNAs while increased the stability of group 2 mRNAs. In contrast, we observed the opposite effect in MSI1- and AGO2-knockdown cells (FIG. 2I), suggesting that MSI1/AGO2 complex could stabilize in response to stress a subset of mRNA targets related to cell cycle (group 1) to subsequently promote tumor progression. Along with this idea, MSI1/AGO2 binding could also negatively regulate the stability of another subset of mRNA targets related to apoptosis (group 2) to ensure cancer cell survival. We verified our hypothesis by qPCR and confirmed the existence of two distinct types of regulation: 1) the stability of mRNA targets from group 1 decreased in response to hypoxia and 2) the mRNA targets from group 2 remained expressed at similar levels after hypoxia (FIG. 2J). Of note, AGO2 is essential for the stress-induced and MSI1-mediated regulation of downstream mRNAs as AGO2-knockdown in MSI1-overexpressed cells abrogated the regulation of group 1 and group 2 mRNA stability (FIG. 11F). Consistent with cytosolic MSI1-AGO2 interaction, we found that cells overexpressing MSI1 mutants, with detoured subcellular localization, recaptured the functional consequence on mRNA stability in a similar manor to the one caused by knockdown of MSI1 in response to hypoxia (FIG. 2K). This opposite effect was also observed in vivo with a xenograft mouse model (FIG. 12A and FIG. 12B), in which the MSI1/AGO2 interaction was confirmed (FIG. 12C).

Example 3. MSI1/AGO2 Binding to a Specific Location on its Targets Mediates Distinct mRNA Fates To decipher the molecular mechanisms by which MSI1/AGO2 complex regulates mRNA stability, we carried out RIP experiments in control. MSI1- and AGO2-knockdown cells under normoxia and hypoxia. Interestingly, MSI1 bound to its mRNA targets under normal and hypoxic conditions while AGO2 bound to its targets only under hypoxia (FIG. 3A). Knockdown of AGO2 did not affect MSI1 binding to its mRNA targets whereas knockdown of MSI1 hampered AGO2 recruitment (FIG. 3A), suggesting a MSI1-dependent recruitment of AGO2 to mRNA targets under hypoxia. We next investigated the impact of MSI1 shuttling on MSI1-mRNA complex formation. To do so, we performed RIP experiments with the cytosolic and nuclear fractions of cells overexpressing MSI1-wt cultured under normoxia and hypoxia conditions. We showed that under normoxia, MSI1-mRNA complexes were in the nucleus and that upon hypoxia, they were enriched in the cytosol (FIG. 3B, top right panel), suggesting an active translocation of MSI1-mRNA complexes into the cytosol in response to hypoxia. When MSI1 failed to shuttle into the cytosol (MSI1-NES-mut), the MSI1-mRNA complex remained in the nuclear compartment as expected (FIG. 3B, middle right panel). Surprisingly, the cytosolic mutant of MSI1 (MSI1-NLS-mut) was unable to bind RNA (FIG. 3B, bottom panel). This, however, was not due to the disruption of RNA binding property of the MSI1-NLS-mut, as both MSI1 mutants exhibited similar binding affinity with target RNA sequence as MSI1-wt (FIGS. 13A and 13B). Our data suggested that MSI1 first needs to bind its target mRNAs in the nucleus before carrying them into the cytosol in response to hypoxia. Consistently, the recruitment of AGO2 to the MSI1-mRNA complexes occurred in the cytosol (FIG. 3B, top left panel). However, MSI1-NLS-mut did not interact with AGO2 (FIG. 3B, bottom left panel), suggesting their interaction to be RNA-dependent in the cytosol. We next further characterized binding regions of MSI1-AGO2 complex on its mRNA targets by performing RIP followed by RNA fragmentation and qPCR (RIP-qPCR). We showed that, in response to hypoxia, MSI1/AGO2 complex bound the three prime untranslated (3'-UTR) region of target mRNAs from group 1 while it bound the coding sequence (CDS) region of those from group 2 (FIG. 3C). Collectively, our data showed that upon hypoxia, MSI1 together with its bound mRNA targets translocates into the cytosol where it subsequently recruits AGO2 to mediate two distinct types of posttranscriptional regulation: degradation of mRNA targets via binding their 3'-UTR (group 1) and stabilization of mRNA targets through binding their CDS (group 2) (FIG. 3D).

Example 4. Disrupting MSI1/AGO2 Interaction Restrains Tumor Growth and Alters mRNA Regulation As MSI1 engages AGO2 to promote tumor progression through mRNA regulation, we asked whether the disruption of MSI1/AGO2 interaction could affect the tumor growth driven by cytosolic MSI1. To do so, we first mapped MSI1/AGO2 interaction using deletion mutants of MSI1 (FIG. 14A). We performed an in vitro binding assay by incubating the purified full-length, the N-terminal or C-terminal domain of MSI1 with purified AGO2 protein, and found that AGO2 preferentially interacted with the C-terminal domain of MSI1 (FIG. 14B). We next investigated whether the C-terminal domain of MSI1 (FIG. 4A) could act as a decoy to withdraw MSI1/AGO2 protein-protein interaction. Flag control (Flag) or Flag-tagged MSI1 C-terminus (Flag-C-term) were transiently expressed in GBM cells which were then subjected to immunoprecipitation against endogenous MSI1 in normal and hypoxic conditions. We found that overexpression of Flag-C-term disrupted the interaction between endogenous MSI1 and AGO2 (FIG. 4B), confirming the importance of the MSI1 C-terminal domain in this protein-protein interaction. Confocal microscopy further confirmed uncoupled co-localization of endogenous MSI1 and AGO2 in cells transfected with Flag-C-term (FIG. 4C). To precise the molecular mechanisms underlying the biological effects of Flag-C-term, we performed RIPqPCR experiments and demonstrated that Flag-C-term interfered with the recruitment of AGO2 to its mRNA targets, at both 3'UTR and CDS regions (FIG. 4D). We next analyzed the expression of MSI1/AGO2 mRNA targets and showed that, in cells transfected with Flag-C-term, the expression of mRNA targets from group 1 increased while that of targets from group 2 decreased after hypoxia compared to the control cells (FIG. 4E). We further evaluated the downstream effects of MSI1/AGO2 complex disruption by analyzing cell viability in cells transfected with Flag or Flag-C-term. Our results showed a decreased percentage of viable cells after Flag-C-term expression (FIG. 4F) which is consistent with the decreased number of soft agar colonies (FIG. 4G), and the increased percentage of Annexin V-positive cells (FIG. 4H). Taken together, these results indicated that, by disrupting MSI1/AGO2 interaction, Flag-C-term suppressed clonogenic growth and promoted apoptosis. To test the therapeutic potent of MSI1 C-terminus, we launched an in vivo study in which cancer cells were implanted on each flank of the mice subsequently subjected to an intratumoral transfection of Flag control or Flag-C-term (FIG. 4I). We observed that the growth of tumors derived either from MSI1-overexpressing GBM cells or MIA-PaCa2 pancreatic cancer cells was strongly delayed by the administration of Flag-C-term (FIG. 4J and FIG. 4K and FIG. 14C). Collectively, our findings demonstrated that disrupting MSI1/AGO2 interaction with MSI1-C-term decoy suppressed tumor growth by blocking the recruitment of AGO2 to its target mRNAs and subsequently altering their stability.

Example 5. Decoy Peptides Interfered the MSI1/AGO2 Association Through Binding AGO2

Based on our results with the C-terminus decoy, we then investigated the possibility of clinically using a smaller peptide to block tumor progression. To do so, we first precisely determined the interacting domain of MSI1 with AGO2 using a customized peptide array (PepSpot, JPT Inc.). This array was dotted with sequential peptides overlapping each other to cover the entire C-terminus of MSI1, and then incubated with recombinant AGO2 proteins. Among the twenty-seven peptides, AGO2 preferentially bound to peptides 11 and 26 (FIG. 5A). It was found that at least two peptides capable of binding to AGO2 have the amino acid sequences of YQFPEFRVERTPLPS and HSLGGPLI-ATAFTNG, respectively. Our candidate sequences were then associated with the HIV-1 Tat (48-60) cell-penetrating peptide (CPP) to facilitate cell uptake ability and improve in vivo transduction efficiency. We showed that the TAT-tagged peptides, namely TAT-11 and TAT-26, effectively abrogated the MSI1/AGO2 interaction (FIG. 5B). We next verified whether these peptides could be as efficient for in vivo studies. We developed a split luciferase complementation assay to detect in vivo protein-protein interactions. We split *Gaussia* luciferase (Gluc) into two fragments, N-terminus and C-terminus, which we respectively fused to MSI1 and AGO2. Upon MSI/AGO2 interaction, the two Glue fragments associate together to reconstitute the luciferase activity leading to light emission in the presence of the luciferase substrate (FIG. 14D). Using an In Vivo Imaging System (IVIS), we showed an increase of the bioluminescent signal in the presence of cisplatin (FIG. 14E and FIG. 14F), confirming the MSI1/AGO2 protein-protein interaction in vitro and in vivo under stress conditions. We next tested the inhibitory effect of TAT-11 and TAT-26 peptides, and showed that they dramatically turned down the bioluminescent signal in vitro and in vivo (FIG. 5C), indicating a decrease of interaction between MSI1 and AGO2 by peptide competition. To identify how decoy peptide bound to AGO2, we determined the structure of theses peptides in the complex with AGO2. We used molecular docking website (http://galaxy.seoklab.org/index.html) to predict the binding modes between peptide and AGO2. The crystal structure showed that TAT-11 and TAT-26 interacted with the PIWI domain of AGO2 through hydrogen bounds (FIG. 5D) without significant change of AGO2 structure. Confocal microscopy confirmed that the decoy peptides penetrated in cells and associated with the endogenous AGO2 in the cytosol (FIG. 5F). We also assessed the affinity between the peptides and AGO2 recombinant proteins by surface plasmon resonance (SPR), and showed that the equilibrium dissociation constant ($K_D$)) of TAT-11 and TAT-26 were 3.33 and 4.63 µM, respectively. Collectively, we identified specific binding sequence in MSI1 C-terminus for its association with AGO2, and peptides mimicking these sequences were able to bind to AOG2 and may disrupt the MSI1/AOG2 interaction in vitro.

Example 6. Decoy Peptides Blocking MSI1/AGO2 Interaction Suppress Tumor Progression To determine the efficiency of the decoy peptides on competing AGO2 with endogenous MSI1, a fluorescence-based detection using fluorescein labeled HIV-TAT peptide (TAT (FAM)) was conducted to assess the uptake rate, concentration (KC50) and stability in cells. The concentration of decoy peptides at half-maximal response (KC50) was around 9 µM (FIG. 6A and FIG. 6B). Besides, significant cellular uptake of TAT-11 and TAT-26 were found within one hour (FIGS. 15A and 15B); while the degradation half-life of TAT-11 and TAT-26 in 05 MG cells can reach up to 4 hours (FIGS. 15C and 15D). Moreover, the effect of MSI1/AGO2 binding on downstream mRNA was reversed by TAT-11 and TAT-26 peptides (FIG. 16A). To estimate the potential of a peptide therapy, MSI1-overexpressed 05 MG cells, MIA-PaCa2 pancreatic cancer cells, Pt 3 and Pt 11 primary GBM cells were subcutaneously transplanted into mice. Once the tumors were detectable, we then performed an intratumoral injection of combined TAT-11/TAT-26 peptides (150 µg) and observed that the growth of tumors derived either from MSI1-overexprssed GBM cells, parental GBM (Pt 3 and Pt 11) or pancreatic cancer (MIA-PaCa2) was strongly decreased by peptide injection (FIGS. 6C, 6D and 6E). Immunostaining of the tumor tissues confirmed that endogenous MSI1 and AGO2 remained in cytosol without interaction under peptide treatment (FIG. 16B and FIG. 16C). In addition, an orthotopic xenograft mouse model was developed and the combined TAT-11/TAT-26 peptides were then injected within the tumor sites (FIG. 6F). The tumor size in mice treated with TAT-11/TAT-26 peptides was strongly reduced compared to that of the control mice (FIG. 6G). Moreover, tumors injected with peptides displayed a severe reduction of Ki67 expression, a marker associated with cell proliferation (FIG. 6G, right panel). Interestingly, mice, transplanted with either 05 MG cell line or primary cultured cells from recurrent GBM tumor, treated with TAT-11/TAT-26 peptides and subjected to cisplatin treatment exhibited a significant prolonged life span comparing to control groups (FIG. 6H), suggesting that TAT-11/TAT-26 peptides could enhance the sensitivity of tumor cells to chemotherapy drugs by blocking MSI1/AGO2 interaction. Similar results on tumor growth were obtained with injection of TAT-11/TAT-26 peptides in a pancreatic tumor xenograft mouse model (FIG. 6I-6L). Analysis of the xenograft tumor samples indicated the effectiveness of TAT-11/TAT-26 peptides on tumor growth (FIG. 6J), MSI1/AGO2 interaction (FIG. 6K), and the downstream mRNA targets (FIG. 6L). Taken together, our results demonstrated the strong therapeutic potential of small peptides blocking MSI1/AGO2 interaction, on tumor growth and sensitivity to chemotherapy drugs.

Example 7. The MSI1/AGO2 Pathway is Enhanced in Patients with Tumor Relapse

Cytosolic MSI1 engages AGO2 to promote stress-induced tumor growth through RNA regulation. We showed that a significant proportion of MSI1 was cytosolic in samples from patients with high grade glioma (FIG. 1A) but it remains unclear whether MSI1/AGO2 pathway actively participates to tumorigenicity in patients and could also have an impact on tumor recurrence. To address this point, we collected eighteen pairs of primary and recurrent GBM samples from patients who received concurrent chemotherapeutics after primary surgery (Supplementary Table 1) and analyzed the subcellular localization of MSI1 by IHC staining. We showed that a significant proportion of MSI1 proteins were cytosolic in the GBM recurrent samples whereas MSI1 was barely detectable in the cytosol in the primary GBM samples (FIG. 7A). We then collected by laser capture microdissection (LCM) tissue samples from the tumor (T) and non-tumor stroma (S)[26] and analyzed the expression level of MSI1 target mRNAs by qPCR. We observed that, for each pair of samples, the expression of mRNA targets related to apoptosis (group 1) was decreased in recurrent GBM compared to the primary GBM while the expression of the mRNA targets related to cell cycle (group 2) was increased (FIG. 7B). The same results were also observed in a follow-up of a cohort of primary (n=67) and recurrent (n=32) GBM patients (FIG. 7C and Supplementary Table 2). These results indicated that, in patients with recurrent GBM, the MSI1/AGO2 pathway was enhanced to promote tumor growth and ensure cancer cell survival.

SUPPLEMENTARY TABLE 1

Clinical manifestation and background of 18 GBM patients with primary and recurrent tumors.

|  | Recurrent GBM |
| --- | --- |
| No. of patients | 18 |
| Age (years) | 62.1 ± 5.7 |
| Female | 16 |
| Survival (months) | 4.1 ± 0.2 |
| KPS |  |
| ≥80 | 0 |
| <80 | 18 |
| P53 mutation | 14 |
| MGMT methylation | 11 |
| Surgery |  |
| Total gross removal | 18 |
| Subtotal removal | 0 |
| No surgery | 0 |
| Radiation | 18 |
| Treatment with Temodal ® | 18 |

SUPPLEMENTARY TABLE 2

Clinical manifestation and clinical background of a cohort of 67 primary and 32 recurrent GBM patients.

|  | GBM | Recurrent GBM |
| --- | --- | --- |
| No. of patients | 67 | 32 |
| Age (years) | 60.2 ± 6.5 | 64.6 ± 5.1 |
| Female | 30 | 18 |
| Survival (months) | 15.3 ± 1.6 | 6.2 ± 1.1 |
| KPS |  |  |
| ≥80 | 29 | 0 |
| <80 | 38 | 32 |
| P53 mutation | 60 | 25 |
| MGMT methylation | 41 | 19 |
| Surgery |  |  |
| Total gross removal | 65 | 31 |
| Subtotal removal | 0 | 0 |
| No surgery | 2 | 1 |
| Radiation | 67 | 32 |
| Temodal ® | 67 | 32 |

To address whether the correlation between MSI1/AGO2 pathway and tumor recurrence could be generalized to other cancer types, we collected samples from patients with pancreatic ductal adenocarcinoma (PDAC) and performed IHC staining of MSI1 on non-recurrent (n=18) and recurrent (n=61) PDAC samples (Supplementary Table 3). We observed that around 5% of non-recurrent pancreatic samples exhibited MSI1 in the cytosol (1/18 cases; data not shown) while 60% of recurrent PDAC samples (37/61 cases) displayed cytosolic MSI1 (FIG. 7D), suggesting that cytosolic MSI1 was associated with tumor recurrence. By analyzing clinical data of the recurrent PDAC samples, we observed that patients with recurrent PDAC positive for cytosolic MSI1 presented overall a lower survival than those negative for cytosolic MSI1 (FIG. 7E). We further analyzed the 37 recurrent PDAC cases positive for cytosolic MSI1 and classified them based on IHC staining score (IHC<0.5 or IHC>0.5). We showed that the group of patients with high score (IHC>0.5) exhibited a lower survival outcome than that with low score (IHC<0.5) (FIG. 7F and FIG. 7G), suggesting that level of cytosolic MSI1 could predict patient survival. Collectively, the results indicated that the cytosolic MSI1/AGO2 pathway is enhanced in patients with tumor relapse and engages patient survival, leading open the possibility to use small peptides blocking MSI1/AGO2 interaction as therapeutic sensitizer for tumor recurrence treatment (FIG. 8).

SUPPLEMENTARY TABLE 3

Clinical manifestation and clinical background of a cohort of 61 recurrent PDAC patients.

|  | Non-recurrent | Recurrent |
| --- | --- | --- |
| No. of patients | 18 | 61 |
| Age (years) | 64.6 ± 12.4 | 67.8 ± 13 |
| Sex |  |  |
| Female | 6 | 22 |
| Male | 12 | 39 |
| Survival (months) |  |  |
| DFS | 62.87 | 10.3 |
| OS | 88.9 | 21 |
| AJCC TNM status |  |  |
| Stage 0 | 0 | 0 |
| Stage IA | 2 | 0 |

SUPPLEMENTARY TABLE 3-continued

Clinical manifestation and clinical background of a cohort of 61 recurrent PDAC patients.

|  | Non-recurrent | Recurrent |
|---|---|---|
| Stage IB | 3 | 7 |
| Stage IIA | 8 | 14 |
| Stage IIB | 5 | 37 |
| Stage III | 0 | 3 |
| Stage IV | 0 | 0 |

The descriptions and claims as provided should be understood as of demonstrative purpose instead of limitative in any way to the scope of the present invention.

REFERENCES

1. Gerstberger, S., Hafner, M. & Tuschl, T. A census of human RNA-binding proteins. *Nature reviews. Genetics* 15, 829-845 (2014).
2. Muller-McNicoll, M. & Neugebauer, K. M. How cells get the message: dynamic assembly and function of mRNA-protein complexes. *Nature reviews. Genetics* 14, 275-287 (2013).
3. Ascano, M., Gerstberger, S. & Tuschl, T. Multi-disciplinary methods to define RNA-protein interactions and regulatory networks. *Current opinion in genetics & development* 23, 20-28 (2013).
4. Henras, A. K., et al. The post-transcriptional steps of eukaryotic ribosome biogenesis. *Cellular and molecular life sciences: CMLS* 65, 2334-2359 (2008).
5. Musunuru, K. Cell-specific RNA-binding proteins in human disease. *Trends in cardiovascular medicine* 13, 188-195 (2003).
6. Dreyfuss, G., Kim, V. N. & Kataoka, N. Messenger-RNA-binding proteins and the messages they carry. *Nature reviews. Molecular cell biology* 3, 195-205 (2002).
7. Hadziselimovic, N., et al. Forgetting is regulated via Musashi-mediated translational control of the Arp2/3 complex. *Cell* 156, 1153-1166 (2014).
8. Rentas, S., et al. Musashi-2 attenuates AHR signalling to expand human haematopoietic stem cells. *Nature* 532, 508-511 (2016).
9. Fox, R. G., Park, F. D., Koechlein, C. S., Kritzik, M. & Reya, T. Musashi signaling in stem cells and cancer. *Annual review of cell and developmental biology* 31, 249-267 (2015).
10. Fox. R. G., et al. Image-based detection and targeting of therapy resistance in pancreatic adenocarcinoma. *Nature* 534, 407-411 (2016).
11. Liu, X., Yang, W. T. & Zheng, P. S. Msi1 promotes tumor growth and cell proliferation by targeting cell cycle checkpoint proteins p21, p27 and p53 in cervical carcinomas. *Oncolarget* 5, 10870-10885 (2014).
12. Kawahara, H., et al. Musashi1 cooperates in abnormal cell lineage protein 28 (Lin28)-mediated let-7 family microRNA biogenesis in early neural differentiation. *J Biol Chem* 286, 16121-16130 (2011).
13. Sureban, S. M., et al. Knockdown of RNA binding protein musashi-1 leads to tumor regression in vivo. *Gastroenterology* 134, 1448-1458 (2008).
14. Moreira, A. L., Gonen, M., Rekhtman, N. & Downey, R. J. Progenitor stem cell marker expression by pulmonary carcinomas. *Modern pathology: an official journal of the United States and Canadian Academy of Pathology. Inc* 23, 889-895 (2010).
15. Kanemura, Y., et al. Musashi1, an evolutionarily conserved neural RNA-binding protein, is a versatile marker of human glioma cells in determining their cellular origin, malignancy, and proliferative activity. *Differentiation; research in biological diversity* 68, 141-152 (2001).
16. Wang, T., et al. Sequential expression of putative stem cell markers in gastric carcinogenesis. *Br J Cancer* 105, 658-665 (2011).
17. Shu, H. J., et al. Expression of the Musashi1 gene encoding the RNA-binding protein in human hepatoma cell lines. *Biochem Biophys Res Commun* 293, 150-154 (2002).
18. Dahlrot, R. H., et al. Prognostic value of Musashi-1 in gliomas. *Journal of neuro-oncology* 115, 453-461 (2013).
19. Meister, G. Argonaute proteins: functional insights and emerging roles. *Nature reviews. Genetics* 14, 447-459 (2013).
20. Wee, L. M., Flores-Jasso. C. F., Salomon, W. E. & Zamore, P. D. Argonaute divides its RNA guide into domains with distinct functions and RNA-binding properties. *Cell* 151, 1055-1067 (2012).
21. Golden, R. J., et al. An Argonaute phosphorylation cycle promotes microRNA-mediated silencing. *Nature* 542, 197-202 (2017).
22. Shen. J., et al. EGFR modulates microRNA maturation in response to hypoxia through phosphorylation of AGO2. *Nature* 497, 383-387 (2013).
23. Karginov, F. V. & Hannon. G. J. Remodeling of Ago2-mRNA interactions upon cellular stress reflects miRNA complementarity and correlates with altered translation rates. *Genes Dev* 27, 1624-1632 (2013).
24. MacNicol, A. M., Wilczynska, A. & MacNicol, M. C. Function and regulation of the mammalian Musashi mRNA translational regulator. *Biochemical Society transactions* 36, 528-530 (2008).
25. Du, Y., et al. Blocking c-Met-mediated PARP1 phosphorylation enhances anti-tumor effects of PARP inhibitors. *Nature medicine* 22, 194-201 (2016).
26. Chiou, G. Y., et al. Epigenetic regulation of the miR142-3p/interleukin-6 circuit in glioblastoma. *Mol Cell* 52, 693-706 (2013).
27. Wang-Gillam, A., et al. Nanoliposomal irinotecan with fluorouracil and folinic acid in metastatic pancreatic cancer after previous gemcitabine-based therapy (NAPOLI-1): a global, randomised, open-label, phase 3 trial. *Lancet* (London, England) 387, 545-557 (2016).
28. Lovci, M. T., Bengtson, M. H. & Massirer, K. B. Post-Translational Modifications and RNA-Binding Proteins. *Advances in experimental medicine and biology* 907, 297-317 (2016).
29. Lee, E. K. Post-translational modifications of RNA-binding proteins and their roles in RNA granules. *Current protein & peptide science* 13, 331-336 (2012).
30. Hammarskjold, M. L. & Rekosh, D. SR proteins: To shuttle or not to shuttle, that is the question. *The Journal of cell biology* 216, 1875-1877 (2017).
31. Detzer, A., Engel, C., Wunsche. W. & Sczakiel, G. Cell stress is related to re-localization of Argonaute 2 and to decreased RNA interference in human cells. *Nucleic acids research* 39, 2727-2741 (2011).
32. Tahbaz, N., et al. Characterization of the interactions between mammalian PAZ PIWI domain proteins and Dicer. *EMBO reports* 5, 189-194 (2004).
33. Collins, M., et al. The RNA-binding motif 45 (RBM45) protein accumulates in inclusion bodies in amyotrophic lateral sclerosis (ALS) and frontotemporal lobar degeneration with TDP-43 inclusions (FTLD-TDP) patients. *Acta neuropathologica* 124, 717-732 (2012).
34. Chang, Y. S., et al. Stapled alpha-helical peptide drug development: a potent dual inhibitor of MDM2 and MDMX for p53-dependent cancer therapy. *Proceedings of the National Academy of Sciences of the United States of America* 110, E3445-3454 (2013).
35. Becker, A., et al. Metabolism and disposition of the alphav-integrin ss3/ss5 receptor antagonist cilengitide, a cyclic polypeptide, in humans. *Journal of clinical pharmacology* 55, 815-824 (2015).
36. Liu, Z., et al. EGFRvIII/integrin beta3 interaction in hypoxic and vitronectinenriching microenvironment promote GBM progression and metastasis. *Oncotarget* 7, 4680-4694 (2016).
37. Stupp, R., et al. Cilengitide combined with standard treatment for patients with newly diagnosed glioblastoma with methylated MGMT promoter (CENTRIC EORTC 26071-22072 study): a multicentre, randomised, open-label, phase 3 trial. *Lancet Oncol* 15, 1100-1108 (2014).
38. Chiou, G. Y., et al. Epigenetic regulation of the miR142-3p/interleukin-6 circuit in glioblastoma. *Mol Cell* 52, 693-706 (2013).
39. Kawahara, H., et al. Musashi1 cooperates in abnormal cell lineage protein 28 (Lin28)-mediated let-7 family microRNA biogenesis in early neural differentiation. *J Biol Chem* 286, 16121-16130 (2011).
40. Roberts, A. & Pachter, L. Streaming fragment assignment for real-time analysis of sequencing experiments. *Nat Methods* 10, 71-73 (2013).
41. Langmead, B., Trapnell, C., Pop, M. & Salzberg, S. L. Ultrafast and memory-efficient alignment of short DNA sequences to the human genome. *Genome Biol* 10, R25 (2009).
42. Keene, J. D., Komisarow, J. M. & Friedersdorf, M. B. RIP-Chip: the isolation and identification of mRNAs, microRNAs and protein components of ribonucleoprotein complexes from cell extracts. *Nature protocols* 1, 302-307 (2006).
43. Dahm, G. M., et al. Method for the isolation and identification of mRNAs, microRNAs and protein components of ribonucleoprotein complexes from cell extracts using RIP-Chip. *Journal of visualized experiments: JoVE* (2012).
44. Selth, L. A., Gilbert, C. & Svejstrup, J. Q. RNA immunoprecipitation to determine RNA-protein associations in vivo. *Cold Spring Harbor protocols* 2009, pdb prot5234 (2009).
45. Raj, A., van den Bogaard, P., Rifkin, S. A., van Oudenaarden, A. & Tyagi, S. Imaging individual mRNA molecules using multiple singly labeled probes. *Nature methods* 5, 877-879 (2008).
46. Shen, J., et al. EGFR modulates microRNA maturation in response to hypoxia through phosphorylation of AGO2. *Nature* 497, 383-387 (2013).
47. Karpova, T. & McNally, J. G. Detecting protein-protein interactions with CFP-YFP FRET by acceptor photobleaching. *Current protocols in cytometry/editorial board, J. Paul Robinson, managing editor . . . [et al.]* Chapter 12, Unit12 17 (2006).
48. Jiang, B. H., et al. CHD1L Regulated PARP1-Driven Pluripotency and Chromatin Remodeling During the Early-Stage Cell Reprogramming. *Stem cells* 33, 2961-2972 (2015).
49. Li, R., et al. Identification of an epitope in the C terminus of normal prion protein whose expression is modulated by binding events in the N terminus. *J Mol Biol* 301, 567-573 (2000).
50. Abes, R., et al. Arginine-rich cell penetrating peptides: design, structure-activity, and applications to alter pre-mRNA splicing by steric-block oligonucleotides. *J Pept Sci* 14, 455-460 (2008).
51. Jones, S. W., et al. Characterisation of cell-penetrating peptide-mediated peptide delivery. *Br J Pharmacol* 145, 1093-1102 (2005).
52. Thoren, P. E., et al. Uptake of analogs of penetratin, Tat (48-60) and oligoarginine in live cells. *Biochem Biophys Res Commun* 307, 100-107 (2003).
53. Kato, N. & Jones, J. The split luciferase complementation assay. *Methods Mol Biol* 655, 359-376 (2010).
54. Paulmurugan, R., Umezawa, Y. & Gambhir, S. S. Non-invasive imaging of protein-protein interactions in living subjects by using reporter protein complementation and reconstitution strategies. *Proc Natl Acad Sci USA* 99, 15608-15613 (2002).
55. Trinh, R., Gurbaxani, B., Morrison, S. L. & Seyfzadeh, M. Optimization of codon pair use within the (GGGGS)3 linker sequence results in enhanced protein expression. *Mol Immunol* 40, 717-722 (2004).
56. Newton, D. L., Xue, Y., Olson, K. A., Fett, J. W. & Rybak, S. M. Angiogenin single-chain immunofusions: influence of peptide linkers and spacers between fusion protein domains. *Biochemistry* 35, 545-553 (1996).
57. Lin, L. T., et al. A comparative study of primary and recurrent human glioblastoma multiforme using the small animal imaging and molecular expressive profiles. *Molecular imaging and biology: MIB: the official publication of the Academy of Molecular Imaging* 15, 262-272 (2013).
58. Chien, C. S., et al. Lin28B/Let-7 Regulates Expression of Oct4 and Sox2 and Reprograms Oral Squamous Cell Carcinoma Cells to a Stem-like State. *Cancer research* 75, 2553-2565 (2015).

We claim:

1. A method for blocking stress-induced tumor progression in a subject comprising:
administering to said subject a pharmaceutical composition comprising a therapeutically effective amount of a Musashi-1 (MSI1) decoy peptide consisting of the amino acid sequence of SEQ ID NO: 284 or SEQ ID NO: 299 to disrupt MSI1/Argonaute 2 (AGO2) interaction, and a pharmaceutically acceptable carrier.

2. A method for treating a tumor progression or a tumor recurrence, comprising
administering to a subject in need thereof a pharmaceutical composition comprising a therapeutically effective amount of a Musashi-1 (MSI1) decoy peptide consisting of the amino acid sequence of SEQ ID NO: 284 or SEQ ID NO: 299 to disrupt MSI1/Argonaute 2 (AGO2) interaction, and a pharmaceutically acceptable carrier.

* * * * *

SEQUENCE LISTING

<160> NUMBER OF SEQ ID NOS: 312

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
atggagactg acgcgcccca gcccg                                    25

```
<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
tcagtggtac ccattggtga aggct                                              25

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
agaagcttat ggagactgac gcgccccagc                                         30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
aggatcctca gtggtaccca ttggtgaagg                                         30

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
cgggaccccc tgaccgcagc atccgcaggt ttcggcttcg tc                           42

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
gacgaagccg aaacctgcgg atgctgcggt caggggtcc cg                            42

<210> SEQ ID NO 7
<211> LENGTH: 48
<212> TYPE: DNA
<213> ORGANISM: Artificial Sequence
<220> FEATURE:
<223> OTHER INFORMATION: Primer

<400> SEQUENCE: 7
cccaagatgg tgactgcaac ggcagcaatc tttgtggggg gctgtcg                      48

<210> SEQ ID NO 8
<211> LENGTH: 48
<212> TYPE: DNA
<213> ORGANISM: Artificial Sequence
<220> FEATURE:
<223> OTHER INFORMATION: Primer
```

<400> SEQUENCE: 8
cgacagcccc cccacaaaga ttgctgccgt tgcagtcacc atcttggg         48

<210> SEQ ID NO 9
<211> LENGTH: 48
<212> TYPE: DNA
<213> ORGANISM: Artificial Sequence
<220> FEATURE:
<223> OTHER INFORMATION: Primer

<400> SEQUENCE: 9
ccagtcctcc ccgaggcaac agccgcacct gcaactgcct acggacca         48

<210> SEQ ID NO 10
<211> LENGTH: 48
<212> TYPE: DNA
<213> ORGANISM: Artificial Sequence
<220> FEATURE:
<223> OTHER INFORMATION: Primer

<400> SEQUENCE: 10
tggtccgtag gcagttgcag gtgcggctgt tgcctcgggg aggactgg         48

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
atcgaagctt tgccctacgg aatggacgcc         30

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
taagggatcc tcagtggtac ccattggt         28

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
aattaagctt atggagactg acgcgcccca g         31

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
ttaaggatcc aactgctgac ccccgagtcc         30

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
ttaaggatcc atggctgtaa gctcgggg                               28

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
ttaaggatcc aactccggct ggcgtagg                               28

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
ttaggatccc cgttggcgac atcacct                                27

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ttgacaaaac caccaaccgg                                        20

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
cctcctttgg ctgagctttc tt                                     22

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
agtaccctct cagctccagg                                        20

<210> SEQ ID NO 21
<211> LENGTH: 20
<212> TYPE: DNA
<213> ORGANISM: Artificial Sequence
<220> FEATURE:
<223> OTHER INFORMATION: Primer

```
<400> SEQUENCE: 21
tgtctgactc cttgttccgc                                              20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
ggcaggaagg ctccagatg                                               19

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
cctcactgtt catatgccca ttc                                          23

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gaagttgcaa agtcctggag c                                            21

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
tggtttccac ttcgcagca                                               19

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tcgtcgaaag cctctcttct g                                            21

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aggcagagat tcgcttgtgt                                              20
```

```
<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
gaattccggg acccgttgg                                                      19

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ccaagtctgg ctcgttctca                                                     20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gcagcacgtg tacgagaaga                                                     20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cctccaagct atcgtccagc                                                     20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ccaggatttg gctacggagg                                                     20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
taggtaacag gggcaagtgg                                                     20

<210> SEQ ID NO 34
<211> LENGTH: 20
<212> TYPE: DNA
<213> ORGANISM: Artificial Sequence
<220> FEATURE:
<223> OTHER INFORMATION: Primer
```

<400> SEQUENCE: 34
aggcgggtta ggaagagtgg                                              20

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
gaccatatgg acataggccc c                                            21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
tgggttcctc tgcagacatt c                                            21

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
gctccttgta atggggagac c                                            21

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
cagttcaatt ctgtgcccgc                                              20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gctccttctt ggctcaaggt                                              20

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
ttcccgggtg agtgtccag                                               19

```
<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
tatcccaaga catgcgagcc                                              20

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
ttcttgctgg tggagtagca g                                            21

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
tagacctggt gaatcaagaa gg                                           22

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
actgaagcct aagaaggcac c                                            21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ctccaggaga ggtgaggacc                                              20

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
gcgtgacatt aaggagaag                                               19

<210> SEQ ID NO 47
<211> LENGTH: 18
<212> TYPE: DNA
<213> ORGANISM: Artificial Sequence
<220> FEATURE:
<223> OTHER INFORMATION: Primer
```

<400> SEQUENCE: 47
gaaggaaggc tggaagag                                              18

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
agaaggctgg ggctcatttg                                            20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
aggggccatc cacagtcttc                                            20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cagccacccg agattgagca                                            20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
tagtagcgac gggcggtgtg                                            20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
ctaataaagc gggaggggcg                                            20

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
gtcctatttc agtagtacag acgc                                       24

```
<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
gtggtgggct agacgagttt c                                              21

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
cttgcggtgg gtaactggag                                                20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ggcacagacc agagctgatt                                                20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tccagcatct tggggatgtc                                                20

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
tcgacctgga gggctgtatt a                                              21

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
caggaccatg gtgttcccac                                                20

<210> SEQ ID NO 60
<211> LENGTH: 20
<212> TYPE: DNA
<213> ORGANISM: Artificial Sequence
<220> FEATURE:
<223> OTHER INFORMATION: Primer
```

<400> SEQUENCE: 60
acctgcctac cttgcagaga                                                      20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
cttccccgtg acacgttagt                                                      20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
aaaggaggac ctctcgccaa                                                      20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
gctgaacaag acctgtgggg                                                      20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
tgatgcaatc cgctaggtcg                                                      20

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
gcatccgtta ctgcaatcct tc                                                   22

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gaaacgacct ggccgatgaa                                                      20

```
<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gctcccggtt actctgagac                                               20

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
cagtggtgct gggagtgtc                                                19

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
gatcagccat ggtgcgagc                                                19

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
agggaggtgt ttatgaggcg                                               20

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
acaaagctaa ccatgctgca a                                             21

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
gatgcagatg ggaacggga                                                19

<210> SEQ ID NO 73
<211> LENGTH: 20
<212> TYPE: DNA
<213> ORGANISM: Artificial Sequence
<220> FEATURE:
<223> OTHER INFORMATION: Primer
```

```
<400> SEQUENCE: 73
aaagacacgg aacgcctctc                                              20

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
ctcattgtgc ggctcctact aa                                           22

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
agaagagcac cgccttcttg                                              20

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
gcagaatcag aatgttccgg g                                            21

<210> SEQ ID NO 77
<211> LENGTH: 23
<212> TYPE: DNA
<213> ORGANISM: Artificial Sequence
<220> FEATURE:
<223> OTHER INFORMATION: Primer

<400> SEQUENCE: 77
cctggagttc cttttaccc tct                                           23

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
aatctgagga gctgggttgc                                              20

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
tgatgaactt ggctgcgtac t                                            21
```

```
<210> SEQ ID NO 80
<211> LENGTH: 19
<212> TYPE: DNA
<213> ORGANISM: Artificial Sequence
<220> FEATURE:
<223> OTHER INFORMATION: Primer

<400> SEQUENCE: 80
tcgatgcgtt tgcacaaga                                                19

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
ctggggtgtc tccttcactc                                               20

<210> SEQ ID NO 82
<211> LENGTH: 21
<212> TYPE: DNA
<213> ORGANISM: Artificial Sequence
<220> FEATURE:
<223> OTHER INFORMATION: Primer

<400> SEQUENCE: 82
cctatcggaa gcttgccttg a                                             21

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
cagctggaca gcacgaagta                                               20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
ctggatggcg ggtttcagat                                               20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
agttgggtcc ctcctcaagt                                               20

<210> SEQ ID NO 86
<211> LENGTH: 20
<212> TYPE: DNA
<213> ORGANISM: Artificial Sequence
<220> FEATURE:
<223> OTHER INFORMATION: Primer
```

<400> SEQUENCE: 86 ccattcggggg agactctggt					20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
acctccatag agctccgact					20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
gctcgggtcc taatcacccc					20

<210> SEQ ID NO 89
<211> LENGTH: 21
<212> TYPE: DNA
<213> ORGANISM: Artificial Sequence
<220> FEATURE:
<223> OTHER INFORMATION: Primer

<400> SEQUENCE: 89
tgcatctcct gtctcgaagt c					21

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
tttgggcatc aggagaacgc					20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
caacatcgtt gcgacacacc					20

<210> SEQ ID NO 92
<211> LENGTH: 21
<212> TYPE: DNA
<213> ORGANISM: Artificial Sequence
<220> FEATURE:
<223> OTHER INFORMATION: Primer

<400> SEQUENCE: 92
agaccagatc tccttcgctg a					21

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
tcactgtttc ccgttgccat                                               20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
gagtggcttt gagaagcacc                                               20

<210> SEQ ID NO 95
<211> LENGTH: 21
<212> TYPE: DNA
<213> ORGANISM: Artificial Sequence
<220> FEATURE:
<223> OTHER INFORMATION: Primer

<400> SEQUENCE: 95
tctagcctct cgtacacctg g                                             21

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
ctggaagtgt tgcagaggtg t                                             21

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
ccgtcagctg ccatgtagtt                                               20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gatcttacag gagcgagcgg                                               20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
tgtgcttgcg gaccttcatt                                               20

<210> SEQ ID NO 100
<211> LENGTH: 19
<212> TYPE: DNA
<213> ORGANISM: Artificial Sequence
<220> FEATURE:
<223> OTHER INFORMATION: Primer

<400> SEQUENCE: 100
ttctgccgag agccgaaga                                                19

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
ttcaaggcaa tggagccagg                                               20

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
ttccagtaag gagtcggggt                                               20

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
cctccttctc cgtagccaaa                                               20

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
cagcaggaat catcggactc a                                             21

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
tgtggcgttt tctttgtcgt                                               20

```
<210> SEQ ID NO 106
<211> LENGTH: 21
<212> TYPE: DNA
<213> ORGANISM: Artificial Sequence
<220> FEATURE:
<223> OTHER INFORMATION: Primer

<400> SEQUENCE: 106
gaaggtgaag cgcaatgtcc c                                       21

<210> SEQ ID NO 107
<211> LENGTH: 21
<212> TYPE: DNA
<213> ORGANISM: Artificial Sequence
<220> FEATURE:
<223> OTHER INFORMATION: Primer

<400> SEQUENCE: 107
gttcttctgt ggtaacgggg t                                       21

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
cttctttgac cggaacacgc                                         20

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
agtacttgac agcgtggagc                                         20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
aaggaaccat ggccaactgt                                         20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
agatcttcgg aagcttgcat                                         20

<210> SEQ ID NO 112
<211> LENGTH: 20
<212> TYPE: DNA
<213> ORGANISM: Artificial Sequence
<220> FEATURE:
<223> OTHER INFORMATION: Primer
```

<400> SEQUENCE: 112
actccagcca aaaatgcaca            20

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
catgtagtgc ccaggactgt            20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
cggttgtgaa ctaaaggccg            20

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
tttgcaccag cccctaaact            20

<210> SEQ ID NO 116
<211> LENGTH: 24
<212> TYPE: DNA
<213> ORGANISM: Artificial Sequence
<220> FEATURE:
<223> OTHER INFORMATION: Primer

<400> SEQUENCE: 116
acgagatgaa ctaaatcgag ctat            24

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
tgaccaagag gtccacctga            20

<210> SEQ ID NO 118
<211> LENGTH: 21
<212> TYPE: DNA
<213> ORGANISM: Artificial Sequence
<220> FEATURE:
<223> OTHER INFORMATION: Primer

<400> SEQUENCE: 118
agctcatcag gtggtggaag a            21

```
<210> SEQ ID NO 119
<211> LENGTH: 21
<212> TYPE: DNA
<213> ORGANISM: Artificial Sequence
<220> FEATURE:
<223> OTHER INFORMATION: Primer

<400> SEQUENCE: 119
cggaggatta gctgttcgag g                                              21

<210> SEQ ID NO 120
<211> LENGTH: 23
<212> TYPE: DNA
<213> ORGANISM: Artificial Sequence
<220> FEATURE:
<223> OTHER INFORMATION: Primer

<400> SEQUENCE: 120
acctattctg agtttgcgaa gga                                            23

<210> SEQ ID NO 121
<211> LENGTH: 21
<212> TYPE: DNA
<213> ORGANISM: Artificial Sequence
<220> FEATURE:
<223> OTHER INFORMATION: Primer

<400> SEQUENCE: 121
tgatcagggc ttctcaggac t                                              21

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ccccacggag atcattgctt                                                20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
aaaggcccct gaacgagatg                                                20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
ttcccagagt tgtgacagcc                                                20

<210> SEQ ID NO 125
<211> LENGTH: 20
<212> TYPE: DNA
<213> ORGANISM: Artificial Sequence
<220> FEATURE:
<223> OTHER INFORMATION: Primer
```

<400> SEQUENCE: 125
gccagaaccc atggtgacat                                              20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
cgcgagttgg tctgggaaaa                                              20

<210> SEQ ID NO 127
<211> LENGTH: 22
<212> TYPE: DNA
<213> ORGANISM: Artificial Sequence
<220> FEATURE:
<223> OTHER INFORMATION: Primer

<400> SEQUENCE: 127
cctcttcaga cagctcctgt tc                                           22

<210> SEQ ID NO 128
<211> LENGTH: 21
<212> TYPE: DNA
<213> ORGANISM: Artificial Sequence
<220> FEATURE:
<223> OTHER INFORMATION: Primer

<400> SEQUENCE: 128
aagtgtatct ggtgagtggg c                                            21

<210> SEQ ID NO 129
<211> LENGTH: 21
<212> TYPE: DNA
<213> ORGANISM: Artificial Sequence
<220> FEATURE:
<223> OTHER INFORMATION: Primer

<400> SEQUENCE: 129
ggagtgatga gaaaccggag a                                            21

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
cgttagtcca cggtctggtc                                              20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
accagtttct tccggatggc                                              20

```
<210> SEQ ID NO 132
<211> LENGTH: 18
<212> TYPE: DNA
<213> ORGANISM: Artificial Sequence
<220> FEATURE:
<223> OTHER INFORMATION: Primer

<400> SEQUENCE: 132
ttctggaagg aacgccgc                                                     18

<210> SEQ ID NO 133
<211> LENGTH: 20
<212> TYPE: DNA
<213> ORGANISM: Artificial Sequence
<220> FEATURE:
<223> OTHER INFORMATION: Primer

<400> SEQUENCE: 133
tggtgtggaa cactagggga                                                   20

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
gaagggtcta aaggtgcggg                                                   20

<210> SEQ ID NO 135
<211> LENGTH: 20
<212> TYPE: DNA
<213> ORGANISM: Artificial Sequence
<220> FEATURE:
<223> OTHER INFORMATION: Primer

<400> SEQUENCE: 135
atgctgaaac ctggcctacc                                                   20

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
gcgagttaca ccaaccagga                                                   20

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
ccctctggaa agccaaacct                                                   20

<210> SEQ ID NO 138
<211> LENGTH: 20
<212> TYPE: DNA
<213> ORGANISM: Artificial Sequence
<220> FEATURE:
<223> OTHER INFORMATION: Primer
```

<400> SEQUENCE: 138
aagcacccaa gattcagcgt                                           20

<210> SEQ ID NO 139
<211> LENGTH: 22
<212> TYPE: DNA
<213> ORGANISM: Artificial Sequence
<220> FEATURE:
<223> OTHER INFORMATION: Primer

<400> SEQUENCE: 139
tagcctcctt cattctcttg gc                                        22

<210> SEQ ID NO 140
<211> LENGTH: 19
<212> TYPE: DNA
<213> ORGANISM: Artificial Sequence
<220> FEATURE:
<223> OTHER INFORMATION: Primer

<400> SEQUENCE: 140
gtagcttcgg cggagtctg                                            19

<210> SEQ ID NO 141
<211> LENGTH: 20
<212> TYPE: DNA
<213> ORGANISM: Artificial Sequence
<220> FEATURE:
<223> OTHER INFORMATION: Primer

<400> SEQUENCE: 141
agtcgacctc ttctgctgtc                                           20

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
cgaccgctat aaggccagtc                                           20

<210> SEQ ID NO 143
<211> LENGTH: 19
<212> TYPE: DNA
<213> ORGANISM: Artificial Sequence
<220> FEATURE:
<223> OTHER INFORMATION: Primer

<400> SEQUENCE: 143
gcagcttcga gccaatggt                                            19

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
acaaagatgg tgtggccgat                                           20

```
<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
aacgacttcc agcgtttcct                                              20

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
gggtggaaag agggaatgg                                               20

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
tgtgcatcgc tgattcgaga                                              20

<210> SEQ ID NO 148
<211> LENGTH: 20
<212> TYPE: DNA
<213> ORGANISM: Artificial Sequence
<220> FEATURE:
<223> OTHER INFORMATION: Primer

<400> SEQUENCE: 148
ccgtgaaggc ctaccttctg                                              20

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
tcctcgtcac tggaaaaggc                                              20

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
ccattgtctg aagggacggg                                              20

<210> SEQ ID NO 151
<211> LENGTH: 20
<212> TYPE: DNA
<213> ORGANISM: Artificial Sequence
<220> FEATURE:
<223> OTHER INFORMATION: Primer
```

```
<400> SEQUENCE: 151
gacaagcgac aggcagtgta                                        20

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
agtccctgga aatgccagcc                                        20

<210> SEQ ID NO 153
<211> LENGTH: 21
<212> TYPE: DNA
<213> ORGANISM: Artificial Sequence
<220> FEATURE:
<223> OTHER INFORMATION: Primer

<400> SEQUENCE: 153
tgtctacact ggcctcgtag t                                      21

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
aggggctgca gaacaaatca                                        20

<210> SEQ ID NO 155
<211> LENGTH: 20
<212> TYPE: DNA
<213> ORGANISM: Artificial Sequence
<220> FEATURE:
<223> OTHER INFORMATION: Primer

<400> SEQUENCE: 155
agacagaaag cgcagggatt                                        20

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
gcgcttatcg aagtgtggtc                                        20

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
ttcccctaga cactcgctcc                                        20
```

```
<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
agtagtccct tctcggcgat                                                  20

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
gacgatcaca gcgatccaca                                                  20

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
atttccggct tctgggactc                                                  20

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
ccatcggtgt gggttaaggg                                                  20

<210> SEQ ID NO 162
<211> LENGTH: 19
<212> TYPE: DNA
<213> ORGANISM: Artificial Sequence
<220> FEATURE:
<223> OTHER INFORMATION: Primer

<400> SEQUENCE: 162
cccatctttg tccggcctc                                                   19

<210> SEQ ID NO 163
<211> LENGTH: 20
<212> TYPE: DNA
<213> ORGANISM: Artificial Sequence
<220> FEATURE:
<223> OTHER INFORMATION: Primer

<400> SEQUENCE: 163
ccagttgtcc accttgaagc                                                  20

<210> SEQ ID NO 164
<211> LENGTH: 21
<212> TYPE: DNA
<213> ORGANISM: Artificial Sequence
<220> FEATURE:
<223> OTHER INFORMATION: Primer
```

<400> SEQUENCE: 164
gggtgacggt gaagagcaga a         21

<210> SEQ ID NO 165
<211> LENGTH: 22
<212> TYPE: DNA
<213> ORGANISM: Artificial Sequence
<220> FEATURE:
<223> OTHER INFORMATION: Primer

<400> SEQUENCE: 165
tcagtgacaa tggggagttt cc         22

<210> SEQ ID NO 166
<211> LENGTH: 22
<212> TYPE: DNA
<213> ORGANISM: Artificial Sequence
<220> FEATURE:
<223> OTHER INFORMATION: Primer

<400> SEQUENCE: 166
ctccagcttc tgtataccct gc         22

<210> SEQ ID NO 167
<211> LENGTH: 22
<212> TYPE: DNA
<213> ORGANISM: Artificial Sequence
<220> FEATURE:
<223> OTHER INFORMATION: Primer

<400> SEQUENCE: 167
agtcagaggc cttttctagg at         22

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
ctgaacaagt tggcctgcac         20

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
gggacagctt ccctggttag         20

<210> SEQ ID NO 170
<211> LENGTH: 20
<212> TYPE: DNA
<213> ORGANISM: Artificial Sequence
<220> FEATURE:
<223> OTHER INFORMATION: Primer

<400> SEQUENCE: 170
ggcccacttc accgtactaa         20

```
<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
agggaacaag caccctcaag                                              20

<210> SEQ ID NO 172
<211> LENGTH: 20
<212> TYPE: DNA
<213> ORGANISM: Artificial Sequence
<220> FEATURE:
<223> OTHER INFORMATION: Primer

<400> SEQUENCE: 172
ggtcggtggg ttggtagttt                                              20

<210> SEQ ID NO 173
<211> LENGTH: 22
<212> TYPE: DNA
<213> ORGANISM: Artificial Sequence
<220> FEATURE:
<223> OTHER INFORMATION: Primer

<400> SEQUENCE: 173
agtcttggtg gatccagatc at                                           22

<210> SEQ ID NO 174
<211> LENGTH: 22
<212> TYPE: DNA
<213> ORGANISM: Artificial Sequence
<220> FEATURE:
<223> OTHER INFORMATION: Primer

<400> SEQUENCE: 174
accctgtctg acaacctctt gg                                           22

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
aggcagagat tcgcttgtgt                                              20

<210> SEQ ID NO 176
<211> LENGTH: 22
<212> TYPE: DNA
<213> ORGANISM: Artificial Sequence
<220> FEATURE:
<223> OTHER INFORMATION: Primer

<400> SEQUENCE: 176
accctgtctg acaacctctt gg                                           22

<210> SEQ ID NO 177
<211> LENGTH: 20
<212> TYPE: DNA
<213> ORGANISM: Artificial Sequence
<220> FEATURE:
<223> OTHER INFORMATION: Primer
```

<400> SEQUENCE: 177
atgaacctgt ggtcccagct                                              20

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
gccaccatgg ccagccaact                                              20

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
cacccctcag acacacaggt                                              20

<210> SEQ ID NO 180
<211> LENGTH: 20
<212> TYPE: DNA
<213> ORGANISM: Artificial Sequence
<220> FEATURE:
<223> OTHER INFORMATION: Primer

<400> SEQUENCE: 180
tgaagctccc agaatgccag                                              20

<210> SEQ ID NO 181
<211> LENGTH: 20
<212> TYPE: DNA
<213> ORGANISM: Artificial Sequence
<220> FEATURE:
<223> OTHER INFORMATION: Primer

<400> SEQUENCE: 181
gctgccctgg taggttttct                                              20

<210> SEQ ID NO 182
<211> LENGTH: 20
<212> TYPE: DNA
<213> ORGANISM: Artificial Sequence
<220> FEATURE:
<223> OTHER INFORMATION: Primer

<400> SEQUENCE: 182
tgtgacttgc acgtactccc                                              20

<210> SEQ ID NO 183
<211> LENGTH: 20
<212> TYPE: DNA
<213> ORGANISM: Artificial Sequence
<220> FEATURE:
<223> OTHER INFORMATION: Primer

<400> SEQUENCE: 183
accatcgcta tctgagcagc                                              20

<210> SEQ ID NO 184
<211> LENGTH: 20
<212> TYPE: DNA
<213> ORGANISM: Artificial Sequence
<220> FEATURE:
<223> OTHER INFORMATION: Primer

<400> SEQUENCE: 184
gacatagtgt ggtggtgccc                                           20

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185
acaaacacgc acctcaaagc                                           20

<210> SEQ ID NO 186
<211> LENGTH: 20
<212> TYPE: DNA
<213> ORGANISM: Artificial Sequence
<220> FEATURE:
<223> OTHER INFORMATION: Primer

<400> SEQUENCE: 186
tttgaggtgc gtgtttgtgc                                           20

<210> SEQ ID NO 187
<211> LENGTH: 21
<212> TYPE: DNA
<213> ORGANISM: Artificial Sequence
<220> FEATURE:
<223> OTHER INFORMATION: Primer

<400> SEQUENCE: 187
cccacggatc tgaagggtga a                                         21

<210> SEQ ID NO 188
<211> LENGTH: 20
<212> TYPE: DNA
<213> ORGANISM: Artificial Sequence
<220> FEATURE:
<223> OTHER INFORMATION: Primer

<400> SEQUENCE: 188
ttcacccttc agatccgtgg                                           20

<210> SEQ ID NO 189
<211> LENGTH: 21
<212> TYPE: DNA
<213> ORGANISM: Artificial Sequence
<220> FEATURE:
<223> OTHER INFORMATION: Primer

<400> SEQUENCE: 189
cagtggggaa caagaagtgg a                                         21

<210> SEQ ID NO 190
<211> LENGTH: 20
<212> TYPE: DNA
<213> ORGANISM: Artificial Sequence
<220> FEATURE:
<223> OTHER INFORMATION: Primer

```
<400> SEQUENCE: 190
agagctctag caggtgaccc                                                    20

<210> SEQ ID NO 191
<211> LENGTH: 22
<212> TYPE: DNA
<213> ORGANISM: Artificial Sequence
<220> FEATURE:
<223> OTHER INFORMATION: Primer

<400> SEQUENCE: 191
caggtcagag aactagaacg cc                                                 22

<210> SEQ ID NO 192
<211> LENGTH: 22
<212> TYPE: DNA
<213> ORGANISM: Artificial Sequence
<220> FEATURE:
<223> OTHER INFORMATION: Primer

<400> SEQUENCE: 192
atggcgttct agttctctga cc                                                 22

<210> SEQ ID NO 193
<211> LENGTH: 20
<212> TYPE: DNA
<213> ORGANISM: Artificial Sequence
<220> FEATURE:
<223> OTHER INFORMATION: Primer

<400> SEQUENCE: 193
atgatggcac tggcttctca                                                    20

<210> SEQ ID NO 194
<211> LENGTH: 20
<212> TYPE: DNA
<213> ORGANISM: Artificial Sequence
<220> FEATURE:
<223> OTHER INFORMATION: Primer

<400> SEQUENCE: 194
gaacattcat tcccccaccg                                                    20

<210> SEQ ID NO 195
<211> LENGTH: 20
<212> TYPE: DNA
<213> ORGANISM: Artificial Sequence
<220> FEATURE:
<223> OTHER INFORMATION: Primer

<400> SEQUENCE: 195
cgagtgccct gtaccatcag                                                    20

<210> SEQ ID NO 196
<211> LENGTH: 20
<212> TYPE: DNA
<213> ORGANISM: Artificial Sequence
<220> FEATURE:
<223> OTHER INFORMATION: Primer

<400> SEQUENCE: 196
tggctgggga gagactttag                                                    20
```

```
<210> SEQ ID NO 197
<211> LENGTH: 21
<212> TYPE: DNA
<213> ORGANISM: Artificial Sequence
<220> FEATURE:
<223> OTHER INFORMATION: Primer

<400> SEQUENCE: 197
cacacaggaa ggagcgtcta t                                              21

<210> SEQ ID NO 198
<211> LENGTH: 19
<212> TYPE: DNA
<213> ORGANISM: Artificial Sequence
<220> FEATURE:
<223> OTHER INFORMATION: Primer

<400> SEQUENCE: 198
cgcccataga cgctccttc                                                 19

<210> SEQ ID NO 199
<211> LENGTH: 21
<212> TYPE: DNA
<213> ORGANISM: Artificial Sequence
<220> FEATURE:
<223> OTHER INFORMATION: Primer

<400> SEQUENCE: 199
caaagtgagg cctgggtaca a                                              21

<210> SEQ ID NO 200
<211> LENGTH: 21
<212> TYPE: DNA
<213> ORGANISM: Artificial Sequence
<220> FEATURE:
<223> OTHER INFORMATION: Primer

<400> SEQUENCE: 200
ttgtacccag gcctcacttt g                                              21

<210> SEQ ID NO 201
<211> LENGTH: 20
<212> TYPE: DNA
<213> ORGANISM: Artificial Sequence
<220> FEATURE:
<223> OTHER INFORMATION: Primer

<400> SEQUENCE: 201
gccccagacc aaggagtgag                                                20

<210> SEQ ID NO 202
<211> LENGTH: 21
<212> TYPE: DNA
<213> ORGANISM: Artificial Sequence
<220> FEATURE:
<223> OTHER INFORMATION: Primer

<400> SEQUENCE: 202
ttttctccat ggctgatgct g                                              21

<210> SEQ ID NO 203
<211> LENGTH: 19
<212> TYPE: DNA
<213> ORGANISM: Artificial Sequence
<220> FEATURE:
<223> OTHER INFORMATION: Primer
```

```
<400> SEQUENCE: 203
agcagcccaa ccccattag                                            19

<210> SEQ ID NO 204
<211> LENGTH: 21
<212> TYPE: DNA
<213> ORGANISM: Artificial Sequence
<220> FEATURE:
<223> OTHER INFORMATION: Primer

<400> SEQUENCE: 204
ctgacctaat ggggttgggc t                                         21

<210> SEQ ID NO 205
<211> LENGTH: 22
<212> TYPE: DNA
<213> ORGANISM: Artificial Sequence
<220> FEATURE:
<223> OTHER INFORMATION: Primer

<400> SEQUENCE: 205
agagccagac ctcactttac aa                                        22

<210> SEQ ID NO 206
<211> LENGTH: 21
<212> TYPE: DNA
<213> ORGANISM: Artificial Sequence
<220> FEATURE:
<223> OTHER INFORMATION: Primer

<400> SEQUENCE: 206
tcagtcttga agcccatccc t                                         21

<210> SEQ ID NO 207
<211> LENGTH: 21
<212> TYPE: DNA
<213> ORGANISM: Artificial Sequence
<220> FEATURE:
<223> OTHER INFORMATION: Primer

<400> SEQUENCE: 207
cttggcactt cccagacttc a                                         21

<210> SEQ ID NO 208
<211> LENGTH: 21
<212> TYPE: DNA
<213> ORGANISM: Artificial Sequence
<220> FEATURE:
<223> OTHER INFORMATION: Primer

<400> SEQUENCE: 208
ctgaagtctg ggaagtgcca a                                         21

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
tcctgctact ggggcttgag                                           20
```

```
<210> SEQ ID NO 210
<211> LENGTH: 20
<212> TYPE: DNA
<213> ORGANISM: Artificial Sequence
<220> FEATURE:
<223> OTHER INFORMATION: Primer

<400> SEQUENCE: 210
tagggcctgg gagtttgtca                                           20

<210> SEQ ID NO 211
<211> LENGTH: 21
<212> TYPE: DNA
<213> ORGANISM: Artificial Sequence
<220> FEATURE:
<223> OTHER INFORMATION: Primer

<400> SEQUENCE: 211
gatgaacgaa gccatctgtg c                                         21

<210> SEQ ID NO 212
<211> LENGTH: 19
<212> TYPE: DNA
<213> ORGANISM: Artificial Sequence
<220> FEATURE:
<223> OTHER INFORMATION: Primer

<400> SEQUENCE: 212
cccccaacct gtgttgtcc                                            19

<210> SEQ ID NO 213
<211> LENGTH: 21
<212> TYPE: DNA
<213> ORGANISM: Artificial Sequence
<220> FEATURE:
<223> OTHER INFORMATION: Primer

<400> SEQUENCE: 213
gcagctggtt gtcagtctct g                                         21

<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214
gacgccgaga tggagttcaa                                           20

<210> SEQ ID NO 215
<211> LENGTH: 22
<212> TYPE: DNA
<213> ORGANISM: Artificial Sequence
<220> FEATURE:
<223> OTHER INFORMATION: Primer

<400> SEQUENCE: 215
tgaaaggtga ctggttcttc ct                                        22

<210> SEQ ID NO 216
<211> LENGTH: 20
<212> TYPE: DNA
<213> ORGANISM: Artificial Sequence
<220> FEATURE:
<223> OTHER INFORMATION: Primer
```

<400> SEQUENCE: 216
cagtgttcac aagcggggat						20

<210> SEQ ID NO 217
<211> LENGTH: 21
<212> TYPE: DNA
<213> ORGANISM: Artificial Sequence
<220> FEATURE:
<223> OTHER INFORMATION: Primer

<400> SEQUENCE: 217
cacaccgtac atctccaggt c						21

<210> SEQ ID NO 218
<211> LENGTH: 20
<212> TYPE: DNA
<213> ORGANISM: Artificial Sequence
<220> FEATURE:
<223> OTHER INFORMATION: Primer

<400> SEQUENCE: 218
tcccgtggaa tgaaatccga						20

<210> SEQ ID NO 219
<211> LENGTH: 22
<212> TYPE: DNA
<213> ORGANISM: Artificial Sequence
<220> FEATURE:
<223> OTHER INFORMATION: Primer

<400> SEQUENCE: 219
gctgaacttc caaagaatcg gc					22

<210> SEQ ID NO 220
<211> LENGTH: 20
<212> TYPE: DNA
<213> ORGANISM: Artificial Sequence
<220> FEATURE:
<223> OTHER INFORMATION: Primer

<400> SEQUENCE: 220
ttggctgaaa aggcccagat						20

<210> SEQ ID NO 221
<211> LENGTH: 20
<212> TYPE: DNA
<213> ORGANISM: Artificial Sequence
<220> FEATURE:
<223> OTHER INFORMATION: Primer

<400> SEQUENCE: 221
tgcttcagct gatctgcctc						20

<210> SEQ ID NO 222
<211> LENGTH: 20
<212> TYPE: DNA
<213> ORGANISM: Artificial Sequence
<220> FEATURE:
<223> OTHER INFORMATION: Primer

<400> SEQUENCE: 222
tgacatgaag cggctttcca						20

```
<210> SEQ ID NO 223
<211> LENGTH: 20
<212> TYPE: DNA
<213> ORGANISM: Artificial Sequence
<220> FEATURE:
<223> OTHER INFORMATION: Primer

<400> SEQUENCE: 223
acccctgtcg gagttctcat                                               20

<210> SEQ ID NO 224
<211> LENGTH: 20
<212> TYPE: DNA
<213> ORGANISM: Artificial Sequence
<220> FEATURE:
<223> OTHER INFORMATION: Primer

<400> SEQUENCE: 224
gcgtctcggg agaggattag                                               20

<210> SEQ ID NO 225
<211> LENGTH: 20
<212> TYPE: DNA
<213> ORGANISM: Artificial Sequence
<220> FEATURE:
<223> OTHER INFORMATION: Primer

<400> SEQUENCE: 225
gcctagaacc ccactacagc                                               20

<210> SEQ ID NO 226
<211> LENGTH: 21
<212> TYPE: DNA
<213> ORGANISM: Artificial Sequence
<220> FEATURE:
<223> OTHER INFORMATION: Primer

<400> SEQUENCE: 226
cccacagcta cttggtttgt g                                             21

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
tttcttcttg actggcacgc                                               20

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
ctgcgtgcca gtcaagaaga                                               20

<210> SEQ ID NO 229
<211> LENGTH: 20
<212> TYPE: DNA
<213> ORGANISM: Artificial Sequence
<220> FEATURE:
<223> OTHER INFORMATION: Primer
```

```
<400> SEQUENCE: 229
accttccggt gtgaaacatc                                                     20

<210> SEQ ID NO 230
<211> LENGTH: 22
<212> TYPE: DNA
<213> ORGANISM: Artificial Sequence
<220> FEATURE:
<223> OTHER INFORMATION: Primer

<400> SEQUENCE: 230
gcagaggatg ttcataaggc ca                                                  22

<210> SEQ ID NO 231
<211> LENGTH: 20
<212> TYPE: DNA
<213> ORGANISM: Artificial Sequence
<220> FEATURE:
<223> OTHER INFORMATION: Primer

<400> SEQUENCE: 231
gatgactctg ggaaacgcca                                                     20

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
ctgcgaagtg gaaaccatcc                                                     20

<210> SEQ ID NO 233
<211> LENGTH: 20
<212> TYPE: DNA
<213> ORGANISM: Artificial Sequence
<220> FEATURE:
<223> OTHER INFORMATION: Primer

<400> SEQUENCE: 233
aagacctcct cctcgcactt                                                     20

<210> SEQ ID NO 234
<211> LENGTH: 20
<212> TYPE: DNA
<213> ORGANISM: Artificial Sequence
<220> FEATURE:
<223> OTHER INFORMATION: Primer

<400> SEQUENCE: 234
gccatgaact acctggaccg                                                     20

<210> SEQ ID NO 235
<211> LENGTH: 20
<212> TYPE: DNA
<213> ORGANISM: Artificial Sequence
<220> FEATURE:
<223> OTHER INFORMATION: Primer

<400> SEQUENCE: 235
caatgaaatc gtgcggggtc                                                     20
```

```
<210> SEQ ID NO 236
<211> LENGTH: 22
<212> TYPE: DNA
<213> ORGANISM: Artificial Sequence
<220> FEATURE:
<223> OTHER INFORMATION: Primer

<400> SEQUENCE: 236
acacttcctc tccaaaatgc ca                                              22

<210> SEQ ID NO 237
<211> LENGTH: 21
<212> TYPE: DNA
<213> ORGANISM: Artificial Sequence
<220> FEATURE:
<223> OTHER INFORMATION: Primer

<400> SEQUENCE: 237
tgtgaggcgg tagtaggaca g                                               21

<210> SEQ ID NO 238
<211> LENGTH: 20
<212> TYPE: DNA
<213> ORGANISM: Artificial Sequence
<220> FEATURE:
<223> OTHER INFORMATION: Primer

<400> SEQUENCE: 238
gtgatcaagt gtgacccgga                                                 20

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
gccctcagat gtccacgtcc                                                 20

<210> SEQ ID NO 240
<211> LENGTH: 22
<212> TYPE: DNA
<213> ORGANISM: Artificial Sequence
<220> FEATURE:
<223> OTHER INFORMATION: Primer

<400> SEQUENCE: 240
aagtggagct caagaatagc tt                                              22

<210> SEQ ID NO 241
<211> LENGTH: 24
<212> TYPE: DNA
<213> ORGANISM: Artificial Sequence
<220> FEATURE:
<223> OTHER INFORMATION: Primer

<400> SEQUENCE: 241
tctttgttct tggtaaggct caga                                            24

<210> SEQ ID NO 242
<211> LENGTH: 24
<212> TYPE: DNA
<213> ORGANISM: Artificial Sequence
<220> FEATURE:
<223> OTHER INFORMATION: Primer
```

<400> SEQUENCE: 242
actgattgtc cacttcacct tttt                                    24

<210> SEQ ID NO 243
<211> LENGTH: 23
<212> TYPE: DNA
<213> ORGANISM: Artificial Sequence
<220> FEATURE:
<223> OTHER INFORMATION: Primer

<400> SEQUENCE: 243
agtacacatc agcctgtatc caa                                     23

<210> SEQ ID NO 244
<211> LENGTH: 22
<212> TYPE: DNA
<213> ORGANISM: Artificial Sequence
<220> FEATURE:
<223> OTHER INFORMATION: Primer

<400> SEQUENCE: 244
tcttggatac aggctgatgt gt                                      22

<210> SEQ ID NO 245
<211> LENGTH: 20
<212> TYPE: DNA
<213> ORGANISM: Artificial Sequence
<220> FEATURE:
<223> OTHER INFORMATION: Primer

<400> SEQUENCE: 245
tctctcccca tgaaaagcct                                         20

<210> SEQ ID NO 246
<211> LENGTH: 23
<212> TYPE: DNA
<213> ORGANISM: Artificial Sequence
<220> FEATURE:
<223> OTHER INFORMATION: Primer

<400> SEQUENCE: 246
agtgatttcc ctgtattggg ttt                                     23

<210> SEQ ID NO 247
<211> LENGTH: 22
<212> TYPE: DNA
<213> ORGANISM: Artificial Sequence
<220> FEATURE:
<223> OTHER INFORMATION: Primer

<400> SEQUENCE: 247
tctttgttct tggtaaggct ca                                      22

<210> SEQ ID NO 248
<211> LENGTH: 23
<212> TYPE: DNA
<213> ORGANISM: Artificial Sequence
<220> FEATURE:
<223> OTHER INFORMATION: Primer

<400> SEQUENCE: 248
acaggctgat gtgtacttaa cca                                     23

```
<210> SEQ ID NO 249
<211> LENGTH: 22
<212> TYPE: DNA
<213> ORGANISM: Artificial Sequence
<220> FEATURE:
<223> OTHER INFORMATION: Primer

<400> SEQUENCE: 249
gcataatccc aatctctccc ca                                                22

<210> SEQ ID NO 250
<211> LENGTH: 15
<212> TYPE: DNA
<213> ORGANISM: Artificial Sequence
<220> FEATURE:
<223> OTHER INFORMATION: Primer

<400> SEQUENCE: 250
cagcggcggc tcgga                                                        15

<210> SEQ ID NO 251
<211> LENGTH: 22
<212> TYPE: DNA
<213> ORGANISM: Artificial Sequence
<220> FEATURE:
<223> OTHER INFORMATION: Primer

<400> SEQUENCE: 251
caggtcagag aactagaacg cc                                                22

<210> SEQ ID NO 252
<211> LENGTH: 21
<212> TYPE: DNA
<213> ORGANISM: Artificial Sequence
<220> FEATURE:
<223> OTHER INFORMATION: Primer

<400> SEQUENCE: 252
tcggtaccgt agacttcaac a                                                 21

<210> SEQ ID NO 253
<211> LENGTH: 22
<212> TYPE: DNA
<213> ORGANISM: Artificial Sequence
<220> FEATURE:
<223> OTHER INFORMATION: Primer

<400> SEQUENCE: 253
tgttgctgtt ccattttcgt ca                                                22

<210> SEQ ID NO 254
<211> LENGTH: 23
<212> TYPE: DNA
<213> ORGANISM: Artificial Sequence
<220> FEATURE:
<223> OTHER INFORMATION: Primer

<400> SEQUENCE: 254
tcagaggtca tgtcaaaaga gga                                               23

<210> SEQ ID NO 255
<211> LENGTH: 23
<212> TYPE: DNA
<213> ORGANISM: Artificial Sequence
<220> FEATURE:
<223> OTHER INFORMATION: Primer
```

<400> SEQUENCE: 255
tcctcttttg acatgacctc tga                                         23

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
gacccagtcc ggaagtgtaa                                             20

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
tacacttccg gactgggtca                                             20

<210> SEQ ID NO 258
<211> LENGTH: 20
<212> TYPE: DNA
<213> ORGANISM: Artificial Sequence
<220> FEATURE:
<223> OTHER INFORMATION: Primer

<400> SEQUENCE: 258
ttgtctgtgg ccctttgtct                                             20

<210> SEQ ID NO 259
<211> LENGTH: 21
<212> TYPE: DNA
<213> ORGANISM: Artificial Sequence
<220> FEATURE:
<223> OTHER INFORMATION: Primer

<400> SEQUENCE: 259
tgtagacaaa gggccacaga c                                           21

<210> SEQ ID NO 260
<211> LENGTH: 22
<212> TYPE: DNA
<213> ORGANISM: Artificial Sequence
<220> FEATURE:
<223> OTHER INFORMATION: Primer

<400> SEQUENCE: 260
cttttgactg gtactccctt gc                                          22

<210> SEQ ID NO 261
<211> LENGTH: 20
<212> TYPE: DNA
<213> ORGANISM: Artificial Sequence
<220> FEATURE:
<223> OTHER INFORMATION: Primer

<400> SEQUENCE: 261
tctgcaaagt ccctttccgt                                             20

```
<210> SEQ ID NO 262
<211> LENGTH: 23
<212> TYPE: DNA
<213> ORGANISM: Artificial Sequence
<220> FEATURE:
<223> OTHER INFORMATION: Primer

<400> SEQUENCE: 262
tccactttca aagaagcagg aga                                              23

<210> SEQ ID NO 263
<211> LENGTH: 23
<212> TYPE: DNA
<213> ORGANISM: Artificial Sequence
<220> FEATURE:
<223> OTHER INFORMATION: Primer

<400> SEQUENCE: 263
ggaacttcaa gagcaacatc aga                                              23

<210> SEQ ID NO 264
<211> LENGTH: 21
<212> TYPE: DNA
<213> ORGANISM: Artificial Sequence
<220> FEATURE:
<223> OTHER INFORMATION: Primer

<400> SEQUENCE: 264
ccgagaaaga gctgttgtgg a                                                21

<210> SEQ ID NO 265
<211> LENGTH: 20
<212> TYPE: DNA
<213> ORGANISM: Artificial Sequence
<220> FEATURE:
<223> OTHER INFORMATION: Primer

<400> SEQUENCE: 265
acagctcttt ctcggtccac                                                  20

<210> SEQ ID NO 266
<211> LENGTH: 21
<212> TYPE: DNA
<213> ORGANISM: Artificial Sequence
<220> FEATURE:
<223> OTHER INFORMATION: Primer

<400> SEQUENCE: 266
aggcttgatg ggtccatgtc t                                                21

<210> SEQ ID NO 267
<211> LENGTH: 21
<212> TYPE: DNA
<213> ORGANISM: Artificial Sequence
<220> FEATURE:
<223> OTHER INFORMATION: Primer

<400> SEQUENCE: 267
aaaaagcagc accttgtgac c                                                21

<210> SEQ ID NO 268
<211> LENGTH: 20
<212> TYPE: DNA
<213> ORGANISM: Artificial Sequence
<220> FEATURE:
<223> OTHER INFORMATION: Primer
```

```
<400> SEQUENCE: 268 accccccagtc ggatcttcag                                              20

<210> SEQ ID NO 269
<211> LENGTH: 19
<212> TYPE: DNA
<213> ORGANISM: Artificial Sequence
<220> FEATURE:
<223> OTHER INFORMATION: Primer

<400> SEQUENCE: 269
atccgactgg gggttccaa                                                19

<210> SEQ ID NO 270
<211> LENGTH: 23
<212> TYPE: DNA
<213> ORGANISM: Artificial Sequence
<220> FEATURE:
<223> OTHER INFORMATION: Primer

<400> SEQUENCE: 270
ttcaaaggtg gtcagtctgg att                                           23

<210> SEQ ID NO 271
<211> LENGTH: 23
<212> TYPE: DNA
<213> ORGANISM: Artificial Sequence
<220> FEATURE:
<223> OTHER INFORMATION: Primer

<400> SEQUENCE: 271
tccccatctt ctctttaatt ggt                                           23

<210> SEQ ID NO 272
<211> LENGTH: 24
<212> TYPE: DNA
<213> ORGANISM: Artificial Sequence
<220> FEATURE:
<223> OTHER INFORMATION: Primer

<400> SEQUENCE: 272
ggaccaatta aagagaagat gggg                                          24

<210> SEQ ID NO 273
<211> LENGTH: 22
<212> TYPE: DNA
<213> ORGANISM: Artificial Sequence
<220> FEATURE:
<223> OTHER INFORMATION: Primer

<400> SEQUENCE: 273
tgttcttggt aaggctcaga aa                                            22

<210> SEQ ID NO 274
<211> LENGTH: 15
<212> TYPE: PRT
<213> ORGANISM: Artificial Sequence
<220> FEATURE:
<223> OTHER INFORMATION: PEPTIDE

<400> SEQUENCE: 274

Phe His Glu Ile Asn Asn Lys Met Val Glu Cys Lys Lys Ala Gln
1               5                   10                  15
```

```
<210> SEQ ID NO 275
<211> LENGTH: 15
<212> TYPE: PRT
<213> ORGANISM: Artificial Sequence
<220> FEATURE:
<223> OTHER INFORMATION: PEPTIDE

<400> SEQUENCE: 275

Met Val Glu Cys Lys Lys Ala Gln Pro Lys Glu Val Met Ser Pro
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: PEPTIDE

<400> SEQUENCE: 276

Gln Pro Lys Glu Val Met Ser Pro Thr Gly Ser Ala Arg Gly Arg
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: PEPTIDE

<400> SEQUENCE: 277

Pro Thr Gly Ser Ala Arg Gly Arg Ser Arg Val Met Pro Tyr Gly
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: PEPTIDE

<400> SEQUENCE: 278

Arg Ser Arg Val Met Pro Tyr Gly Met Asp Ala Phe Met Leu Gly
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: PEPTIDE

<400> SEQUENCE: 279

Gly Met Asp Ala Phe Met Leu Gly Ile Gly Met Leu Gly Tyr Pro
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: PEPTIDE

<400> SEQUENCE: 280

Gly Ile Gly Met Leu Gly Tyr Pro Gly Phe Gln Ala Thr Thr Tyr
1               5                   10                  15
```

```
<210> SEQ ID NO 281
<211> LENGTH: 15
<212> TYPE: PRT
<213> ORGANISM: Artificial Sequence
<220> FEATURE:
<223> OTHER INFORMATION: PEPTIDE

<400> SEQUENCE: 281

Pro Gly Phe Gln Ala Thr Thr Tyr Ala Ser Arg Ser Tyr Thr Gly
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: PEPTIDE

<400> SEQUENCE: 282

Tyr Ala Ser Arg Ser Tyr Thr Gly Leu Ala Pro Gly Tyr Thr Tyr
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: PEPTIDE

<400> SEQUENCE: 283

Gly Leu Ala Pro Gly Tyr Thr Tyr Gln Phe Pro Glu Phe Arg Val
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: PEPTIDE

<400> SEQUENCE: 284

Tyr Gln Phe Pro Glu Phe Arg Val Glu Arg Thr Pro Leu Pro Ser
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: PEPTIDE

<400> SEQUENCE: 285

Val Glu Arg Thr Pro Leu Pro Ser Ala Pro Val Leu Pro Glu Leu
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: PEPTIDE

<400> SEQUENCE: 286

Ser Ala Pro Val Leu Pro Glu Leu Thr Ala Ile Pro Leu Thr Ala
1               5                   10                  15
```

```
<210> SEQ ID NO 287
<211> LENGTH: 15
<212> TYPE: PRT
<213> ORGANISM: Artificial Sequence
<220> FEATURE:
<223> OTHER INFORMATION: PEPTIDE

<400> SEQUENCE: 287

Leu Thr Ala Ile Pro Leu Thr Ala Tyr Gly Pro Met Ala Ala Ala
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: PEPTIDE

<400> SEQUENCE: 288

Ala Tyr Gly Pro Met Ala Ala Ala Ala Ala Ala Ala Ala Val Val
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: PEPTIDE

<400> SEQUENCE: 289

Ala Ala Ala Ala Ala Ala Val Val Arg Gly Thr Gly Ser His Pro
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: PEPTIDE

<400> SEQUENCE: 290

Val Arg Gly Thr Gly Ser His Pro Trp Thr Met Ala Pro Pro Pro
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: PEPTIDE

<400> SEQUENCE: 291

Pro Trp Thr Met Ala Pro Pro Pro Gly Ser Thr Pro Ser Arg Thr
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: PEPTIDE

<400> SEQUENCE: 292

Pro Gly Ser Thr Pro Ser Arg Thr Gly Gly Phe Leu Gly Thr Thr
1               5                   10                  15
```

-continued

<210> SEQ ID NO 293
<211> LENGTH: 15
<212> TYPE: PRT
<213> ORGANISM: Artificial Sequence
<220> FEATURE:
<223> OTHER INFORMATION: PEPTIDE

<400> SEQUENCE: 293

Thr Gly Gly Phe Leu Gly Thr Thr Ser Pro Gly Pro Met Ala Glu
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: PEPTIDE

<400> SEQUENCE: 294

Thr Ser Pro Gly Pro Met Ala Glu Leu Tyr Gly Ala Ala Asn Gln
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: PEPTIDE

<400> SEQUENCE: 295

Glu Leu Tyr Gly Ala Ala Asn Gln Asp Ser Gly Val Ser Ser Tyr
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: PEPTIDE

<400> SEQUENCE: 296

Gln Asp Ser Gly Val Ser Ser Tyr Ile Ser Ala Ala Ser Pro Ala
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: PEPTIDE

<400> SEQUENCE: 297

Tyr Ile Ser Ala Ala Ser Pro Ala Pro Ser Thr Gly Phe Gly His
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: PEPTIDE

<400> SEQUENCE: 298

Ala Pro Ser Thr Gly Phe Gly His Ser Leu Gly Gly Pro Leu Ile
1               5                   10                  15

```
<210> SEQ ID NO 299
<211> LENGTH: 15
<212> TYPE: PRT
<213> ORGANISM: Artificial Sequence
<220> FEATURE:
<223> OTHER INFORMATION: PEPTIDE

<400> SEQUENCE: 299

His Ser Leu Gly Gly Pro Leu Ile Ala Thr Ala Phe Thr Asn Gly
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: PEPTIDE

<400> SEQUENCE: 300

Leu Gly Gly Pro Leu Ile Ala Thr Ala Phe Thr Asn Gly Tyr His
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: PEPTIDE

<400> SEQUENCE: 301

Gly Ser His Pro Trp Thr Met Ala Pro Pro Gly Ser Thr Pro
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: PEPTIDE

<400> SEQUENCE: 302

Tyr Gln Phe Pro Glu Phe Arg Val Glu Arg Thr Pro Leu Pro Ser
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: PEPTIDE

<400> SEQUENCE: 303

His Ser Leu Gly Gly Pro Leu Ile Ala Thr Ala Phe Thr Asn Gly
1               5                   10                  15

<210> SEQ ID NO 304
<211> LENGTH: 28
<212> TYPE: PRT
<213> ORGANISM: Artificial Sequence
<220> FEATURE:
<223> OTHER INFORMATION: PEPTIDE

<400> SEQUENCE: 304

Gly Ser His Pro Trp Thr Met Ala Pro Pro Gly Ser Thr Pro Gly
1               5                   10                  15

Arg Lys Lys Arg Arg Gln Arg Arg Pro Pro Gln
                20                  25
```

```
<210> SEQ ID NO 305
<211> LENGTH: 28
<212> TYPE: PRT
<213> ORGANISM: Artificial Sequence
<220> FEATURE:
<223> OTHER INFORMATION: PEPTIDE

<400> SEQUENCE: 305

Tyr Gln Phe Pro Glu Phe Arg Val Glu Arg Thr Pro Leu Pro Ser Gly
1               5                   10                  15

Arg Lys Lys Arg Arg Gln Arg Arg Pro Pro Gln
            20                  25

<210> SEQ ID NO 306
<211> LENGTH: 28
<212> TYPE: PRT
<213> ORGANISM: Artificial Sequence
<220> FEATURE:
<223> OTHER INFORMATION: PEPTIDE

<400> SEQUENCE: 306

His Ser Leu Gly Gly Pro Leu Ile Ala Thr Ala Phe Thr Asn Gly Gly
1               5                   10                  15

Arg Lys Lys Arg Arg Gln Arg Arg Pro Pro Gln
            20                  25

<210> SEQ ID NO 307
<211> LENGTH: 24
<212> TYPE: PRT
<213> ORGANISM: Artificial Sequence
<220> FEATURE:
<223> OTHER INFORMATION: PEPTIDE

<400> SEQUENCE: 307

Gly Ser His Pro Trp Thr Met Ala Pro Pro Gly Ser Thr Pro Arg
1               5                   10                  15

Arg Arg Arg Arg Arg Arg Arg Arg
            20

<210> SEQ ID NO 308
<211> LENGTH: 24
<212> TYPE: PRT
<213> ORGANISM: Artificial Sequence
<220> FEATURE:
<223> OTHER INFORMATION: PEPTIDE

<400> SEQUENCE: 308

Tyr Gln Phe Pro Glu Phe Arg Val Glu Arg Thr Pro Leu Pro Ser Arg
1               5                   10                  15

Arg Arg Arg Arg Arg Arg Arg Arg
            20

<210> SEQ ID NO 309
<211> LENGTH: 24
<212> TYPE: PRT
<213> ORGANISM: Artificial Sequence
<220> FEATURE:
<223> OTHER INFORMATION: PEPTIDE

<400> SEQUENCE: 309

His Ser Leu Gly Gly Pro Leu Ile Ala Thr Ala Phe Thr Asn Gly Arg
1               5                   10                  15

Arg Arg Arg Arg Arg Arg Arg Arg
            20
```

```
<210> SEQ ID NO 310
<211> LENGTH: 28
<212> TYPE: PRT
<213> ORGANISM: Artificial Sequence
<220> FEATURE:
<223> OTHER INFORMATION: PEPTIDE

<400> SEQUENCE: 310

Gly Ser His Pro Trp Thr Met Ala Pro Pro Pro Gly Ser Thr Pro Gly
1               5                   10                  15

Arg Lys Lys Arg Arg Gln Arg Arg Pro Pro Gln
            20                  25

<210> SEQ ID NO 311
<211> LENGTH: 28
<212> TYPE: PRT
<213> ORGANISM: Artificial Sequence
<220> FEATURE:
<223> OTHER INFORMATION: PEPTIDE

<400> SEQUENCE: 311

Tyr Gln Phe Pro Glu Phe Arg Val Glu Arg Thr Pro Leu Pro Ser Gly
1               5                   10                  15

Arg Lys Lys Arg Arg Gln Arg Arg Pro Pro Gln
            20                  25

<210> SEQ ID NO 312
<211> LENGTH: 28
<212> TYPE: PRT
<213> ORGANISM: Artificial Sequence
<220> FEATURE:
<223> OTHER INFORMATION: PEPTIDE

<400> SEQUENCE: 312

His Ser Leu Gly Gly Pro Leu Ile Ala Thr Ala Phe Thr Asn Gly Gly
1               5                   10                  15

Arg Lys Lys Arg Arg Gln Arg Arg Pro Pro Gln
            20                  25
```